US012629341B2

(12) United States Patent
Overduin et al.

(10) Patent No.: US 12,629,341 B2
(45) Date of Patent: May 19, 2026

(54) FUNCTIONAL DERIVATIVES OF MALEIMIDE COPOLYMERS FOR NANODISC PRODUCTION

(71) Applicant: The Governors of the University of Alberta, Edmonton (CA)

(72) Inventors: Michael Overduin, Edmonton (CA); Mansoore Esmaili, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 897 days.

(21) Appl. No.: 17/770,720

(22) PCT Filed: Oct. 23, 2020

(86) PCT No.: PCT/US2020/057069
§ 371 (c)(1),
(2) Date: Apr. 21, 2022

(87) PCT Pub. No.: WO2021/081329
PCT Pub. Date: Apr. 29, 2021

(65) Prior Publication Data

US 2022/0347114 A1 Nov. 3, 2022

Related U.S. Application Data

(60) Provisional application No. 62/925,086, filed on Oct. 23, 2019.

(51) Int. Cl.
*C08F 212/08* (2006.01)
*A61K 9/51* (2006.01)

(52) U.S. Cl.
CPC .......... *A61K 9/5138* (2013.01); *C08F 212/08* (2013.01)

(58) Field of Classification Search
CPC .... C08F 212/08; C08F 222/02; C08F 222/38; C08F 222/40; C08F 222/402; C08F 222/404; C08F 222/406
See application file for complete search history.

(56) References Cited

U.S. PATENT DOCUMENTS 3,554,985 A * 1/1971 Fields ....................... C08F 8/00 526/306
6,436,905 B1 8/2002 Tonge et al.
(Continued)

FOREIGN PATENT DOCUMENTS

EP 2431613 B1 12/2019
JP 2013239222 A 11/2013
(Continued)

OTHER PUBLICATIONS

Henry, Biomacromolecules 2006, 7, 2407-2414 (Year: 2006).*
(Continued)

*Primary Examiner* — Robert C Boyle
(74) *Attorney, Agent, or Firm* — Haukaas Fortius PLLC; Michael H. Haukaas; Raymond F. Horvath

(57) ABSTRACT

Amphiphilic copolymers and compositions including amphiphilic copolymers. The amphiphilic copolymers include modified maleimide subunits, for example, as illustrated by the structures of Formula $I^A$ and Formula $I^B$. The compositions form water-soluble complexes upon association with biological material wherein such biological material can include lipids or membrane proteins. Methods for producing, purifying, analyzing, and using the compositions and complexes are provided.

21 Claims, 45 Drawing Sheets

(56) References Cited

U.S. PATENT DOCUMENTS

| | | | | |
|---|---|---|---|---|
| 7,871,818 | B2 | 1/2011 | Rozema et al. | |
| 8,623,414 | B2 | 1/2014 | Tonge | |
| 8,754,168 | B2 | 6/2014 | Dafforn et al. | |
| 9,523,086 | B2 | 12/2016 | Dafforn et al. | |
| 2005/0032929 | A1 | 2/2005 | Greener | |
| 2006/0057209 | A1* | 3/2006 | Chapman | H01J 49/167 424/486 |
| 2006/0057662 | A1 | 3/2006 | Sligar et al. | |
| 2009/0155375 | A1 | 6/2009 | Tonge | |
| 2012/0142861 | A1 | 6/2012 | Dafforn et al. | |
| 2016/0317672 | A1 | 11/2016 | Maeda et al. | |
| 2017/0207149 | A1 | 7/2017 | Liang | |
| 2018/0237653 | A1* | 8/2018 | Cloete | C09D 7/65 |
| 2019/0062469 | A1 | 2/2019 | Altenberg et al. | |
| 2019/0154698 | A1* | 5/2019 | Ramamoorthy | C08F 8/44 |

FOREIGN PATENT DOCUMENTS

| | | | |
|---|---|---|---|
| WO | 1998027434 | A1 | 6/1998 |
| WO | 1999009955 | A1 | 3/1999 |
| WO | WO 03/027154 | * | 4/2003 |
| WO | 2006129127 | A1 | 12/2006 |
| WO | 2011004158 | A1 | 1/2011 |
| WO | 2016122648 | A1 | 8/2016 |

OTHER PUBLICATIONS

Li, Journal of Polymer Science Part B: Polymer Physics, vol. 51, Issue 21, Nov. 2013, p. 1523-1591 (Year: 2013).*

By Lokaj, Journal of Applied Polymer Science, vol. 67, Issue 4, Jan. 1998, p. 755-762 (Year: 1998).*

Beriashvili et al., "Characterization of Multimeric Daptomycin Bound to Lipid Nanodiscs Formed by Calcium-Tolerant Styrene-Maleic Acid Copolymer," Biochimica et Biophysica Acta (BBA)—Biomembranes, 1862(6):183234, Jun. 2020.

Esmaili et al., "Homogeneous Nanodiscs of Native Membranes Formed by Stilbene-Maleic-Acid Copolymers," Nanoscale, 12(22):16705, Aug. 2020.

Esmaili et al., "Native Nanodiscs Formed by Styrene Maleic Acid Copolymer Derivatives Help Recover Infectious Prion Ultimers Bound to Brain-Derived Lipids," J Biol Chem., 295(25):8460-8469, Jun. 2020.

Esmaili et al., "The Effect of Hydrophobic Alkyl Sidechains on Size and Solution Behaviors of Nanodiscs Formed by Alternating Styrene Maleamic Copolymer," Biochimica et Biophysica Acta (BBA)—Biomembranes, 1862(10):183360, May 2020.

International Search Report and Written Opinion of the ISA/US in PCT/US2020/057069, dated Jan. 27, 2021; 8pgs.

Jamshad et al., "G-Protein Coupled Receptor Solubilization and Purification for Biophysical Analysis and Functional Studies, in the Total Absence of Detergent," Biosci Rep., 35(2):e00188, Apr. 2015.

Jamshad et al., "Structural Analysis of a Nanoparticle Containing a Lipid Bilayer Used for Detergent-Free Extraction of Membrane Proteins," Nano Res., 8(3):774-789, Mar. 2015.

Jamshad et al., "Surfactant-Free Purification of Membrane Proteins With Intact Native Membrane Environment," Biochem Soc Trans., 39(3):813-818, Jun. 2011.

Knowles et al., "Membrane Proteins Solubilized Intact in Lipid Containing Nanoparticles Bounded by Styrene Maleic Acid Copolymer," J Am Chem Soc., 131(22):7484-7485, May 2009.

Lee et al., "A Method for Detergent-Free Isolation of Membrane Proteins in Their Local Lipid Environment," Nat Protoc., 11(7):1149-1162, Jul. 2016.

Overduin et al., "Advancing Membrane Biology With Poly(styrene-Co-Maleic Acid)-Based Native Nanodiscs," Eur Polym J., 110:63-68, Jan. 2019.

Overduin et al., "Memtein: The Fundamental Unit of Membrane-Protein Structure and Function," Chem Phys Lipids, 218:73-84, Jan. 2019.

Overduin et al., "Native Nanodiscs and the Convergence of Lipidomics, Metabolomics, Interactomics and Proteomics," Appl Sci., 9(6):1230, Mar. 2019.

Overduin et al., "Structures and Interactions of Transmembrane Targets in Native Nanodiscs," SLAS Discov., 24(10):943-952, Dec. 2019.

Extended Search Report and Written Opinion of the European Patent Office dated Nov. 8, 2023 in EP Application No. 20878138.5; 9pgs.

Grundke et al., "Wettability of Maleimide Copolymer Films: Effect of the Chain Length of n-Alkyl Side Groups on the Solid Surface Tension", Macromolecules 2001, 34, 6768-6775, Aug. 2001.

Savage et al., "A review of semi-rigid, stilbene-containing alternating copolymers", Appl Petrochem Res, 5:27-33, Apr. 2014.

Soer et al., "Surfactant-free artificial latexes from modified styrene-maleic anhydride (SMA) copolymers", Polymer 47, No. 22, 7621-7627, Oct. 2006.

* cited by examiner

B

G

PagP- PA-SMA discs

PagP- EA-SMA discs

PagP- MA-SMA discs

FUNCTIONAL DERIVATIVES OF MALEIMIDE COPOLYMERS FOR NANODISC PRODUCTION

RELATED APPLICATIONS

This application is a National Stage filing under 35 U.S.C. § 371 of International Application No. PCT/US2020/057069 filed Oct. 23, 2020, which claims priority under 35 U.S.C. § 119(e) to U.S. Provisional Patent Application No. 62/925,086 filed Oct. 23, 2019, which applications are incorporated herein by reference.

FIELD OF THE INVENTION

The invention relates to amphiphilic copolymers which are used for solubilization, purification, manipulation and visualization of hydrophobic materials such as lipids or membrane proteins, the water-soluble nanodiscs formed between said copolymers and hydrophobic materials, methods for preparing said complexes, and the applications of said complexes, particularly to analytical, screening or diagnostic purposes.

BACKGROUND OF THE INVENTION

Biological membranes are found within all living cells and contain a large and diverse number of complexes of lipids and proteins. Many of these complexes are targets used for the discovery and design of drug molecules, sensors, probes, transducers and diagnostic assays. A variety of diseases involve lipid-associated proteins including infectious prions, receptors and antibody-ligand complexes. Maintaining the molecular contacts within these complexes is desirable for ensuring that biological function is retained during the preparation and analysis of these complexes. Retention of biological functions within resolvable nanodiscs ensures accurate and precise design of therapeutic agents that specifically interact with membrane targets.

A typical membrane is composed of a bilayer of lipid molecules such as phospholipids and glycolipids. These lipids are differentially arranged in various organdies where they form a selective barrier and also mediate and modulate biological functions such as signalling and membrane trafficking. Most lipid molecules comprise a hydrophilic polar head portion and a hydrophobic tail group. They are arranged with the polar head groups forming the exposed surfaces and the hydrophobic groups contacting the interior of the membrane bilayer. Other lipids such as sterols also serve as additional features of biological membranes. Such membranes surround and protect prokaryotic and eukaryotic cells, in addition to compartmentalizing their components within organelles.

Protein molecules also serve as major structural and functional components of membranes. Approximately one third of the sequences encoded by genomes represent integral membrane proteins that span lipid bilayers. There are also many peripheral membrane proteins which insert partially into or associate reversibly with membranes and regulate membrane assemblies or transduce signals from membranes. The stabilities, structures, specificities and functions of such membrane proteins depend on the lipids they are complexed with, as do the multimeric states they form inside lipid bilayers. Membrane proteins contain one or more hydrophobic regions that interact with a bilayer phase as well as one or more regions which are hydrophilic and are present in the aqueous phase. This situation presents challenges for purification and analysis in aqueous solutions, leading to the design of water-soluble nanodiscs that solubilize membrane protein complexes.

The functions of membrane proteins are highly dependent on their molecular structure including the positions of bound lipids and multimeric states. Their conformations are stabilized by hydrophobic interactions of the membrane-spanning regions within the interior of the membrane bilayer, ionic interactions of the non-embedded regions of the protein with the polar lipid heads and the surrounding aqueous medium, and by interactions (both hydrophobic and ionic) within the protein folds and assemblies. Typical functions of membrane proteins include the transport of ions and small molecules across the cell membrane, and the recognition of ligands by receptors to initiate signaling. Manipulation and exploitation of these processes accurately depends on being able to prepare, stabilize and analyze oligomeric membrane protein complexes with bound lipid molecules. Conversion of membranes directly and efficiently into soluble functional molecular assemblies or nanodiscs that can be readily purified, stored, screened and assayed is highly desirable for research and industry applications. Being able to resolve the molecules structurally within the assemblies and measure their interactions accurately while retaining native-like integrity and activity is also highly desirable and can inform the design of pharmaceutical agents.

Problems being addressed. Multimeric membrane proteins can be very difficult to solubilize and extract from their native environment (i.e. biological membranes) in their active conformations with an intact shell of bound lipid molecules. Integral membrane proteins and the complexes they form are destabilized by removal from the membrane by detergents or denaturants, and their isolation from the membrane results in partial or, in some cases, complete loss of structural integrity, dynamic states and functional activity. Lipids and other ligands including associated protein molecules are typically removed when membrane protein complexes are extracted from membranes using small detergent molecules. The detergents are added above the critical micelle concentrations to solubilize and purify membrane proteins and their presence typically needs to be maintained during subsequent purification processes and assays. The choice of which detergent type and concentration may be most compatible with a given membrane protein is complex and time consuming as multiple types and combinations may need to be tested in activity assays and each offers different critical micelle concentrations, curvature, thickness and lateral pressure profiles and can lead to a variety of structural or functional artifacts [1]. The limitations of small molecule detergents are well-known, creating a demand for new ways to prepare, study and utilize intact membrane protein complexes.

Approaches that center around preserving the original characteristics of the membrane environment within soluble native nanodiscs is becoming particularly crucial. Directly solubilizing intact membrane protein complexes without any exposure to conventional detergent molecules is critical. Improved copolymer compositions are needed that are sufficient to solubilize a diversity of biological complexes of biological lipids and membrane proteins directly from many different organs, cells, tissues or biological membranes for detailed analysis of structure and function as well as applications including drug discovery. The biologically intact membrane-proteins complexes of most interest have been termed "memteins" [1] and when solubilized in native nanodiscs they offer the potential to visualize and exploit the physiological and pathological mechanisms of membrane assemblies in healthy and disease systems.

The science of native nanodiscs and memteins is early in development, and new copolymers are being designed and optimized to progress the field. The size, homogeneity and stability of the native nanodiscs that contain membrane assemblies should be predicted or controlled so that large or unstable proteins can also be solubilized intact. Reduction of the compositional heterogeneity of the copolymer should afford higher resolution and accuracy of resulting structures and dynamics of native complexes within biological membranes. The pH range should be extended so that membrane proteins and cells could be solubilized under a wider variety of conditions including basic or acidic environments typical for some organelles, organs and microorganisms. Nonspecific interactions of copolymers with polyvalent cations should be minimized, while methods of including or attaching groups useful for affinity purification such as hexahistidine peptide tags, as well as detection by fluorescence microscopy, nuclear magnetic resonance (NMR) spectroscopy, X-ray diffraction or electron microscopy should be allowed. Reduction of net subunit charge to between −1 and 1 or ideally to 0 and minimization of hydrophobic microstructures could reduce undesirable nonspecific interactions with drug-like molecules or assay system surfaces such as sensorchips and fluidic devices. Removal of reactants and copolymer populations that are unable to efficiently form nanodiscs of a homogeneous size can be accomplished by repeated copolymer precipitation, resuspension and centrifugation as reported by Tim Dafforn and colleagues in 2018, copolymer fractionation in hexane and acetone mixtures as has been reported by the group of Antoinette Killian at Utrecht University in 2018, removal of free copolymer by single-step purification of nanoparticles by affinity chromatography as reported by Youzhong Guo and colleagues in 2018, or concentration using microfiltration as reported by Tomas Laursen et al. in 2016. Copolymer precipitation can be achieved by mixing with polyvalent counterions or copolymers of opposite charge or pH change, which allows removal of copolymers from solution and transfer of the contained biological material into liposomes or other media. The introduction of steric restraints by presence of additional phenyl rings and alkyl substituents could restrict dynamics and produce more stable or regular nanodiscs. The polar sidechains on the hydrophilic subunits could ideally be incorporated into different copolymers such as alternating, semialternating and nonalternating styrene maleic anhydride, stilbene maleic anhydride and diisobutylene maleic anhydride (DIBMA)-based copolymers, as would be evident to those skilled in the art of copolymer synthesis and activation. Finally, copolymer production should be scalable in order to cost-effectively generate sufficient quantities to process large amounts of biomass or other materials for industrial-scale processes.

Current solutions to this problem. At present, conventional detergent-based methods are routinely used in order to remove membrane proteins from their native environment. Most detergents have an overall molecular structure which is similar to that of lipids found in the membrane bilayer, with a hydrophilic polar head and a hydrophobic tail, and they form micelles at critical concentrations. As such, they are able to bind to both the hydrophobic and hydrophilic regions of the membrane protein, thus displacing native lipids and solubilizing the protein in an aqueous environment. This allows the many different proteins to be separated using standard chromatographic techniques and opens up the possibility of characterization of an isolated protein.

Due to the differences in structure and dynamics of the detergent micelles and the lipid bilayer, it is to be expected that detergents will affect the conformation of the protein. Indeed, denaturing of proteins in detergents is often desirable in order to carry out an assessment of molecular weight and other characterization. However, any such loss in native conformation will lead to a loss in function. As such, solubilization in detergent does not provide a reliable method for determining native protein function. Multimeric protein complexes are generally unstable when isolated in detergent and few have proven amenable to crystallization and high resolution structure determination in the presence of bound biological lipids let alone a natural bilayer [1]. The specific states of membrane proteins depend on the lipid species to which they are attached or bound, and these lipids are usually lost during detergent extraction and cannot be easily replaced.

Many membrane proteins are modified and assembled in cells and can only be obtained from endogenous sources such as biological tissues such as brain or natural sources such as outer membranes of bacteria. That is, they cannot be produced with their post-translational modifications, multimeric organization, co-factors, lipids and peripheral partners intact when they are made in cultures of expression hosts through recombinant methods. Engineered hosts such as mammalian, insect, and yeast and insect larvae systems have been developed to express modified formed of commercial recombinant proteins, but generally yield a heterogeneous set of states that are not identical to the human states of most interest. Consequently, the lack of a generally useful method to solubilize and characterize stable native membrane protein complexes directly from biological source tissue has frustrated efforts to define and exploit their mechanisms.

This situation has led to the development of alternative approaches to prepare membrane proteins. These alternatives include the use of bicelles, which are small discs composed of lipid and surrounded by an annulus of surfactants. The surrounding annulus can also be formed from amphiphilic peptides, lipopeptides, or fluorinated surfactants. Alternatively, a membrane protein can be stabilized by mutagenesis or addition of folded domains into loop regions, although such approaches influence structure, dynamics and function of the recombinant proteins, and are not applicable to endogenous proteins. Moreover, these systems still generally require that the membrane protein goes through a detergent or surfactant phase that removes bound lipid.

Nanodiscs surrounded by membrane scaffold proteins (MSPs) were originally developed by Stephen Sligar and coworkers at the University of Illinois at Urbana-Champaign. This system uses purified and engineered apolipoprotein A-1 proteins to form homogeneous discoidal protein-lipid particles (Sligar et al, US 20060057662 A1). Although various membrane proteins have been reconstituted into nanodiscs, this system was not designed to extract membrane proteins directly from biological material. Disadvantages include the overlap of the signals of MSPs with the embedded membrane protein, and the reliance on detergents to prepare the membrane protein. Covalently circularized nanodiscs that offer higher size homogeneity and improved stability than non-circularized forms have been developed by Mahmoud Nasr and Gerhard Wagner at Harvard Medical School. Hence it is apparent that cyclized copolymers including those described here could offer nanodiscs with higher stability and better-defined sizes than their linear counterparts, and therefore could be well-suited to high resolution structural analysis.

Amphipols are short amphiphilic copolymers that were designed by the group of Jean-Luc Popot (Tribet et al, WO 1998/027434) to have a high affinity for the hydrophobic surfaces of membrane proteins, thus displacing bound detergent or lipid while keeping proteins in compact, soluble states. However, the amphipols were not designed to extract membrane proteins directly from biological material, and the use of amphipols relies on a detergent step to extract proteins directly from membrane.

A native nanodisc can be formed spontaneously by adding an amphiphilic copolymer known as styrene maleic acid (SMA) to a biological membrane. The product is generally known as a styrene maleic acid lipid particle (SMALP), and a related commercial product is known as a Lipodisg™ nanoparticle. Several features of SMALPs make them highly desirable. One is that SMA copolymers can be used to solubilize membranes directly without needing any detergent addition. Another feature is that native lipids and post-translationally modified proteins are maintained in an intact state in SMALPs, allowing studies of membrane proteins in an environment that is more physiologically relevant than the delipidated states. The synthesis of SMA copolymers has been optimized by groups including that led by Bert Klumperman at Stellenbosch University (South Africa) and companies including Polyscope (Geleen, The Netherlands), and hence there are cost-effective routes for production of SMA copolymers including SMALP 25010 P, SMALP 30010 P and SMALP 40005 P for membrane research and industrial scale applications including by pharmaceutical companies.

The use of hydrolyzed alternating copolymers of hydrophilic anionic groups composed of maleic acid and hydrophobic groups composed of styrene or an alkyl vinyl ether to associate with polar phospholipids to form substantially clear aqueous solutions and disc-like assemblies is disclosed in International Patent Application number PCT/GB1998/002546 (Tonge and Tighe, WO 1999/009955, and related patent EP11007002), although neither membrane proteins nor the functionalized derivatives of SMA claimed herein are addressed.

The use of nonalternating SMA copolymers to form macromolecular assemblies from lipid is disclosed in PCT/GB2006/050134 (Tonge, WO 2006/129127 and related patent application US 2009/0155375) but does not encompass alternating SMA copolymers or the SMA derivatives claimed in this invention. Instead this specifies nonalternating copolymers that form macromolecular assemblies and contain a statistically defined distributions of styrene to maleic acid monomers that is greater than 1.2:1. However, such copolymers are relatively polydisperse and heterogeneous in their sequences, leading to reduced spectral resolution, and greater potential for undesirable nonspecific interactions with polycations and proteins.

Soluble macromolecular assemblies such as nanodiscs can be formed directly from cells or biological membranes by addition of a copolymer composed of a chain of nonalternating styrene maleic acid subunits, as Michael Overduin, Tim Dafforn and Tim Knowles previously published [4] and disclosed (WO 2011/004158A1 and US 2012/0142861). The resulting SMA lipid particle (SMALP) system has been used effectively with a set of nonalternating styrene maleic acid (SMA) copolymers which contain styrene subunits interspersed between maleic acid subunits in ratios of between 1:2 and 10:1 and typically with S:MA ratios of approximately 2:1 or 3:1 [SMA(2:1) or SMA(3:1)]. These copolymers spontaneously form nanodiscs when added to biological membranes and have been applied to many membrane proteins from diverse prokaryotic and eukaryotic cell types and tissues including plant and animal matter (see references in [1]), demonstrating their capabilities. These copolymers have also been used to disrupt membranes of bacterial cells as disclosed (Dafforn and Tyrynis-Thomas, U.S. Ser. No. 14/116,584) in order to lyse the cells and liberate the intracellular contents. However complicating issues have been reported including incompatibility with elevated concentrations of polyvalent cations or low pH levels as well as compositional heterogeneity that can limit their utility and structural resolution [1], leading to an ongoing search for improved copolymers.

Polyvalent cations such as calcium are known to bind to maleic acid, neutralizing the anionic character that is needed for maintaining solubility. The consequences can include precipitated copolymer. This behaviour is avoided by optimizing the charge, polarity, hydrophobicity and dynamics of the copolymer, which is accomplished by functional derivatives of maleimide and styrene or stilbene subunit-containing (FDM) copolymers described herein. The narrow pH range over which SMA copolymers can be used to solubilize membranes is due to precipitation caused by the protonation of the maleic acid groups at lower pH values, which yields a less charged and more hydrophobic copolymer. The high degree of charge in the maleic acid also leads to electrostatic repulsion between nanodiscs, which makes it unlikely that the discs will crystallize in the regular lattices needed for X-ray diffraction (XRD) studies. The charges can also lead to nonspecific electrostatic interactions with surfaces that contain positively or negatively charged groups, respectively, complicating efforts to assay or screen immobilized proteins. The charge of the copolymer annulus also contributes to the limited size of SMA-based nanodiscs, which are typically about 10 nm in diameter. Many membrane assemblies are larger than can easily be accommodated in such small nanodiscs.

The compositional heterogeneity of available nonalternating SMA copolymers limits the resolution of structural studies of the copolymers, nanodiscs or contained lipids and proteins, and can also lead to nonspecific binding to proteins including antibodies and affinity tags such as polyhistidine sequences, thus creating problems for purification. The statistical distribution of styrene and maleic acid monomers leads to various hydrophobic and anionic clusters that can interact preferentially with some proteins, compromising activity and resolution. Such issues reduce the broader utility of conventional SMA copolymers and along with the net charge make it difficult to generate discs of larger sizes to solubilize large membrane proteins or to find ways to immobilize discs on surfaces or use them for ligand screening or activity assays. Hence there remains a need for copolymers with improved properties and consistent solution behavior under a wider range of conditions for production of nanodiscs of various sizes.

An aminoethanol-substituted form of a 1.6 kDa SMA copolymer (SMA-EA) with an average distribution of styrene to maleic subunits of 1.3:1 was developed for making nanodiscs from synthetic liposomes composed of 1,2-dimyristoyl-sn-glycero-3-phosphocholine (DMPC) lipid [5]. The use of this short SMA-EA copolymer was reported to produce larger discs up to ~60 nm in diameter that could be aligned in magnets for NMR analysis, as disclosed in a publication that has since been retracted [6]. Due to its low molecular weight, the SMA-EA copolymer, which has a Number Averaged Molecular Weight (Mn) of approximately 1.6 kDa, behaves more like conventional detergents than longer copolymers described herein. Moreover SMA-EA is not strictly alternating in sequence, retaining a statistical distribution of subunits along their length, and hence limiting resolution and introducing potential undesirable nonspecific interactions.

An ethylenediamine-substituted form of a 1.6 kDa SMA (1.3:1) copolymer (SMA-ED) was developed for making nanodiscs under a variety of pH and divalent metal ion concentrations [7]. The zwitterionic SMA-ED copolymer as well as a hydrolyzed version, SMAd-A, which is positively charged except under neutral pH, were synthesized and tested. The pH dependent and metal ion stability profiles of these nanodiscs were demonstrated, as was their ability to encapsulate and stabilize a polyphenolic natural product curcumin, as disclosed (Ramamoorthy et al, US 2019/0154698). These copolymers have low number averaged molecular weights and sequences composed of a statistical distribution of comonomers which are not strictly alternating, and hence have disadvantages similar to those developed previously.

A positively charged copolymer with quaternary-ammonium groups on a 1.6 kDa SMA copolymer (SMA-QA) was developed to make large nanodiscs and to provide utility over a wide range of divalent metal ion concentrations and pH values [8]. This copolymer was used for structural studies of a cytochrome protein using solid-state NMR techniques [9], as disclosed (Ramamoorthy et al, US 2019/0154698). Negatively charged nonalternating SMA copolymer nanodiscs were shown to inactivate the protein, and it was inferred that this is due to charge—charge and hydrophobic interactions between these copolymers and the protein. While the SMA-QA nanodiscs could be used to reconstitute functional protein, this could only be accomplished in the presence of a high ionic strength medium.

Positively charged copolymers containing a 2:1 ratio of styrene and maleimide subunits have been shown to solubilize an active human G-protein Coupled Receptor (GPCR) protein expressed in cultured HEK 293T cells under acidic pH conditions and in the presence of high concentrations of divalent cations [10]. This poly(styrene-co- dimethylaminopropylamine-maleimide) copolymer forms nanoparticles of diameters of around 6 to 11 nm that are similar to those made by addition of other nonalternating SMA copolymers to membranes.

Those skilled in the art would recognize that alternating SMA copolymer with a 1:1 ratio of hydrophobic and hydrophilic subunits possess lower compositional heterogeneity. This would be useful in improving structural resolution and reducing nonspecific interactions due to charged or hydrophobic clusters.

Alternating SMA1000 copolymer and its derivatives have been shown to be useful in other industrial applications (WO 2016/122648, US 2017/0207149, W. J. Soer et al. 2006. copolymer 47 7621e7627) but surprisingly have not been exploited effectively for use with membrane proteins. Various studies have indicated that SMA copolymers with a 1:1 ratio of styrene and maleic acid such as SMA1000 (Sartomer and Total Cray Valley) are relatively ineffectual at solubilizing membrane proteins. In particular, that such unmodified alternating SMA(1:1) copolymers with a 1:1 ratio of styrene and maleic acid subunits do not efficiently solubilize membranes has been reported based on their interactions with lipid vesicles [11], spinach chloroplast thylakoids [12] and *E. coli*, insect and mammalian cells [13]. Unlike the inventions reported here on derivatized alternating SMA(1:1) copolymers which are shown to be surprisingly effective and useful, other groups have explored other nonalternating SMA copolymers with higher ratios of styrene subunits.

The utility of SMA copolymers for delivery of therapeutic molecules is established. It has been reported that 32 kDa and 64 kDa poly(styrene-alt-maleic anhydride) molecules, which are partially derivatized with pentylamine sidechains, cause effective hemolysis at pH 5.8 and 6.6 although not at pH 7.4 [14]. This pH-dependent membrane-destabilizing activity can be utilized to enhance the intracellular delivery of therapeutic macromolecules through the endosomal membrane barrier into the cytoplasm of targeted cells. The covalent attachment of drug molecules including endorphin and enkephalin to SMA copolymers is disclosed (Maedi et al, JP2013239222, US 2016/0317672 and U.S. Ser. No. 15/037,723). Such conjugates have been shown to be useful for delivery of carcinostatic agents and for diagnostic and therapeutic purposes [15].

Molecular complexes of styrene-maleic anhydride copolymers have been disclosed for the purpose of delivery of compounds such as polynucleotides into the cellular cytoplasm (Rozema and Wakefield, U.S. Pat. No. 7,871,818). However selective targeting can be compromised by nonspecific interactions of the copolymers which lead to unpredictable effects in vivo and the SMA copolymers can end up in the liver, spleen and kidney.

A chemically distinct group of zwitterionic SMA ("zSMA") copolymers were designed to solubilize membrane proteins into nanodiscs in solutions including low pH or polyvalent cations [16], as has been disclosed (Altenberg and Liang, US 2019/0062469). These contain phosphatidylcholine-based sidechain groups and lack any maleic acid groups and thus are not actually SMA copolymers but rather form another class of copolymers that do not overlap structurally with those that are claimed here. The long pendant sidechains of zSMA copolymers also provide different properties and liabilities than the copolymer compositions claimed herein.

Membrane proteins can be solubilized by a copolymer known as DIBMA or Sokalaan® CP9, which is commercialized by BASF. This alternating copolymer also solubilizes phospholipids by extracting and stabilizing membrane enzyme in functional states but appears to have milder effects on lipid order, broader compatibility with polyvalent cations, and less interference in far-UV spectra although it also appears to be less efficient at solubilization of some membrane and membrane proteins than SMA(2:1) copolymers [11], [17], [18].

Another chemically distinct series of polymethacrylate (PMA) copolymers were developed for making nanodiscs [19]. Although different in structure from SMA and its derivatives, these PMA copolymers can also fragment membranes.

A series of alkylated polyacrylic acid (PAA) copolymers with varying hydrophobic groups can fragment membranes into nanoparticles [20] but are again distinct in their composition from the copolymers invented here and lack certain properties such as fluorescence and affinity groups.

There remains a need for improved copolymers that offer the desired combinations of improved properties. The properties include reduced compositional heterogeneity, spontaneous and effective detergent-free solubilization of large and small membrane protein complexes by addition of the copolymer to cells, tissues or membranes, zwitterionic character or minimal net charge to offer broad compatibility with pH and polyvalent cations, minimized nonspecific interactions with antibody or protein sequences, maximized specific interactions of nanodisc-embedded protein with physiological ligands including lipids and metabolites, steric control near the backbone to reduce conformational dynamics, mild solubilizing activity so as to preserve multimeric membrane proteins and lipid complexes, the potential to incorporate of functional tags including fluorescent groups for convenient detection of copolymers and nanodiscs as well as the potential for the presence of affinity labels such as multiple imidazole groups or His, Flag, Strep, HA or Myc peptide tags for purification of membranes and memteins, and broad utility through integration of functional groups into alternating, semialternating as well as nonalternating copolymers including SMA, stilbene maleic acid and DIBMA-based copolymer systems.

For clarity, the closest prior art includes the following patent documents:

1. Tonge and Tighe, U.S. Pat. No. 6,436,905: "Lipid-containing compositions and uses thereof"
2. Rozema and Wakefield, U.S. Pat. No. 7,871,818 "Membrane active copolymers"
3. Tonge and Harper U.S. Pat. No. 8,623,414 "Compositions comprising a lipid and copolymer of styrene and maleic acids"
4. Dafforn, Overduin and Knowles, U.S. Pat. No.8,754, 168 "Solubilisation of membrane proteins"
5. Dafforn and Tyrynis-Thomas, U.S. Pat. No. 9,523,086 "Protein extraction"
6. Altenberg and Liang, US 2019/0062469 "Polymer-encases nanodiscs with improved buffer compatibility"
7. Ramamoorthy, Ramadugu, Ravula, Hardin and Cox, US 2019/0154698, "Polymer-based lipid nanodiscs and macrodiscs"

SUMMARY

Surprisingly, we have discovered that functional derivatives of maleimide (FDM) copolymers offer all the desired properties discussed above. FDM are scalable and extensible in terms of sidechains and copolymer length, and hence provide a significant improvement in performance and utility.

As the universe of possible copolymers is large, related copolymers have also been tested to examine if they form native nanodiscs and offer further advantages. Methyl-substituted stilbene maleic anhydrides contain alternating sidechains that consist of phenyl and maleic anhydride groups, and their synthesis and chemical properties have been studied by Richard Turner at Virginia Polytechnic Institute [21]. Surprisingly, we discovered that such stilbene-based copolymers, which are structurally and functionally similar to alternating SMA copolymers, can also be activated into maleic acid forms to directly solubilize biological membranes and form highly ordered nanodiscs.

The invention therefore provides an amphiphilic copolymer comprising Formula $I^A$ or $I^B$ (where $I^B$ is a derivative of $I^A$), or a combination thereof:

($I^A$)

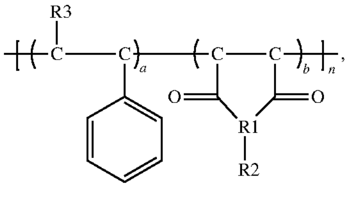

-continued ($I^B$)

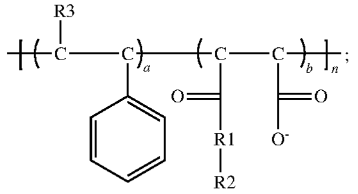

wherein

Formula $I^B$ can exist in an aqueous medium wherein the ionic formula has a monovalent counterion such as $Na^+$, $K^+$ or $NH_4^+$ to compensate for the negative charge;

R1 is a nitrogen in Formula $I^A$ and in Formula $1^B$ R1 is either —NH—or, in the case where R3 is a phenyl group, the R1 is an oxygen (O) and R2 is a H;

R2 is a polar group or ($C_1$-$C_{12}$)alkyl;

wherein when R2 is a polar group, R1 and R2 taken together form a histamine, an alkylamine oxide, amino alkanediol, alkyl amine, alkanolamine, quaternary amine, or an alkyl ester of an amino acid residue;

R3 is a hydrogen, unsubstituted phenyl, or phenyl substituted by one or more polar or non-polar substituents at the ortho, meta or para positions;

provided that when R3 is a hydrogen, R2 is not an alkylamine oxide, ($C_1$-$C_3$)alkyl, a quaternary amine, or an alkanolamine; and the monomer moieties labeled a and b are in a substantially alternating, largely alternating, or semialternating copolymer arrangement in the length of the copolymer backbone, and wherein the phenyl ring shown in subunits a optionally have one or more alkyl, halo, —OH, or —$NH_2$ substituents, or a combination thereof, in place of one or more hydrogen atoms of the phenyl ring.

In another embodiment, the invention provides a disc-shaped nanoparticle comprising an amphiphilic copolymer and biological material comprising complexes of hydrophobic molecules;

wherein a plurality of the amphiphilic copolymers forms a nanodisc having a hydrophilic outer surface, a regularized annulus, and a hydrophobic inner core;

wherein the biological material is held in an annulus of the nanodisc such that the biological properties of the biological material are maintained;

wherein the amphiphilic copolymer comprising Formula IA or IB (where $I^B$ is formed from of $I^A$), or a combination thereof:

($I^A$)

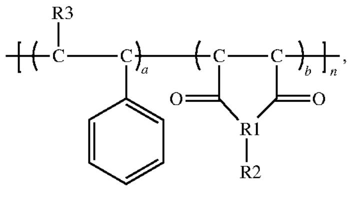

-continued (I^B)

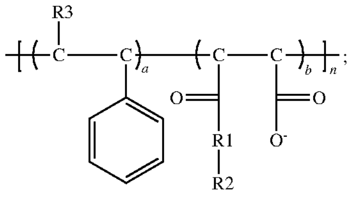

wherein

Formula $I^B$ can exist in an aqueous medium wherein the ionic formula has a monovalent counterion such as $Na^+$, $K^+$ or $$NH_4^+$$

to compensate for the negative charge;

R1 is a nitrogen in Formula $I^A$ and R1 is —NH— or O in Formula $I^B$;

R2 is a polar group in Formula $I^A$ or R2 is a polar group or H in Formula $I^B$;

wherein when R1 is nitrogen or —NH— and R2 is a polar group, R1 and R2 taken together form a histamine, an alkylamine oxide, an amino alkanediol, an alkyl amine, an alkanolamine, a quaternary amine, or an alkyl ester of an amino acid residue;

R3 is a hydrogen, or phenyl optionally alkyl substituted at the meta, para or ortho positions;

provided that when R1 is O and R2 is hydrogen, R3 is a (optionally substituted) phenyl;

and provided that when R1 and R2 taken together form an alkanolamine or quaternary amine, R3 is a (optionally substituted) phenyl; and the monomer moieties labeled a and b are in a substantially alternating, largely alternating, or semialternating copolymer arrangement in the length of the copolymer backbone;

wherein the biological material comprises lipids and proteins derived from bacterial, mammalian, animal, fungal, or plant cells or tissues.

Also disclosed herein is a solubilization process which includes adding the copolymer to a sample of a tissue, cells or membranes, a purification process which could include metal affinity resins or size exclusion columns, a copolymer liberation process to remove copolymers from nanodiscs by altering the pH or introducing polyvalent counterions or oppositely charged copolymers, a screening process, an assaying process, and the use of the copolymers and disc-shaped nanoparticles for manufacturing a hydrophobic agent such as a delivery nanoparticle, drug molecule, drug formulation, drug development agent, drug screening candidate, membrane protein ligand, or vaccine composition.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention described herein.

The immunoblot (probed for His tags) shows amount of PagP protein monomer and multimer states solubilized directly from the outer membranes using each copolymer. The plasmid pETCrcAH was used to express a C-terminal $His_6$ tagged PagP protein, which includes the native 22 residue signal peptide that is cleaved during outer membrane targeting, after induction with isopropyl-β-D-thiogalactopyranoside in *E. coli* BL21(DE3)pLysE grown in broth at 37° C. (30). The outer membranes from French Press lysates of bacterial cells were isolated by ultracentrifugation of the crude membrane fraction at 195,000xg (Ti45 rotor, Beckman) in 55% (w/v) sucrose (in Tris 10 mM, pH 8). The outer membranes were then incubated with 2% (w/v) of each copolymer in Tris 10 mM pH 8, 100 mM NaCl, 5% (v/v) glycerol for 30 min at 37 ° C. followed by an overnight incubation at 4 ° C.

Figure 11:
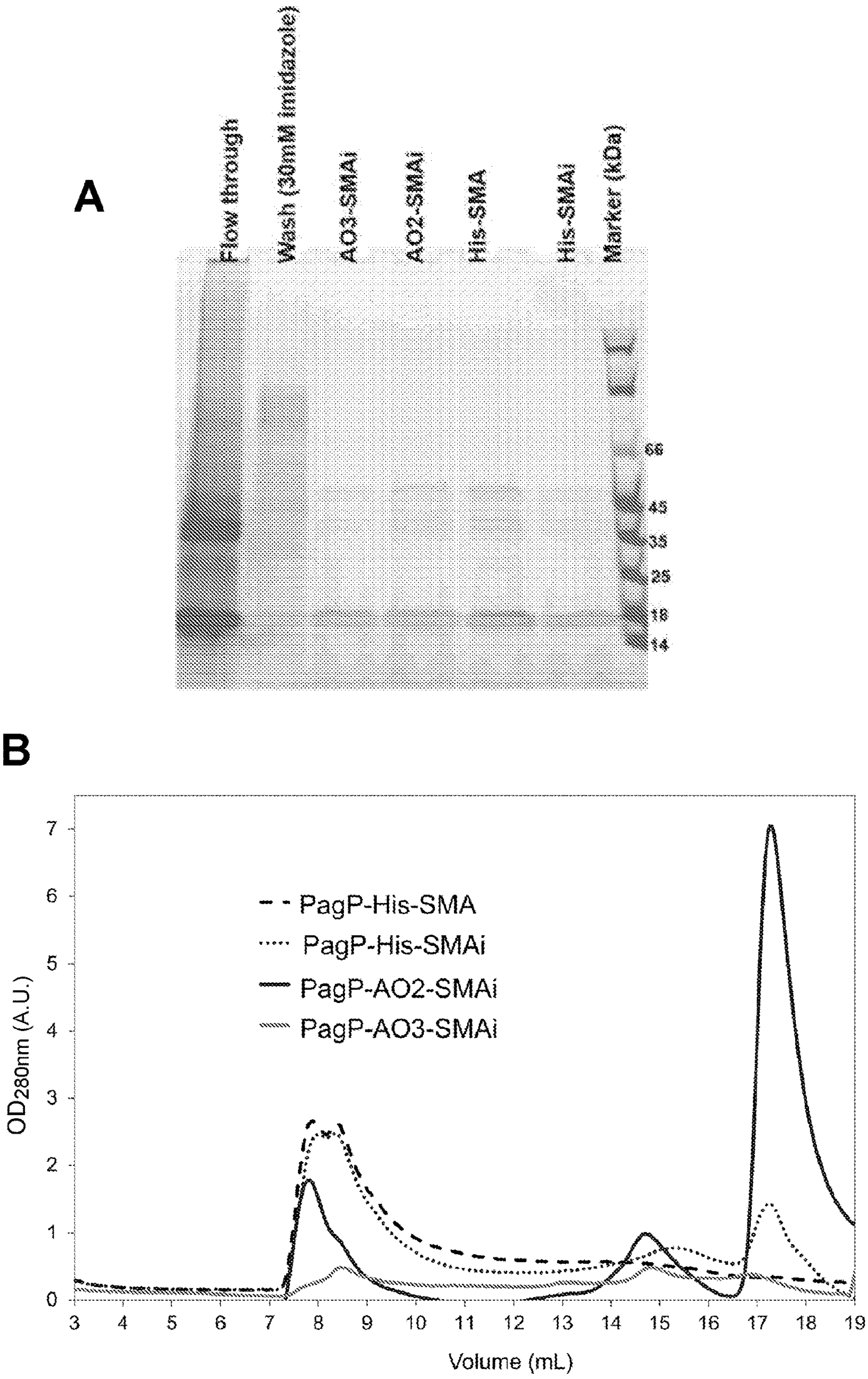

FIG. 11: (A) Detergent-free solubilization and purification of His-tagged PagP protein from the outer membrane of *E. coli* using AO-SMAi (C2 and C3) and SMA-His (open and close forms) and Ni-NTA affinity columns. The outer membrane was isolated by ultracentrifugation of the crude membrane at 195,00033 g (Ti45 rotor, Beckman) in 55% (w/v) sucrose (in Tris 10 mM, pH 8). The isolated membrane was then incubated with 2% (w/v) of each copolymer in Tris 10 mM pH 8, 100 mM NaCl, 5% (v/v) glycerol for 30 min at 37° C. followed by an overnight incubation at 4° C. The suspension was centrifuged at 58,000×g and the soluble PagP discs in the super-natant were purified using a HisPur Ni-NTA resin (Thermo Scientific™). (B) Fractions containing PagP were eluted with 250 mM imidazole, pooled, and used for purification over a Sephadex® 200 10/300 GL column (GE). Size exclusion chromatography (SEC) profile of PagP nanodiscs composed of different FDM copolymers. Lines indicate the fractions that contain His-tagged PagP nanodiscs, as confirmed with Western blotting. Fractions containing PagP were eluted with 250 mM imidazole, pooled, and separated over a Sephadex 200 10/300 GL column (GE).

Figure 12:
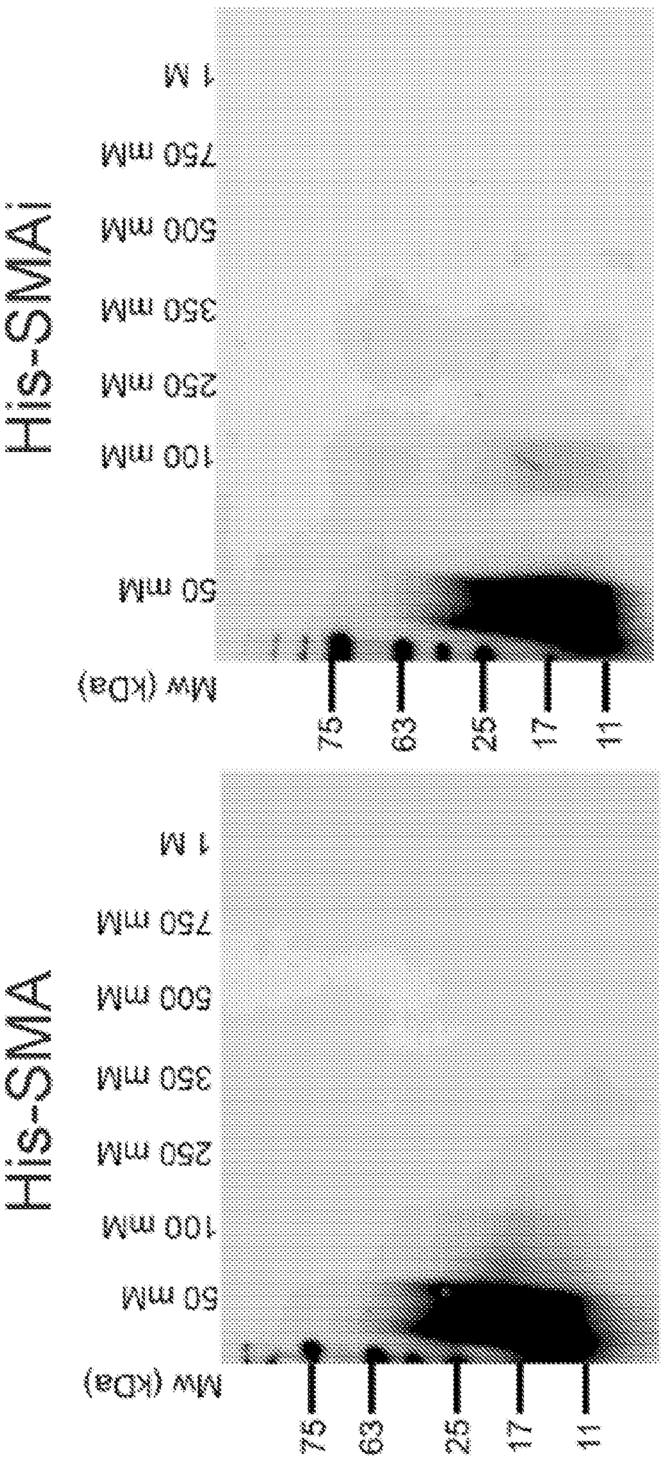

FIG. 12: Interaction of His-SMA copolymers with Ni-NTA resin columns. The copolymers were eluted from the column at 50 mM imidazole and detected on the immunoblot via anti histamine antibody. This provides a basis for purifying nanodiscs formed by His-SMA copolymers using antibodies that bind FDM copolymers and resulting nanodiscs.

Figure 13:
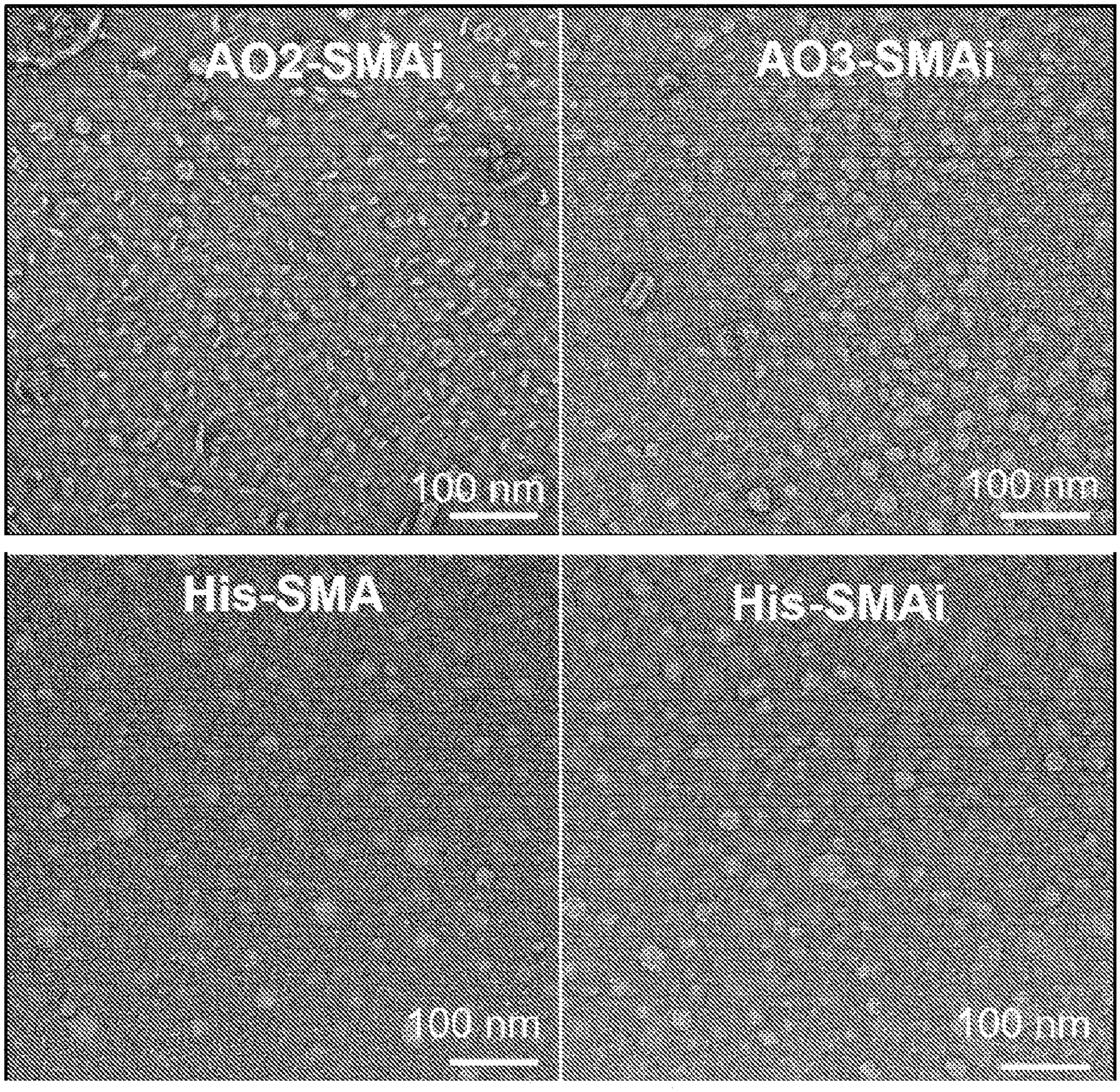

FIG. 13: Negative stain electron micrographs of nanodiscs of PagP- containing *E. coli* outer membrane solubilized in 1.5% (w/v) AO-SMAi SMAOs and SMA-His copolymers. The diameters of discs are between of 15-25 nm. The scale bar is 100 nm. The data was collected on carbon-coated copper grids with a 400 nm-mesh (Electron Microscopy Science, USA) which were glow charged using an Pelco Easy Glow 100 × glow discharge unit (Ted Pella Inc, USA) for 30 seconds. Microliter amounts of either the NTA-column-purified PagP or fractions from size exclusion chromatography were adsorbed on the grids for 1 min. The grids were washed three times (3×50 μL) with filtered de-ionized water and stained with filtered 2% (w/v) uranyl acetate. Excess stain was removed using a filter paper and the grids were air-dried for at least two hours before TEM imaging. EM micrographs were collected using a Tecnai G20 transmission electron microscope (FEI Eindhoven, NL; an acceleration voltage of 200 kV), which is equipped with an Eagle 4 k×4 k CCD camera (FEI).

Figure 14:
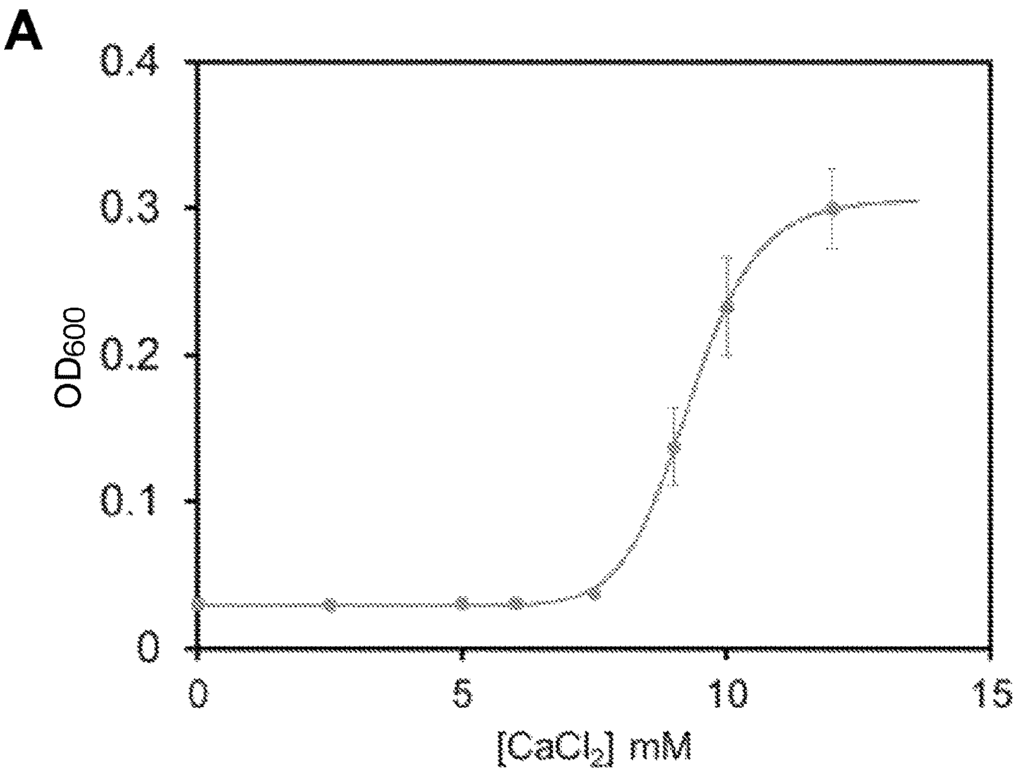
Figure 14:
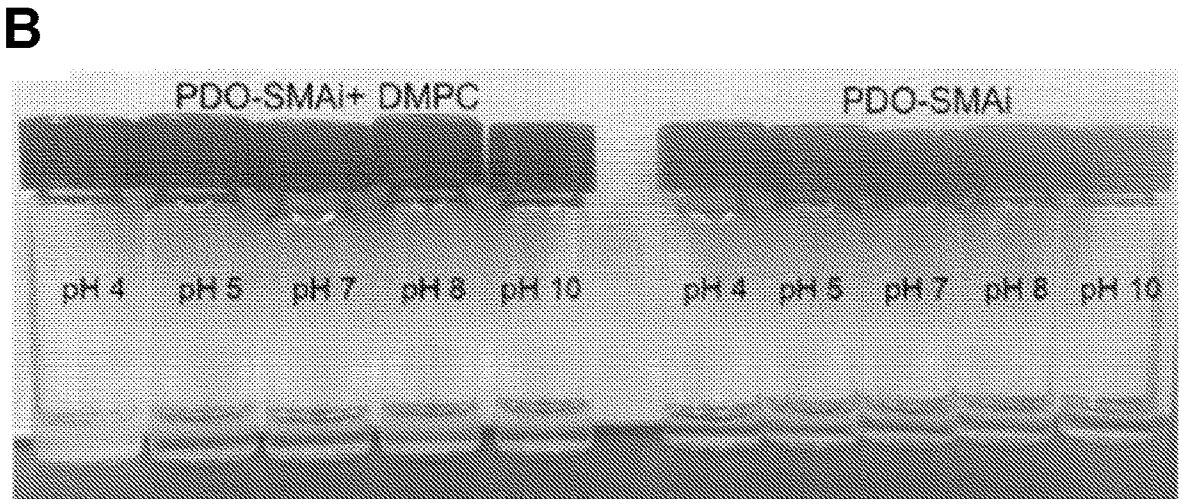

FIG. 14. Solubility profiles of PDO-SMAi. (A) Calcium tolerances of copolymer 8 (1% w/v solution) were quantified by optical density at 600 nm. (B) The solubility of copolymer 8 at pH levels from 5 to 10 are shown, where each solution is clear (5 tubes on right), as are the abilities to clarify suspensions of vesicles formed by DMPC, where at pH4 the solution is slightly turbid but clear at all pH 5 or greater (5 tubes on left). The protocol was as described above including in FIG. 6.

Figure 15:
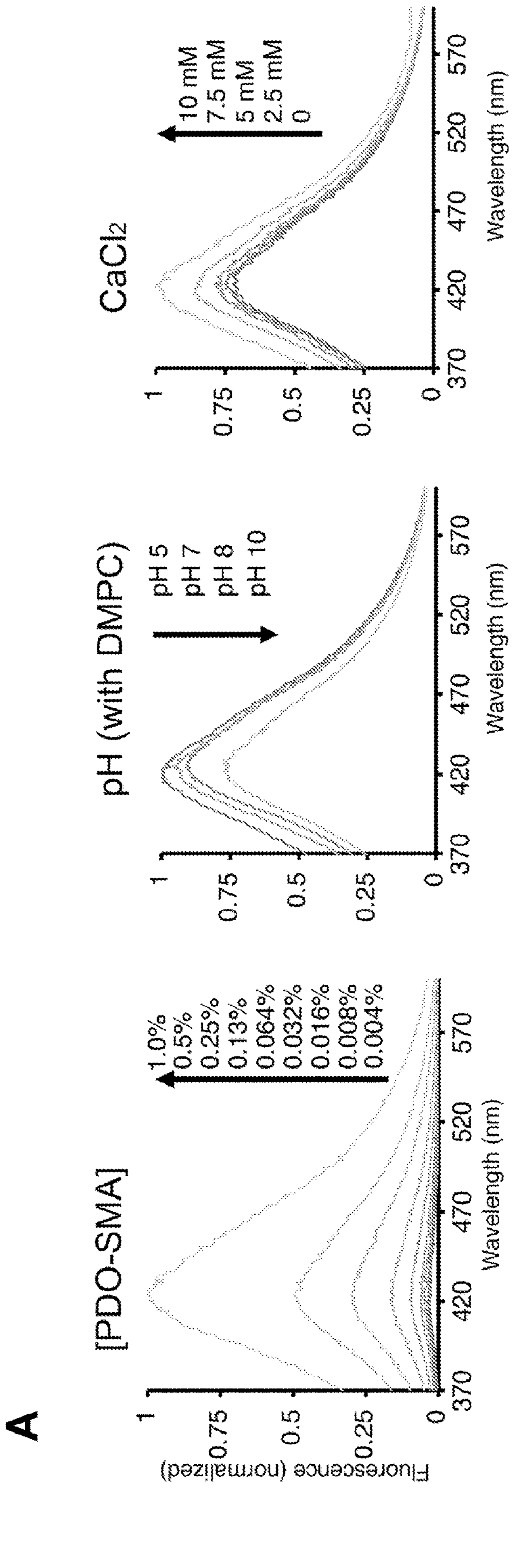
Figure 15:
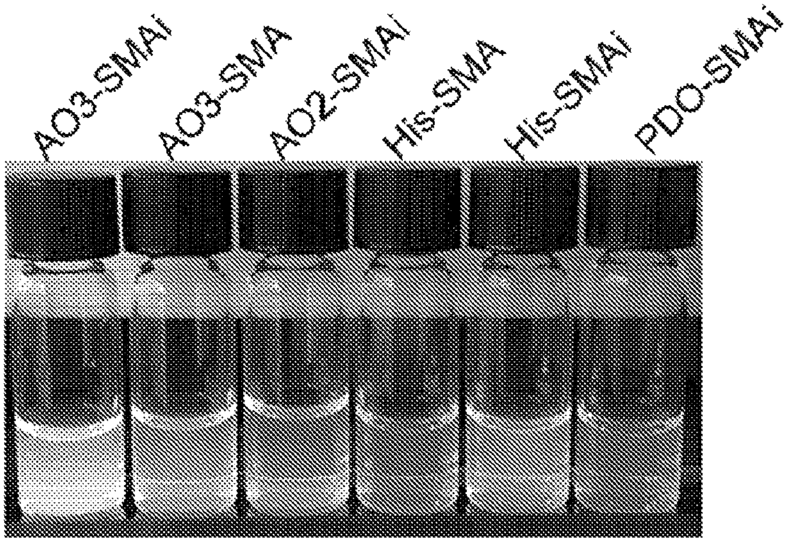

FIG. 15: Fluorescence of PDO-SMAi. (A) Spectra under different copolymer concentrations, pH ranges (5-10), $CaCl_2$ concentrations are shown. (B) Vials of each indicated copolymer (1 w/v) display fluorescence under 350 UV light.

Figure 16:
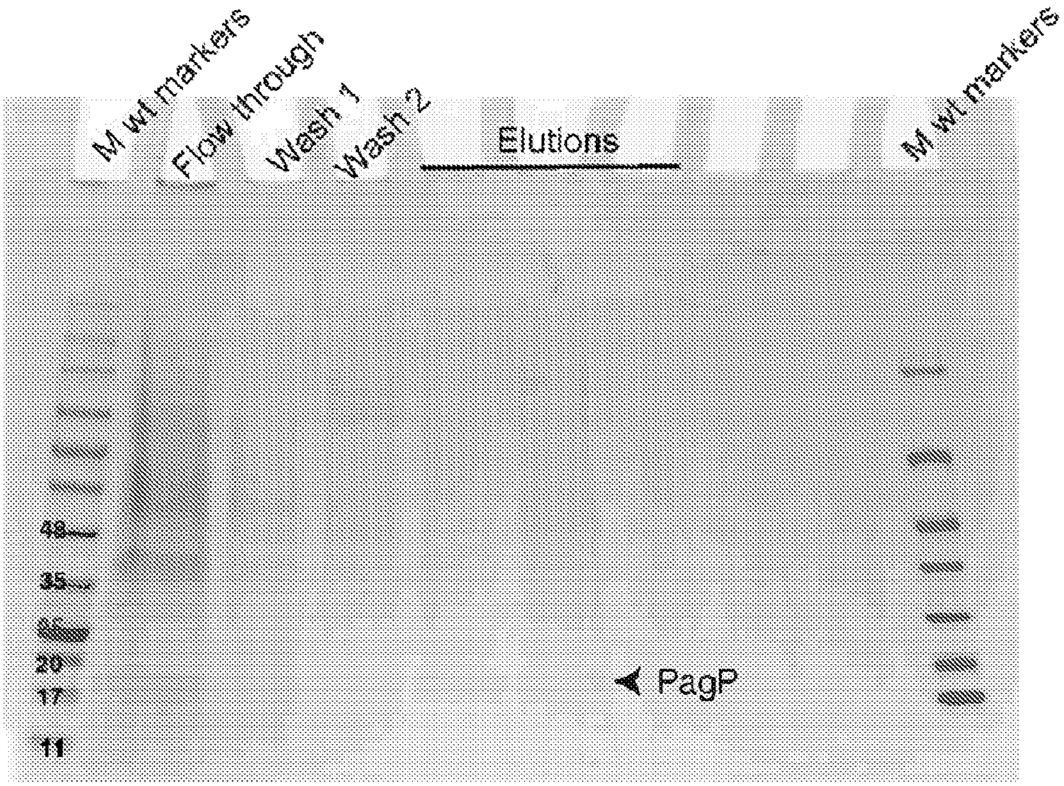

FIG. 16: The solubilization of PagP protein from the outer membrane of *E. coli*, prepared as described above, using PDO-SMAi is shown. The stain-free SDS-PAGE gel shows the partially purified PagP protein prepared using this FDM copolymer.

Figure 17:
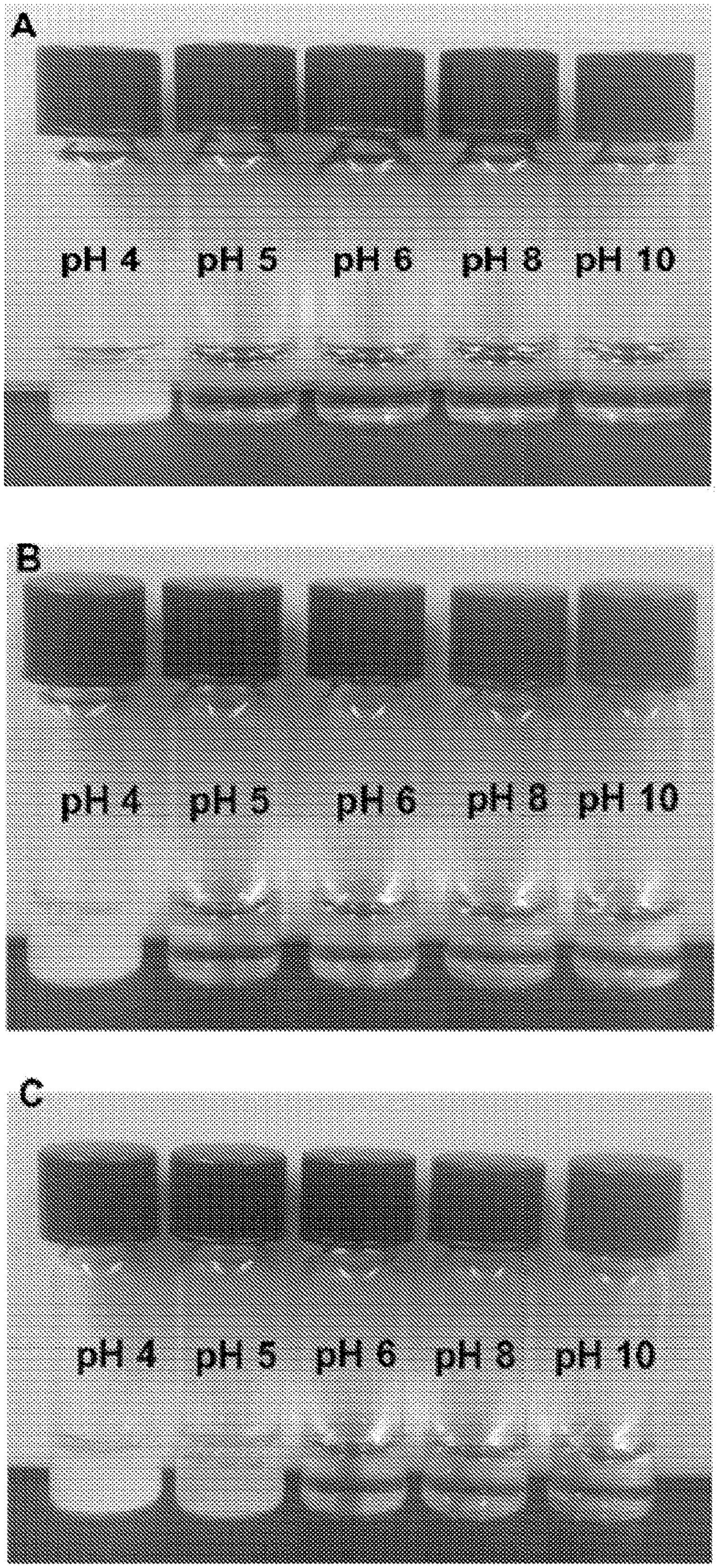
Figure 17:
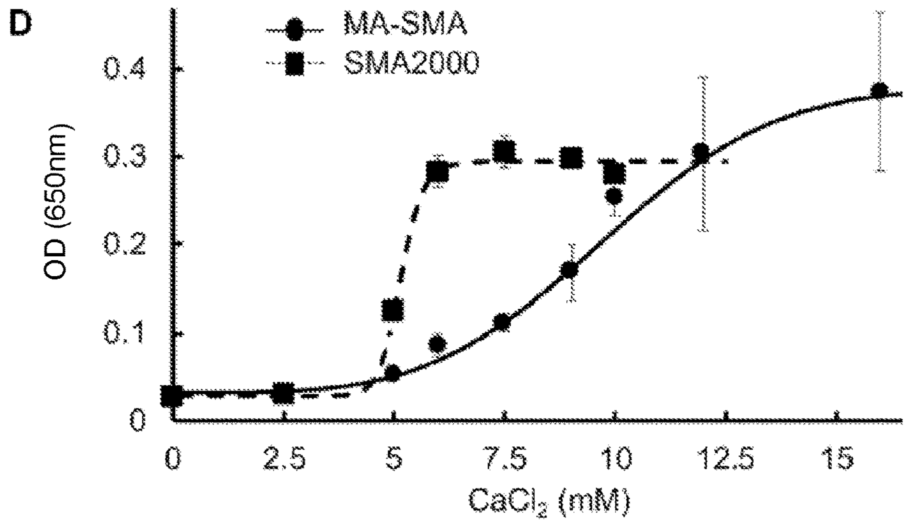
Figure 17:
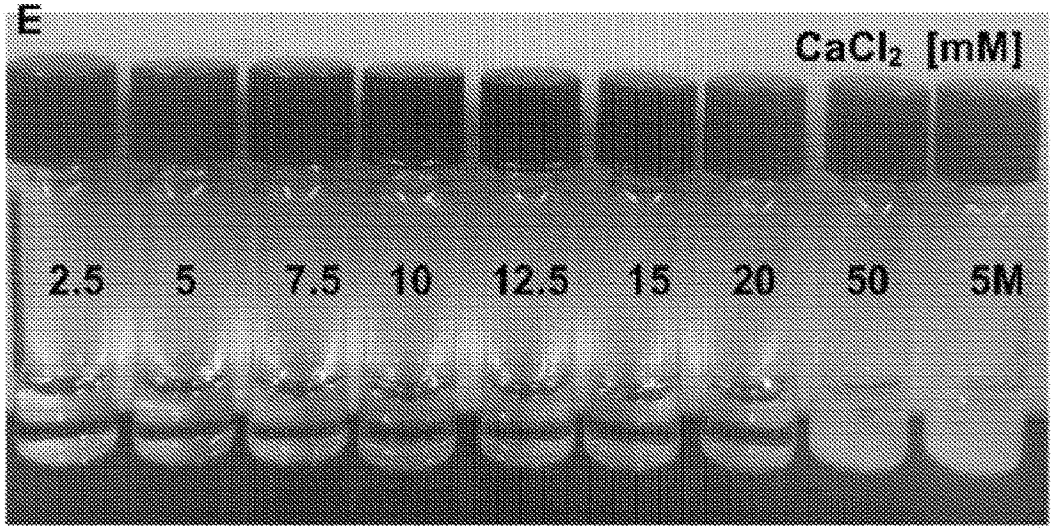
Figure 17:
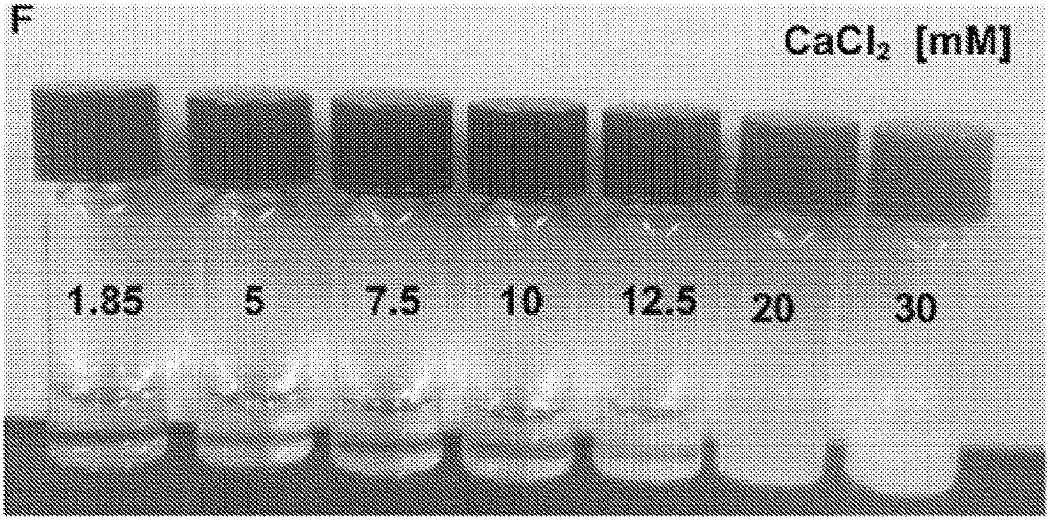
Figure 17:
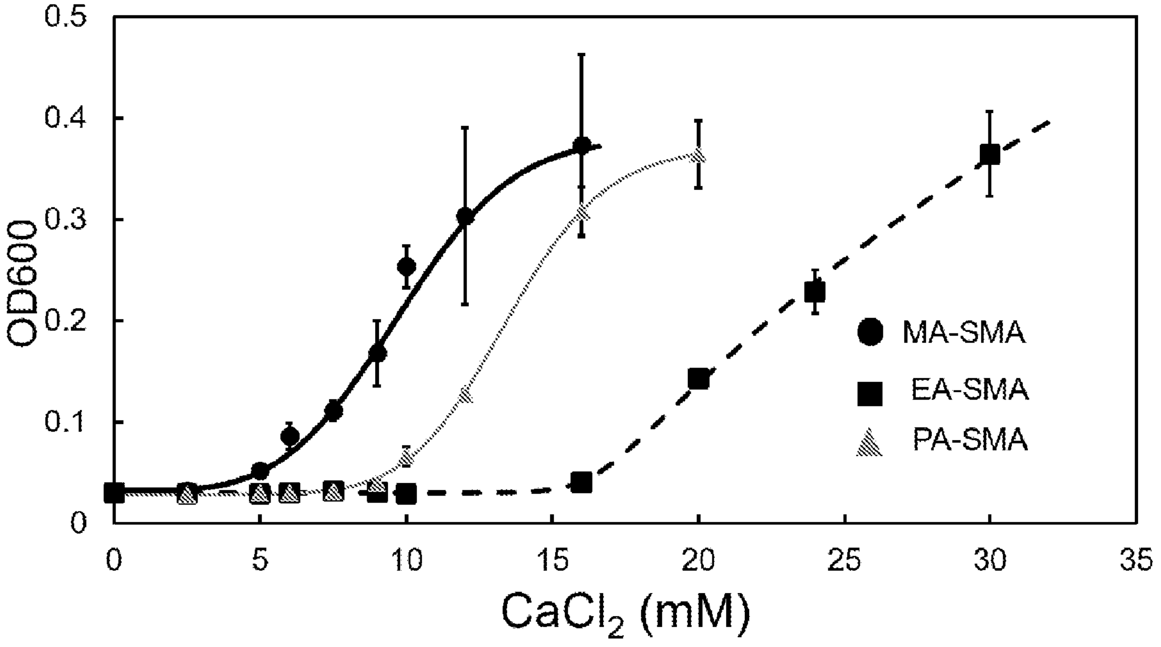

FIG. 17: Membrane solubilization by MA-SMA, EA-SMA and PA-SMA. The pH-dependent solubility of MA-SMA (A), EA-SMA (B) and PA-SMA (C) is shown by the clarity of solutions at pH values between 5-10 while they precipitate at pH 4. The more hydrophobic PA-SMA also begins to precipitate at pH 5. The calcium-dependent solubility of MA-SMA (D), EA-SMA (E) and PA-SMA (F) is shown by the optical density at 600 nm (D) and turbidity of solutions (E, F). MA-SMA retains solubility at higher calcium concentrations than SMA2000 (Sartomer) based on the midpoint of 5 vs 10 mM $CaCl_2$ (D). (G) Curves show the calcium-dependent turbidity of the MA-SMA, EA-SMA and PA-SMA with midpoints at ~10, 25 and 13 mM $CaCl_2$, respectively.

Figure 18:
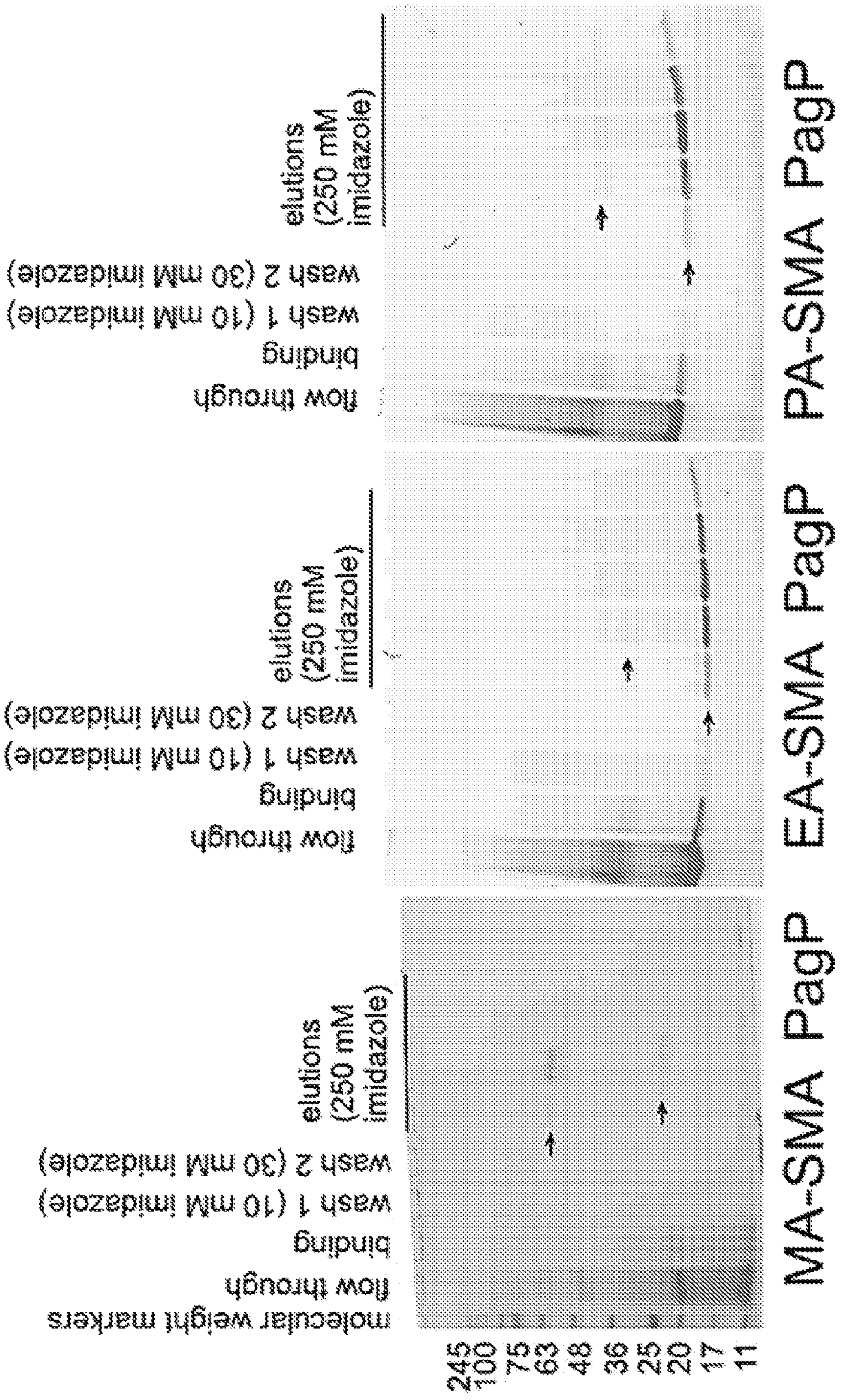

FIG. 18: Solubilization of PagP from *E. coli* using MA-SMA, EA-SMA and PA-SMA. Recombinant $(His)_6$-tagged PagP was overexpressed in the outer membrane of *E.coli* BL21(DE3) pLysS, the outer membrane fraction was collected (from 6 L LB culture) and used for purification of PagP as described above.

The membrane fraction was incubated with 2% w/v concentration of each alkylamine polymers in Tris 10 mM, NaCl 100 mM and 5% v/v glycerol (buffer A). Membrane lysates were further used for purification using a 5 mL HisTrap-HP column (GE). Buffer A supplemented with 10 mM and 30 mM imidazole were used as washing buffers 1 and 2, respectively, and PagP-nanodiscs were eluted with 250 mM imidazole (in buffer A). Samples from each step of purification were collected, mixed with sample buffer (2X, BioRad) and heated for 10 mins at 100° C. and then analyzed on a 12% precast stain-free SDS-PAGE (BioRad). SDS-PAGE gels were imaged either after staining with Coomassie blue (SMA(1:1)-Mt) or stain-free (SMA(1:1)-Et and SMA(1:1)-Pr) on a Gel Doc EZ system (BioRad). The Coomassie blue stained SDS-PAGE gels show PagP extracted and partially purified from the outer *E. col* membrane. The lanes of each gel show molecular weight markers, flow through (FT), Ni-NTA bound, two washes with 10 and 30 mM imidazole and five elutions with 250 mM imidazole from left to right. Arrows designate the location of monomer and dimer species on SDS-PAGE.

Figure 19:
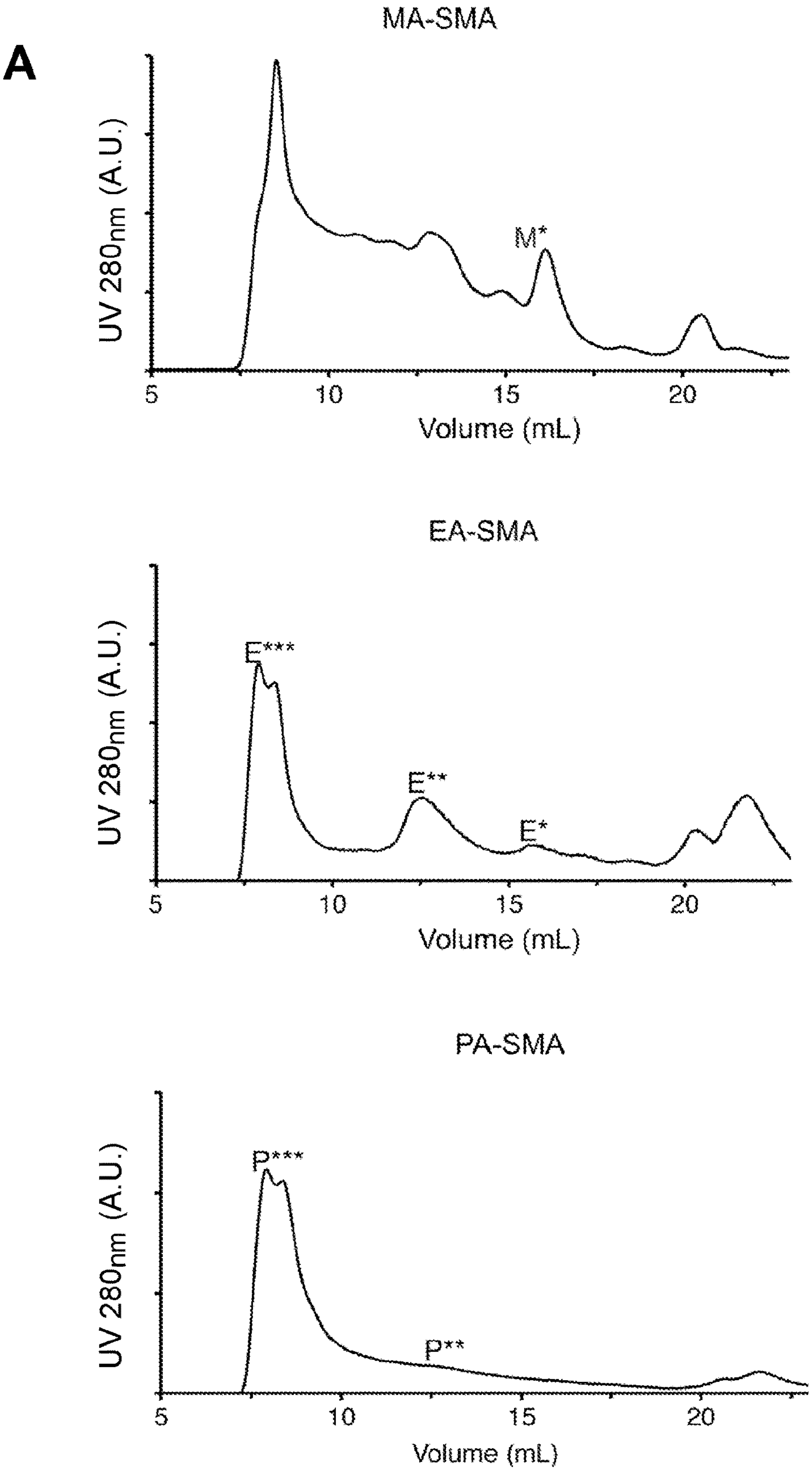
Figure 19:
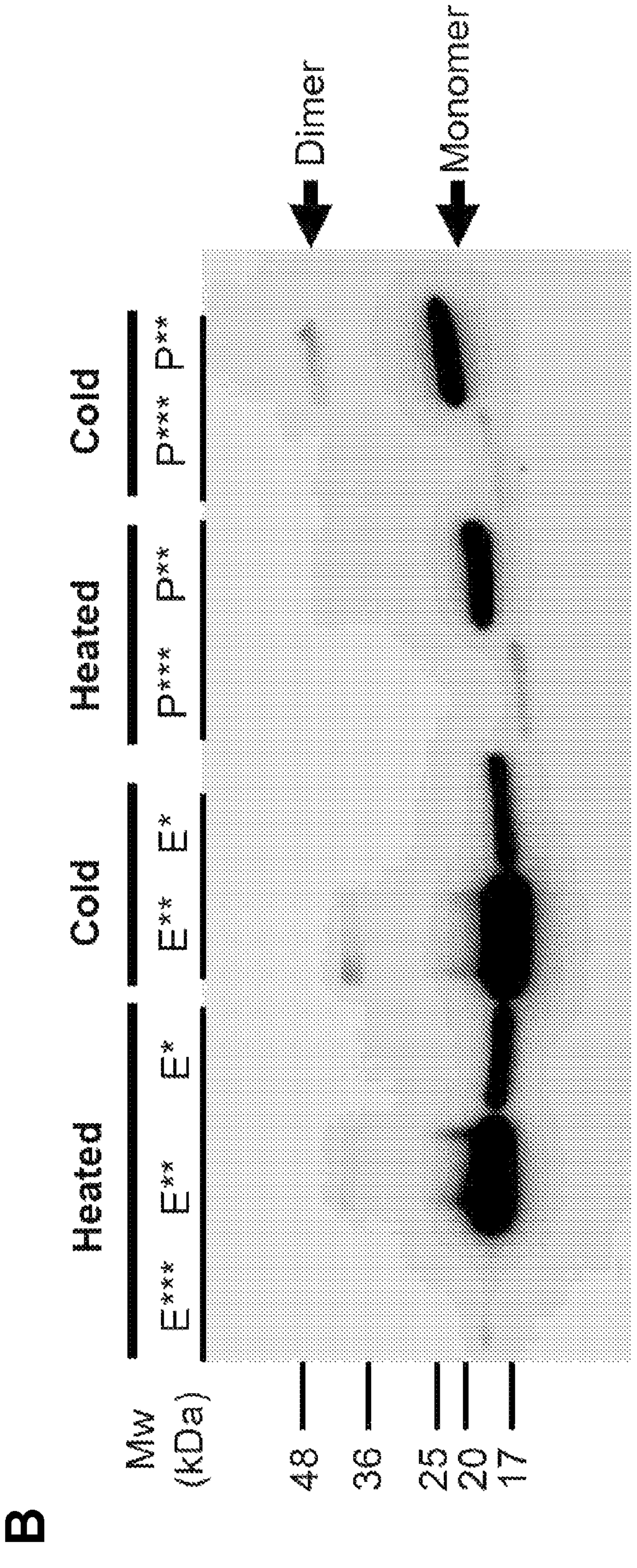

FIG. 19: A. Purification of PagP native nanodiscs composed of MA-SMA, EA-SMA and PA-SMA. Fractions with the highest amount of PagP protein were used for size exclusion chromatography on a Superdex® 200 10/300 GL column (GE) in buffer A. Collected fractions were analyzed by Western blotting on a PVDF membrane (BioRad) using His-Prob (Pierce). The bands were visualized using Clarity™- ECL substrate (BioRad). Unheated (cold) samples refer to those incubated with sample buffer at room temperature for 10 min. SEC profiles include asterisks to indicate the fractions that contain His-tagged PagP nanodiscs based on Western blotting. B. To identify the oligomeric states of PagP (see arrows) in each fraction, Western blotting of the unheated (native) and heated (at 100° C.) SEC fractions (as marked on B) were compared.

Figure 20:
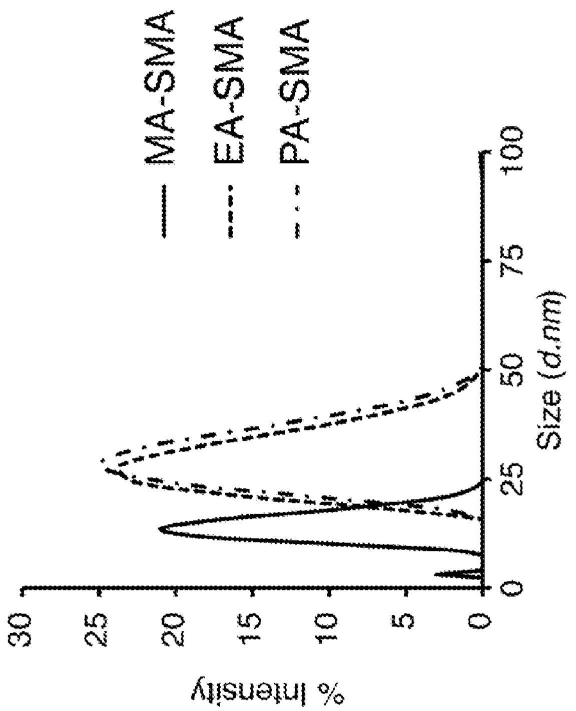
Figure 20:
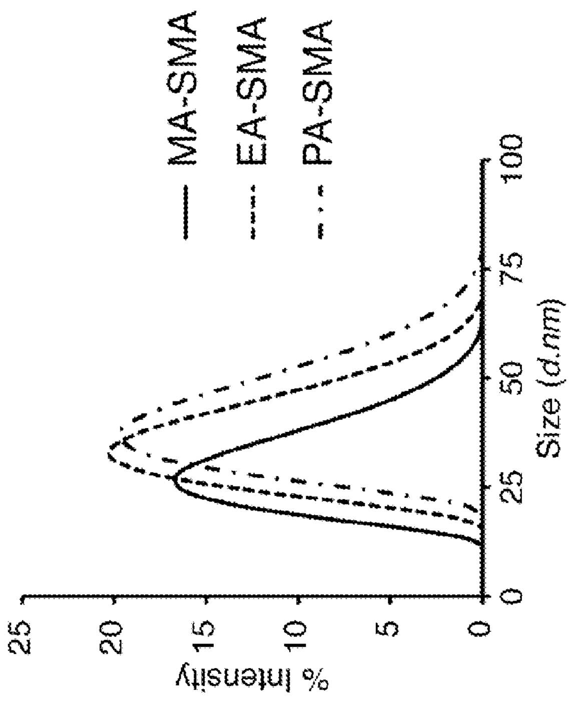

FIG. 20: Dynamic light scattering measurements showing the diameters of nanodiscs formed by MA-SMA, EA-SMA and PA-SMA solubilized DMPC vesicles. Unilamellar vesicles of DMPC (3.5 mM, 135 nm in diameter) were prepared in Tris 10 mM, NaCl 100 mM by sonication, and mixed with different amount of stock solution of polymers (in water, filtered) and incubated overnight at room temperature. The size distributions of lipid nanodiscs were analyzed by DLS on a Zetasizer Nano ZSP (Malvern Panalytical, UK) using reusable 3 mm cuvettes. Each measurement was read three times (each with 12 scan average) and for at least three independent samples. Data were analyzed by Zetasizer software version 7.12. The nanodisc diameters are shown in nanometers, with 0.6% w/v (left) and 1% w/v (right) copolymer concentrations generally yielding optimal disc sizes and homogeneities.

Figure 21:
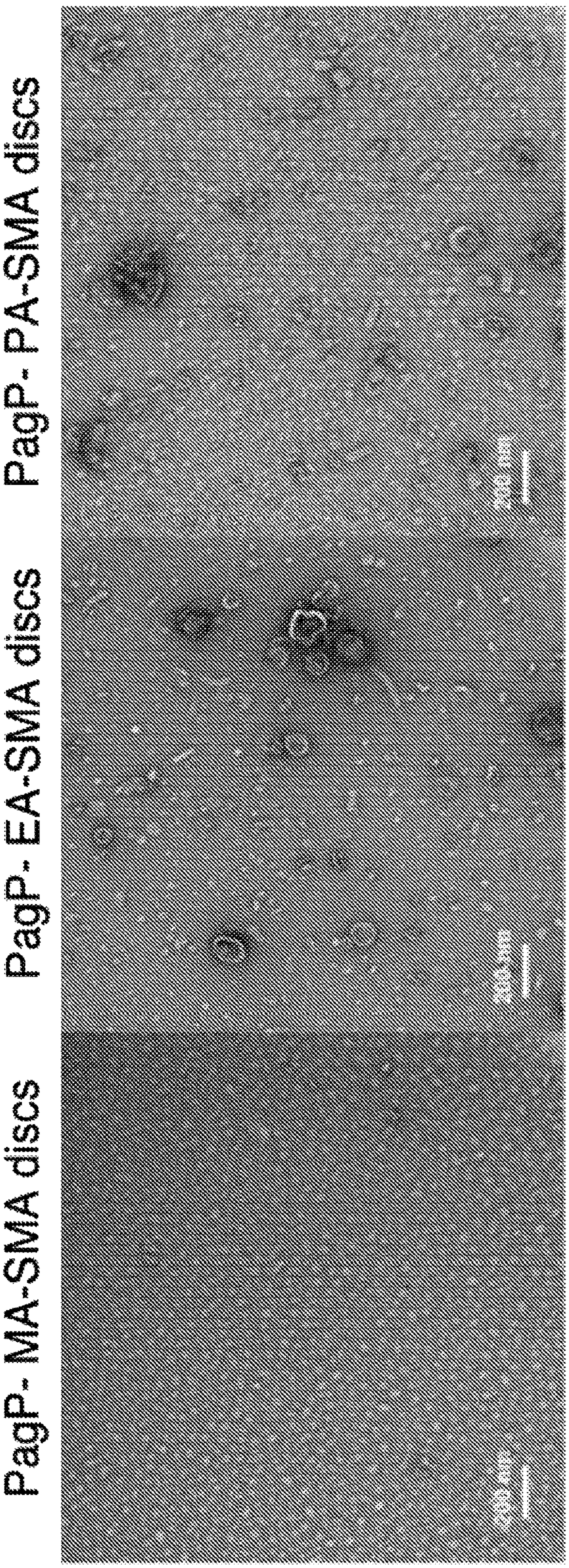

FIG. 21: Native nanodiscs containing PagP protein from *E. col* outer membrane solubilized by MA-SMA, EA-SMA and PA-SMA and resolved in TEM images. The 100, 200 and 100 nm bars below each image show the respective image scales. The nanodiscs had been partially purified by Ni-NTA and size exclusion chromatography. Larger particles represent lipid vesicles and fragments thereof. Microliter amounts of fresh size exclusion chromatography (SEC) fractions (M*, E and P) were loaded on carbon-coated copper grids (400 nm mesh, already glow charged for 30 sec), washed three times with deionized water and stained with Uranyl acetate (2% w/v, filtered). Grids were dried for at least 2 hours prior to imaging on a Tecnai G20 transmission electron microscope (FEI Eindhoven, NL; an acceleration voltage of 200 kV), that is equipped with an Eagle 4 k×4 k CCD camera (FEI).

Figure 22:
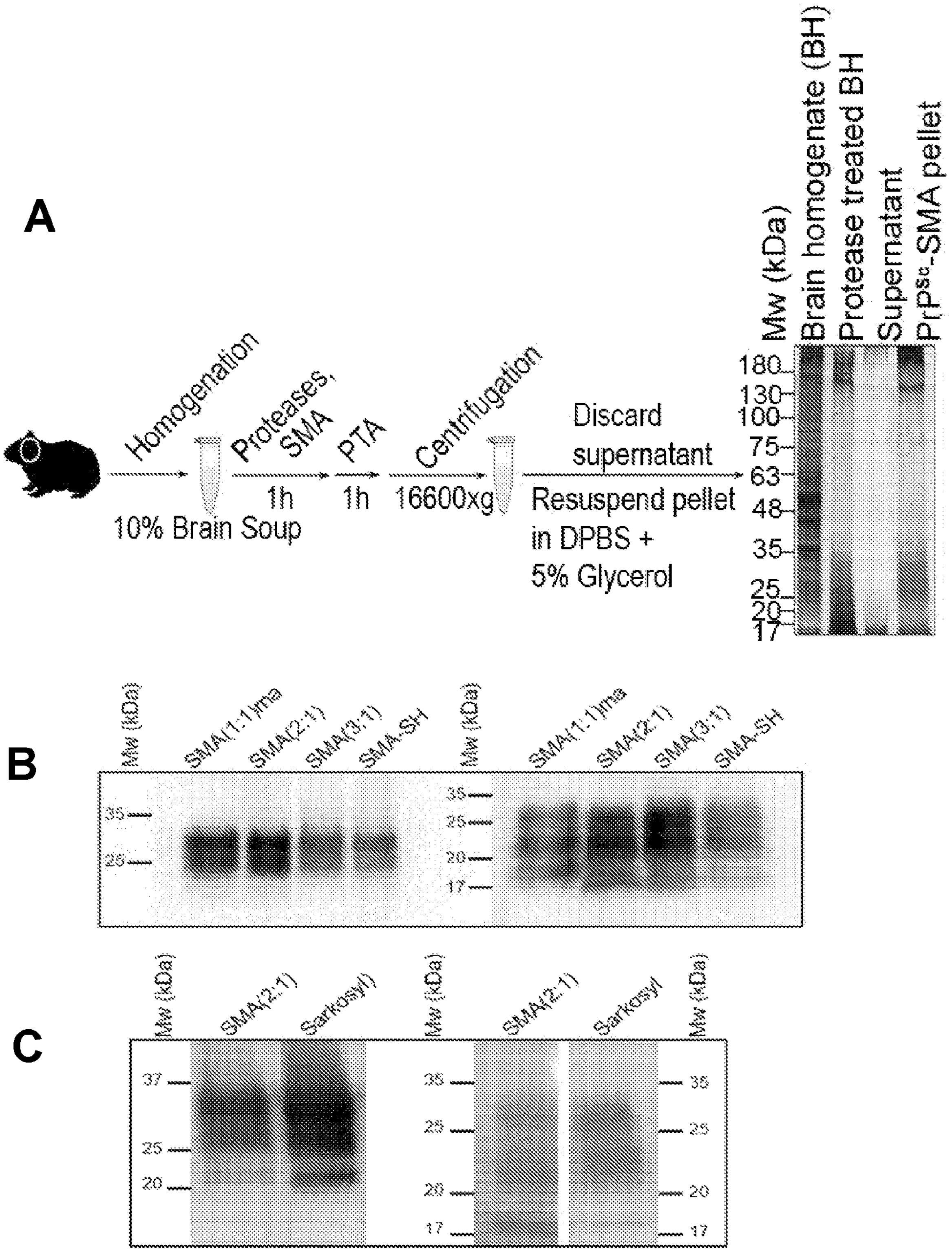

FIG. 22: (A) Schematic description of detergent-free isolation of protease resistant prion from the infected brain tissues. Brain homogenates (20% w/v) were generated from clinically ill Hyper strain-infected Syrian hamster brains and RML-infected FVB mouse brains and prepared in Dulbecco's phosphate-buffered saline plus 5% glycerol, mixed with 8% (w/v) copolymer stock solution to a final concentration of 1% (w/v) and Pronase E (Sigma). Each mixture was then incubated at 37° C. for 30 min after which the protease was inactivated by EDTA addition. Sodium phosphotungstic acid (PTA, 200 μL of 10% w/v, pH 7.2) was added and the mixtures were incubated for one hour at 37° C. The solutions were centrifuged at 16,500×g, and the pellets were resuspended in DPBS and 5% (v/v) glycerol and stored at −20° C. for later assays. (B) Immunoblots of SMA-purified $PrP^{Sc}$ from Syrian hyper hamsters and FVB-RML mice using anti $Prp^{Sc}$ primary antibody, showing similar molecular weights and glycosylation patterns for the SMA-purified $PrP^{Sc}$ preparation compared to samples purified with sarkosyl. (C) Silver-stained SDS-PAGE showing the amount of protein including in SMA-$PrP^{Sc}$ complexes collected from Syrian hyper hamsters after phosphotungstic acid (PTA)-based purification.

Figure 23:
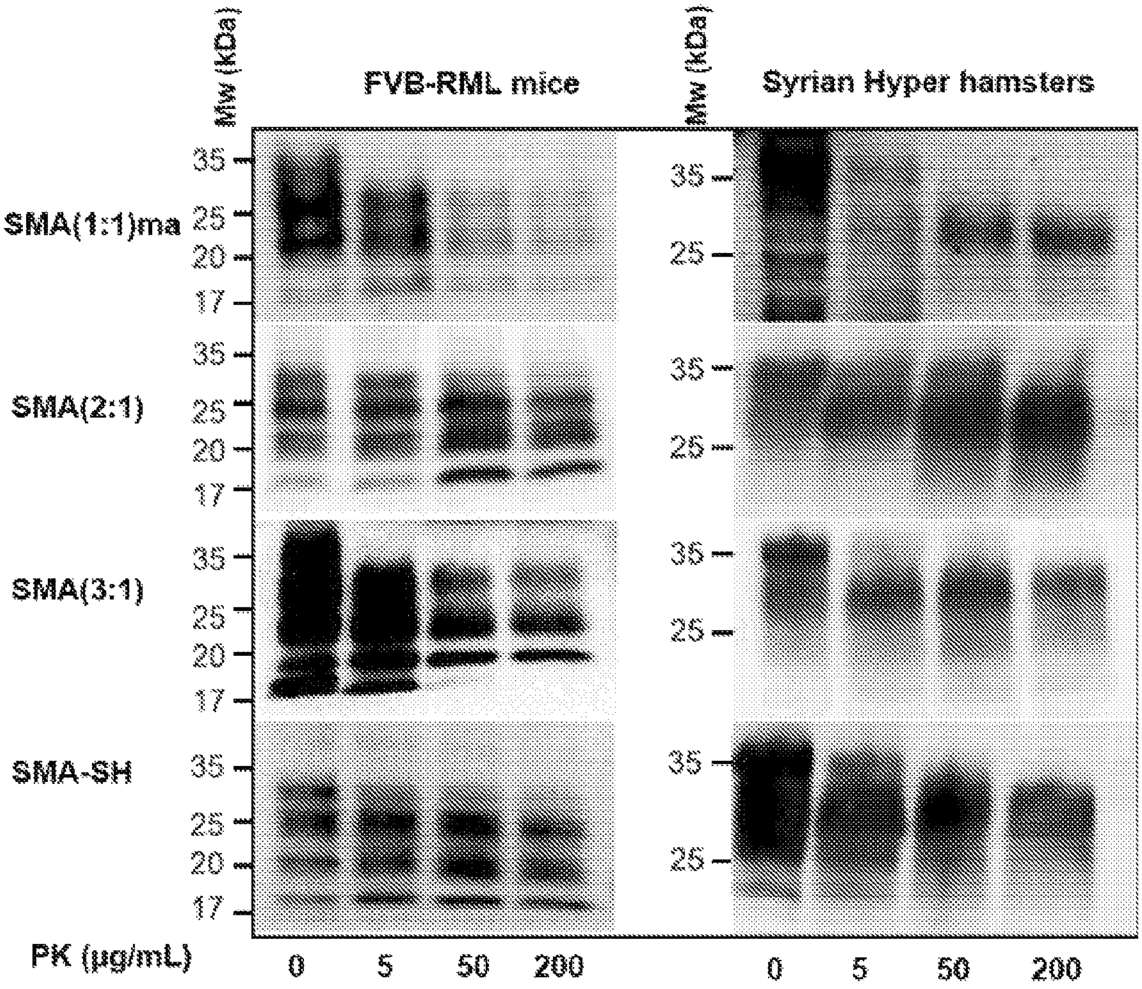

FIG. 23: Post-mortem brains of SMA-$PrP^{Sc}$ infected Syrian hamsters and SMA-$PrP^{Sc}$ infected FVB-RML mice were subjected to digestion with Proteinase K (PK). PK-digestion patterns of all samples confirm the presence of protease resistant scrapie forms.

Figure 24:
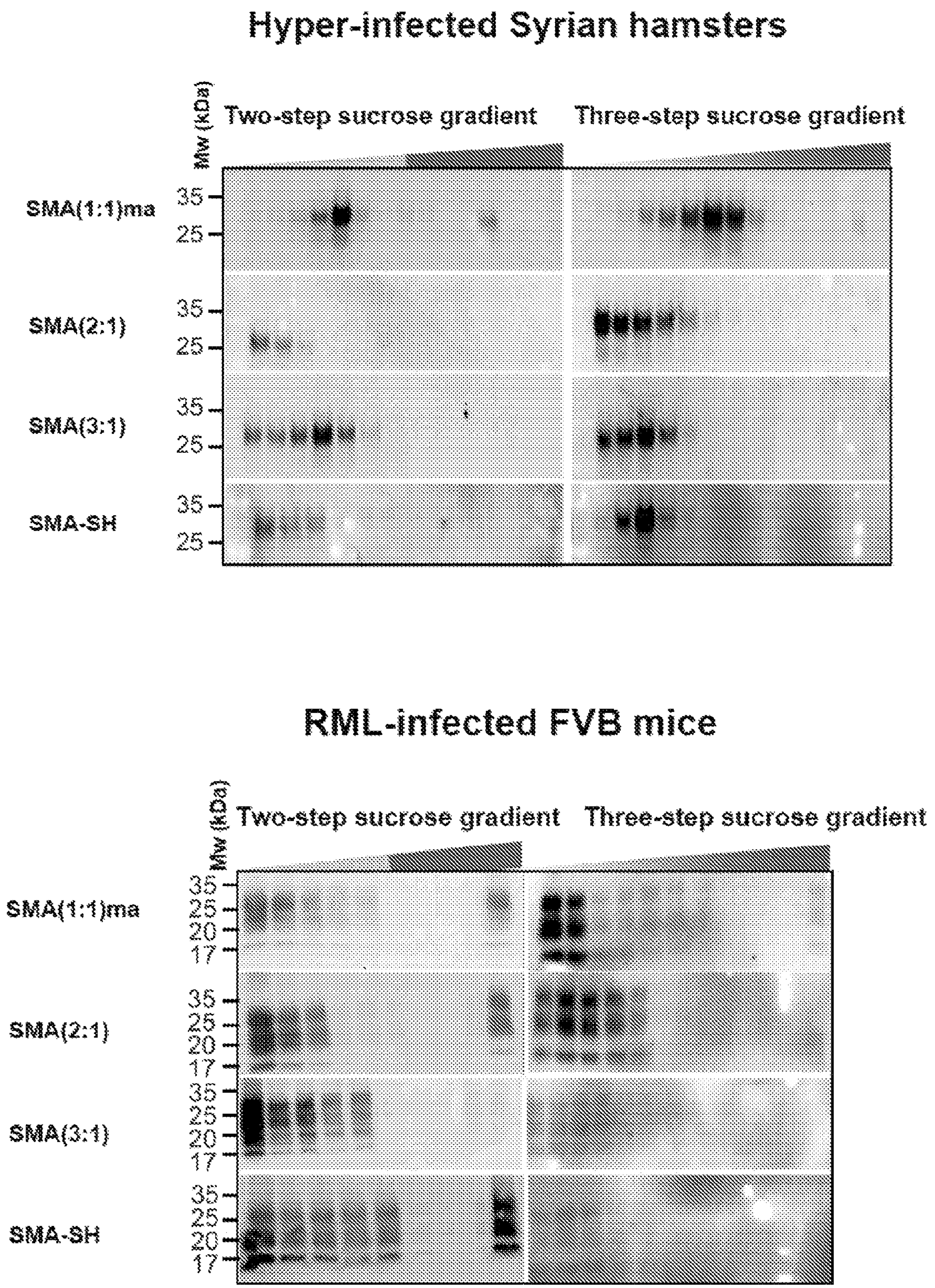

FIG. 24: Protease treated SMA-$PrP^{Sc}$ particles isolated from Syrian hamsters and FVB-RML mice were separated according to their densities using two-step sucrose gradient (40 and 80%) and three-step (40, 55 and 80%) sucrose velocity ultracentrifugations, with fractions collected from the tops to the bottoms of tubes for immunoblotting. Sucrose gradients in DPBS were prepared in 3.5 mL Beckman ultracentrifuge tubes in order to resolve prion multimers. Three independent sets of SMA-purified samples were overlaid on top of each gradient and spun at 130,000×g at 4° C. Fractions (200 μL) were collected from the top to the bottom of tubes and 40 μL aliquots were mixed with an equal volume of sample buffer (Bio-Rad) and heated for 10 min at 100° C. as per Western blotting and SDS-PAGE gels. The majority of prion particles remained at the top layer of gradient (40%), implying less aggregated, lipid bound states of $PrPs^{sc}$ in the nanodiscs. The indicated SMA(1:1:)ma copolymer is identical to MA-SMA.

Figure 25:
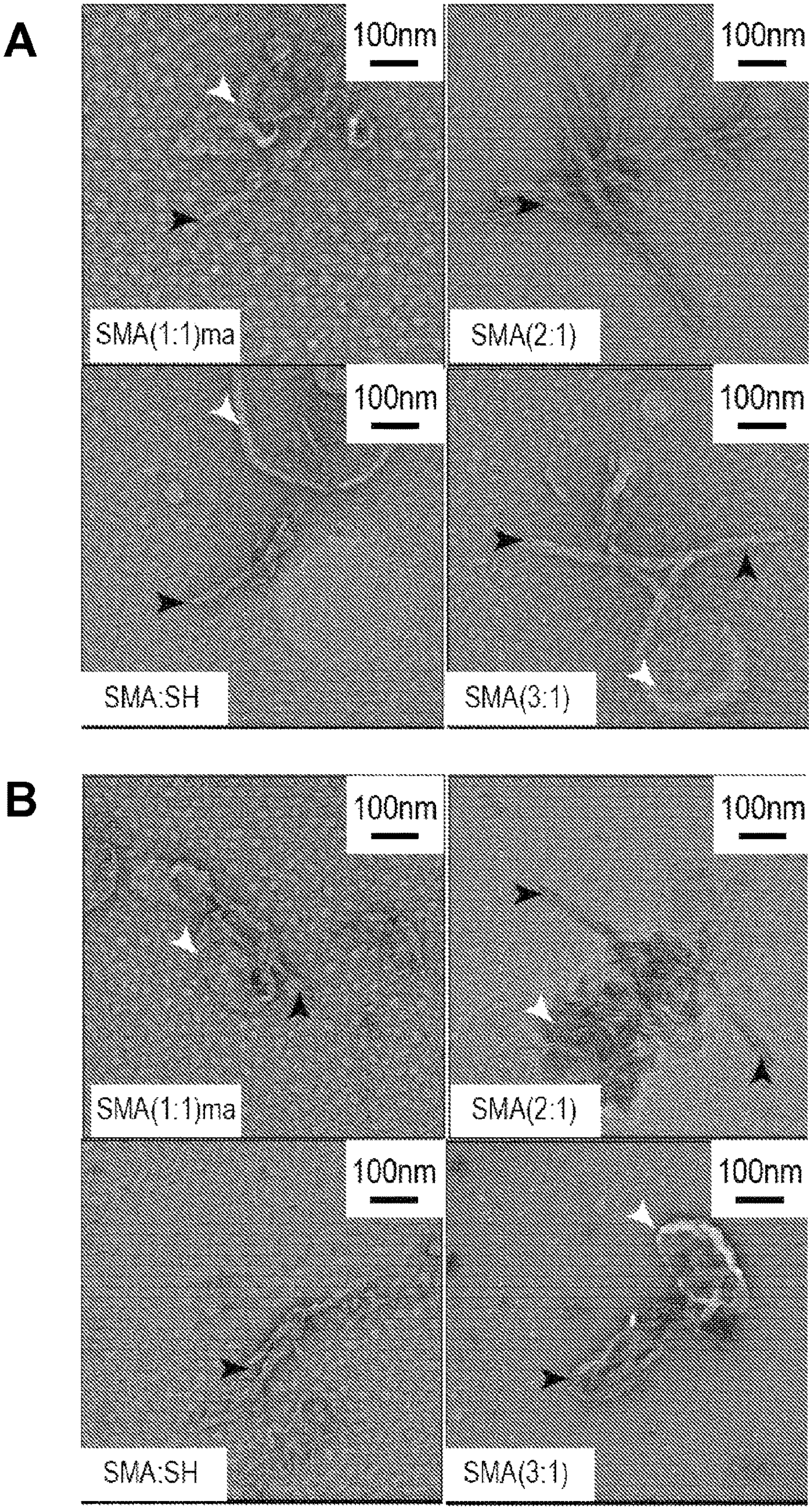

FIG. 25: Negative stain electron micrographs of $PrP^{Sc}$ fibrils from Syrian Hyper hamsters (A panels) and FVB-RML mice (B panels) using the indicated SMA copolymers, with SMA(1:1)ma being a type of MA-SMA copolymer. Carbon coated copper grids (400 mesh) were charged using an EMS Pelco Easy Glow 100 x glow discharge unit (Ted Pella Inc, USA) for 30 seconds. Microliter amounts of each SMA-purified prion sample were loaded on the grids and adsorbed for 30 seconds. The grids were washed three times (3×50 μL) with ammonium acetate (100 mM and 10 mM, pH 6.8), and stained with filtered 2% uranyl acetate. Excess dye was removed using a filter paper and the grid was air-dried for at least 5 minutes before TEM imaging. Micrographs were collected using a Tecnai G20 transmission electron microscope equipped with an Eagle 4 k×4 k CCD camera (FEI Company) using an acceleration voltage of 200 kV. White arrows point to isolated $PrP^{Sc}$ microfilaments and black arrows highlight the co-purified lipid vesicles.

Figure 26:
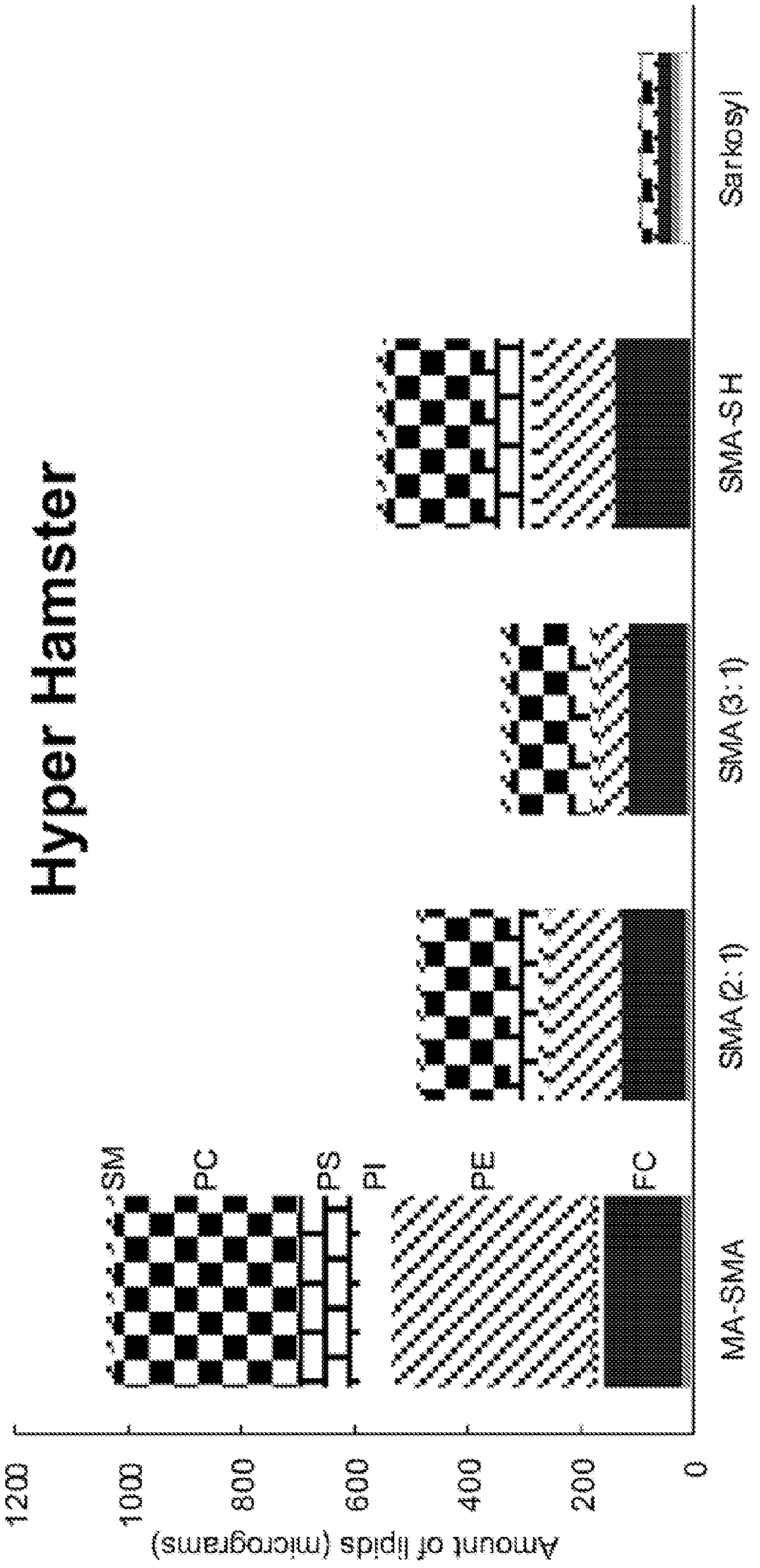
Figure 26:
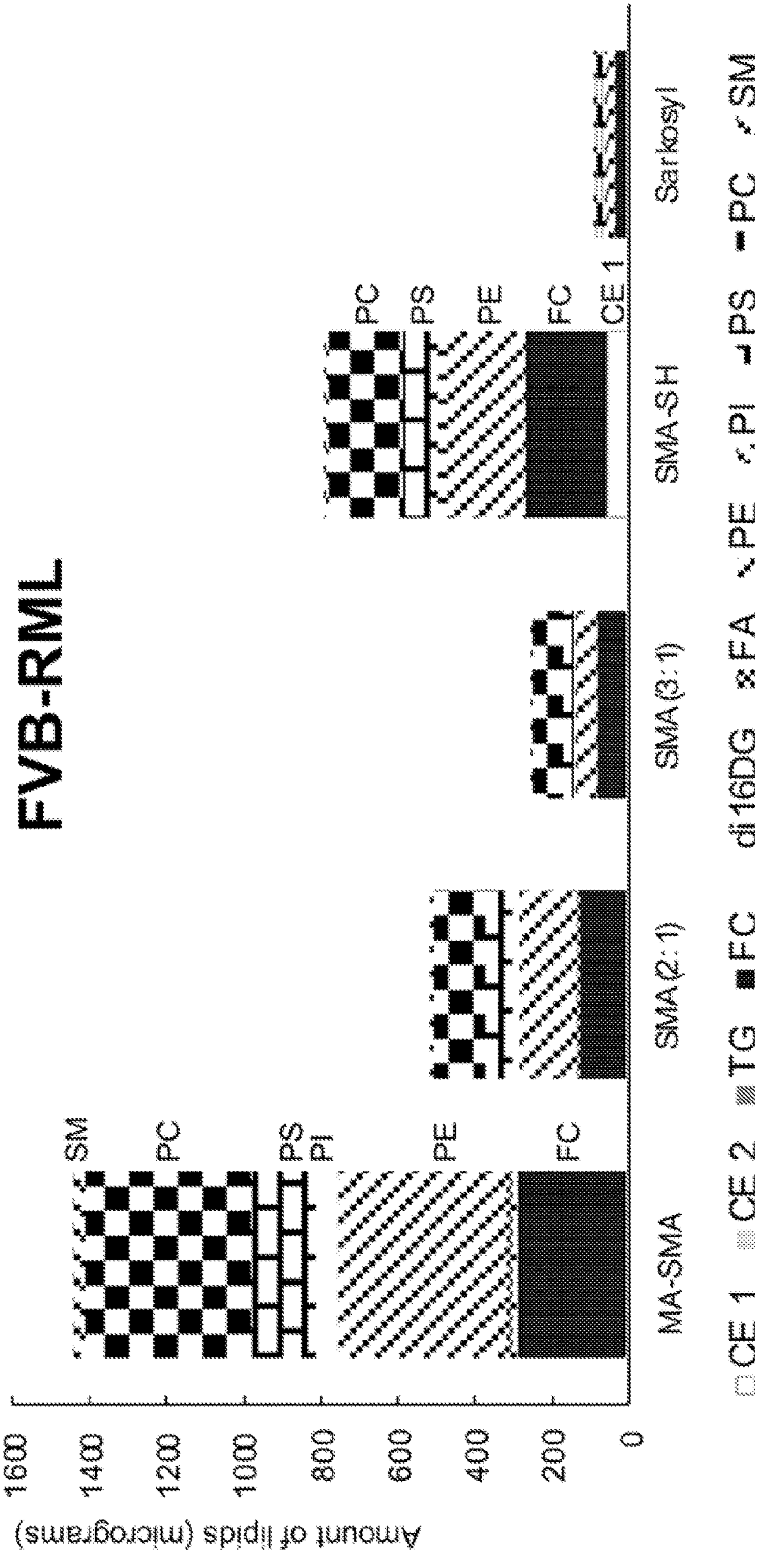

FIG. 26: Different lipid species in each SMA isolated-$PrP^{Sc}$ pellet from Hyper hamster (above) and FVB-RML mice (below) were quantified. The total lipid was isolated from high titer PTA complexes of PrPSc solubilized in SMA polymer or sarkosyl using methanol:chloroform (1:2 v/v) in a BSL-2 lab biosafety cabinet following decontamination by incubation of PTA pellets with 5M guanidinium thiocyanate for one hour at RT. Total lipids were analyzed by HPLC and lipid classes were identified according to their retention time and comparison to commercial standards, and the amounts were quantified using calibration curves for each lipid class. Cumulative amounts of lipid types are shown in stack plots including levels of cholesterol esters (CE), triglycerol (TG), free cholesterol (FC), sn-1,2-dipalmitoyl phosphatidylglycerol (di16PG), free fatty acid (FA), phosphatidylethanolamine (PE), phosphatidylinositol (PI), phosphatidylserine (PS), phosphatidylcholine (PC) and sphingomyelin (SM). The indicated SMA(1:1:)ma copolymer is identical to MA-SMA.

Figure 27:
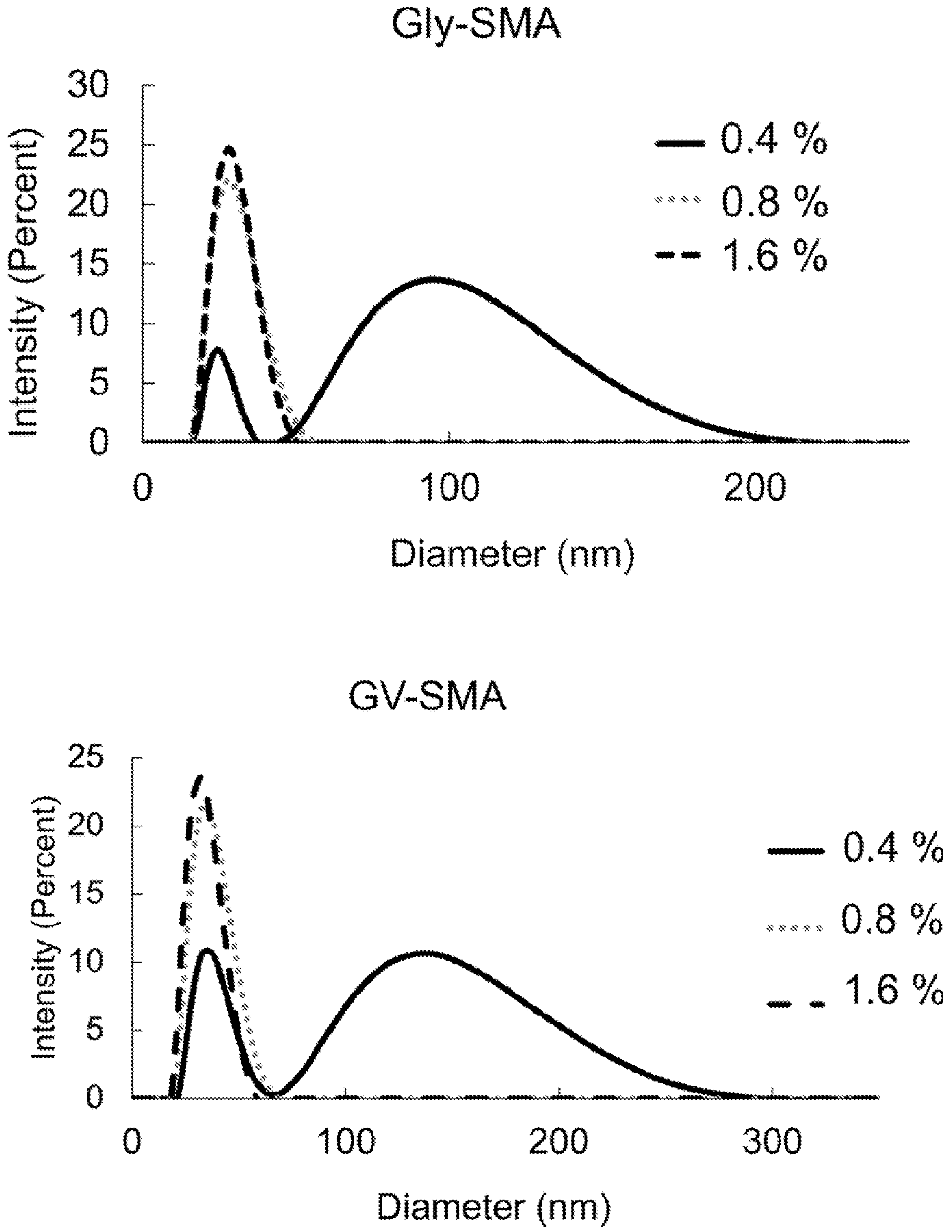

FIG. 27: Dynamic light scattering (DLS) measurements showing the sizes of nanodiscs formed by solubilizing DMPC vesicles with the indicated concentrations of Gly-SMA (above) and GV-SMA (below). The diameters of the populations of nanodiscs are shown in nanometers. At a low copolymer concentration (0.4%) incomplete membrane solubilization leads to bimodal distribution with 100-150 nm membrane fragments as well as the 20-30 nm nanodiscs.

Figure 28:
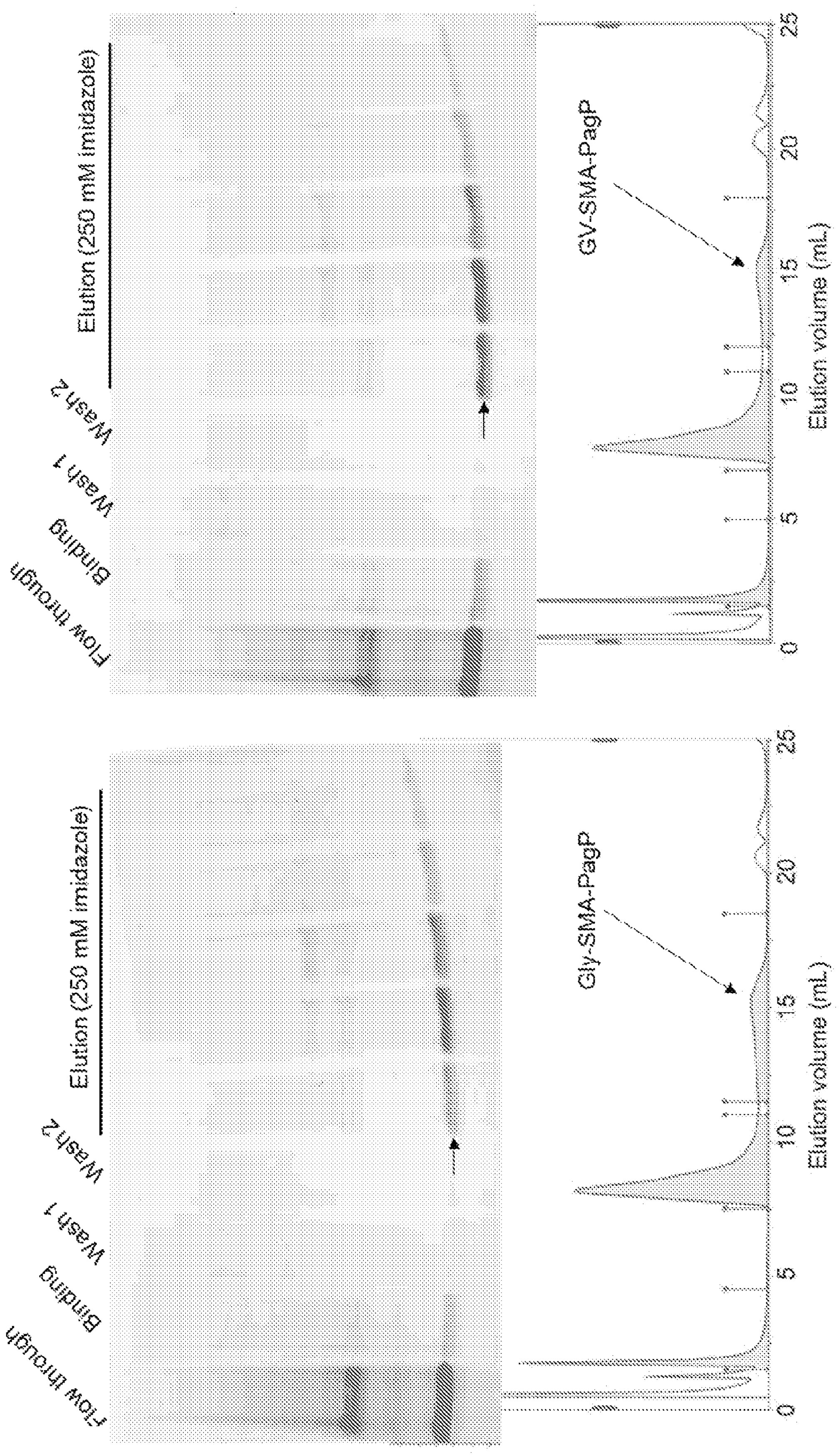

FIG. 28: The solubilization of PagP protein expressed into the outer *E. coli* membrane using Gly-SMA and GV-SMA copolymers is shown. The stain-free SDS-PAGE gels show lanes from left to right depicting molecular weight markers, flow through, 2 washes and 5 4 elutions, with the PagP protein band indicated with an arrow. The PagP proteins were solubilized by Gly-SMA (top left gel) and GV-SMA (top right gel), and their fractions were further purified by size exclusion chromatography with the fractions used to prepare TEM images indicated with asterisks (bottom panels).

Figure 29:
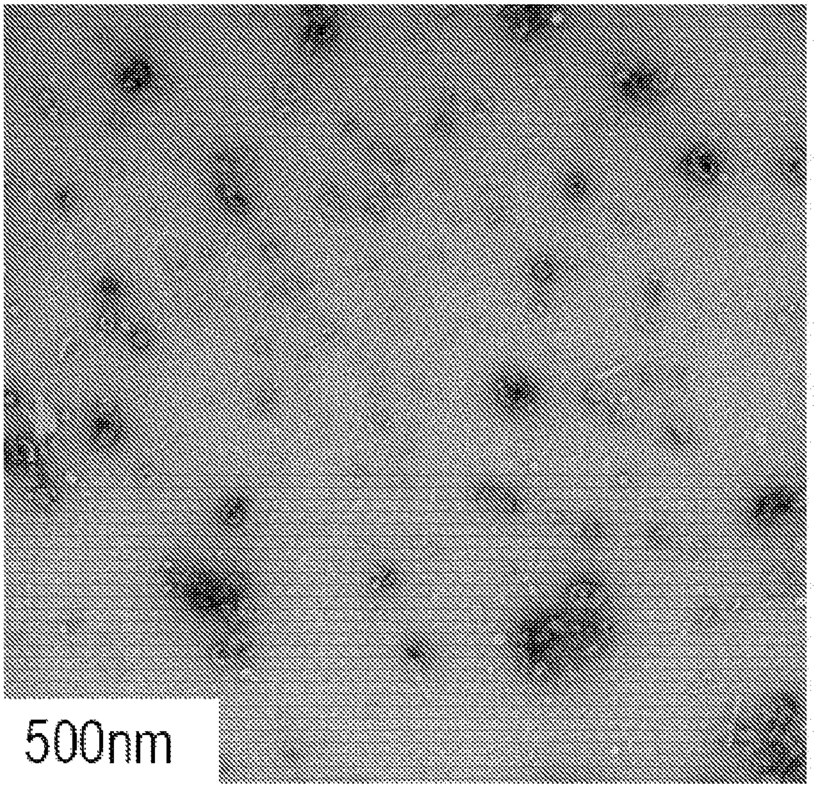

FIG. 29: Negative stain transmission electron micrographs of Gly-SMA-PagP nanodiscs and vesicle fragments formed by Gly-SMA treatment of PagP-containing *E. col* outer membrane. The scale bars are 500 nm (left) and 200 nm (right).

Figure 30:
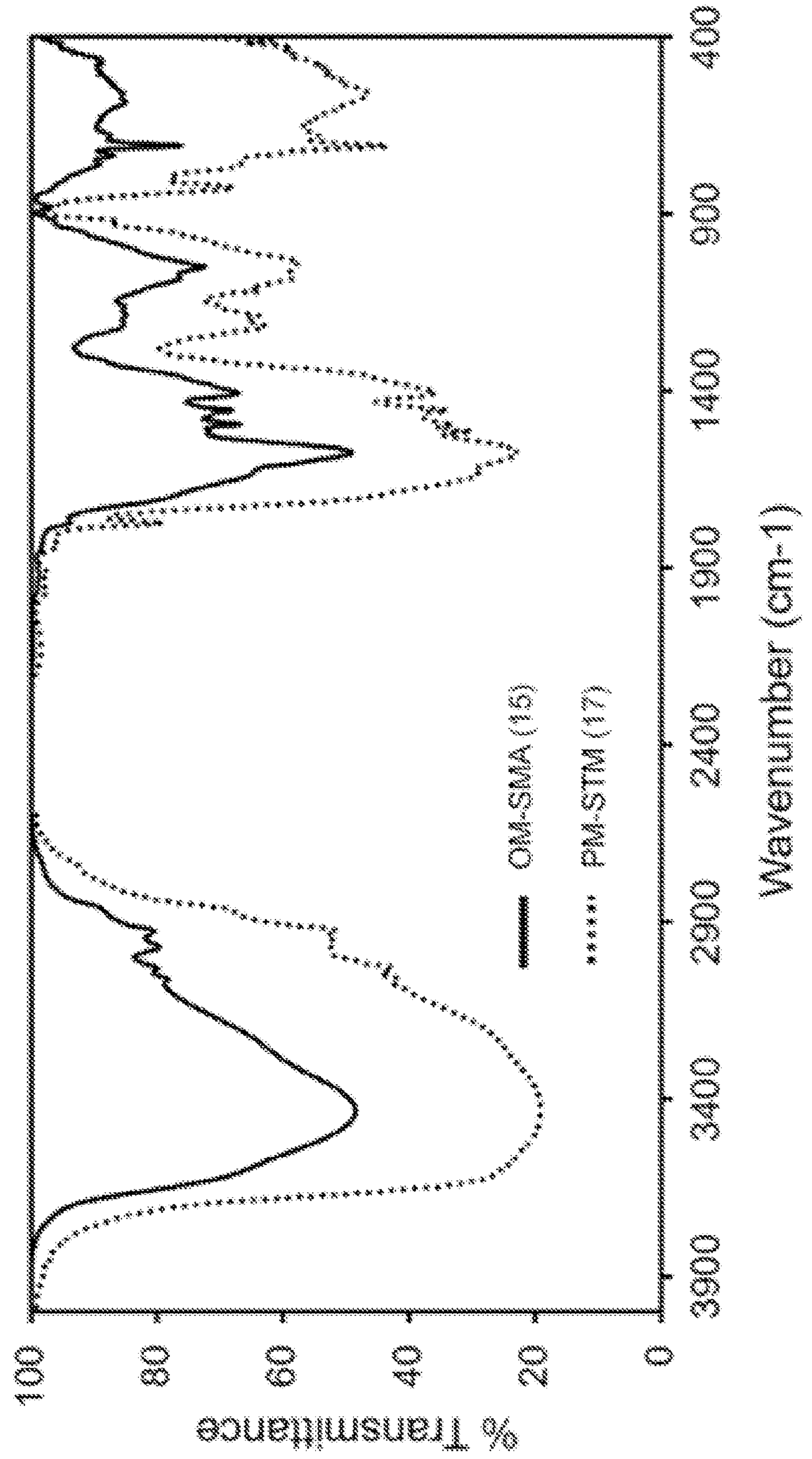

FIG. 30: FT-IR spectra of para-methyl-stilbene-alt-maleic acid (17) and ortho-methyl-stilbene-alt-maleic acid (15) (top) and the 600 MHz $^1$H NMR spectra of these stilbene maleic acid copolymers in aqueous solution (bottom two panels).

Figure 31:
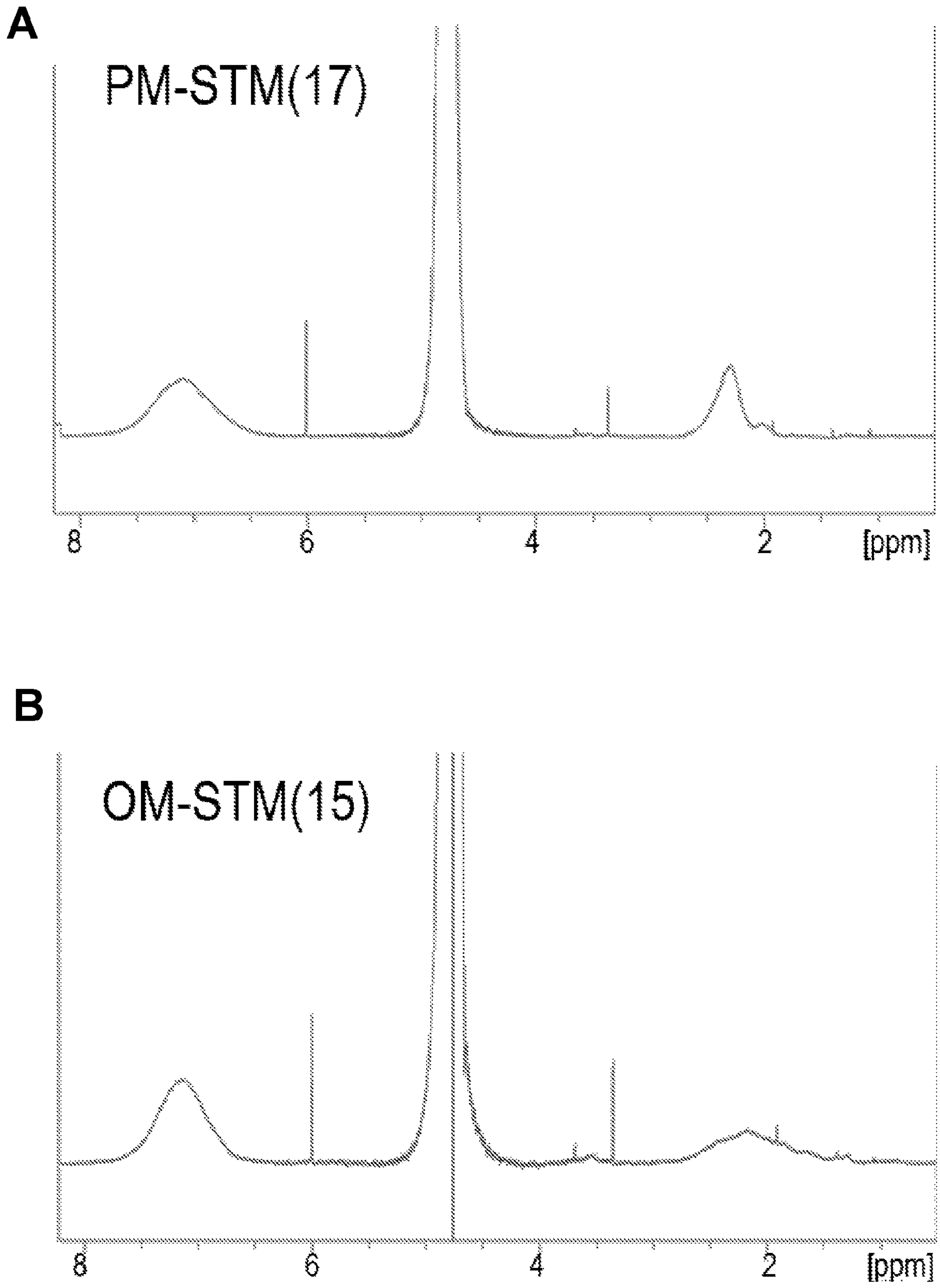

FIG. 31: (A) Solubilization of DMPC lipid vesicles stilbene copolymer. Solutions of vesicles were titrated with the following copolymers: stilbene-alt-maleic acid (STM), di-ortho-methyl-STM (DOM-STM), PM-STM (3), OM-SMT (4), di-para-carboxylate-STM (PCO2-STM). Surprisingly, only para-methyl stilbene-MA (15) and ortho-stilbene-MA (17) clarified the lipid suspensions. (B) The broad $^{31}$P NMR signal shown at 0 parts per million (ppm) of lipid vesicles composed of DMPC (5 mM) (bottom spectrum) becomes resolvable upon addition of copolymers 15 (top spectrum) and 17 (middle spectrum) at 2% w/v concentrations, indicating the formation of rapidly tumbling nanodiscs.

Figure 32:
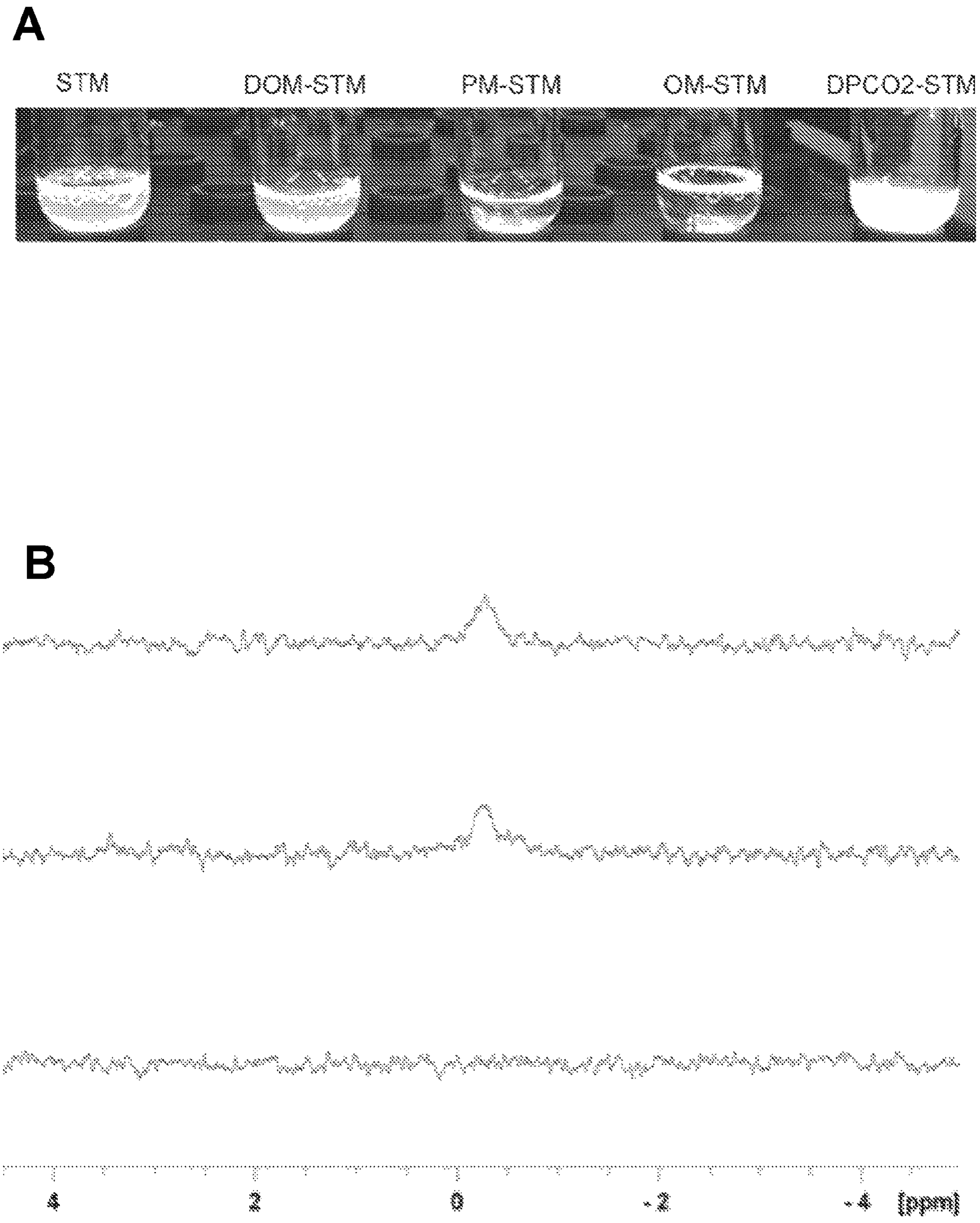

FIG. 32: Aqueous solubility of stilbene maleic acid copolymers over a range of pH values and calcium concentrations. The turbidity of aqueous solutions of OM-STM (top) and PM-STM (bottom) copolymers from pH 4 to 10 (left) and 2.5 to 10 mM $CaCl_2$ (right) is shown. Both copolymers are water soluble from pH 5 to 10, as seen by the clarity of the solutions, and at 2.5 mM $CaCl_2$, and form suspensions of precipitates at higher calcium concentrations.

Figure 33:
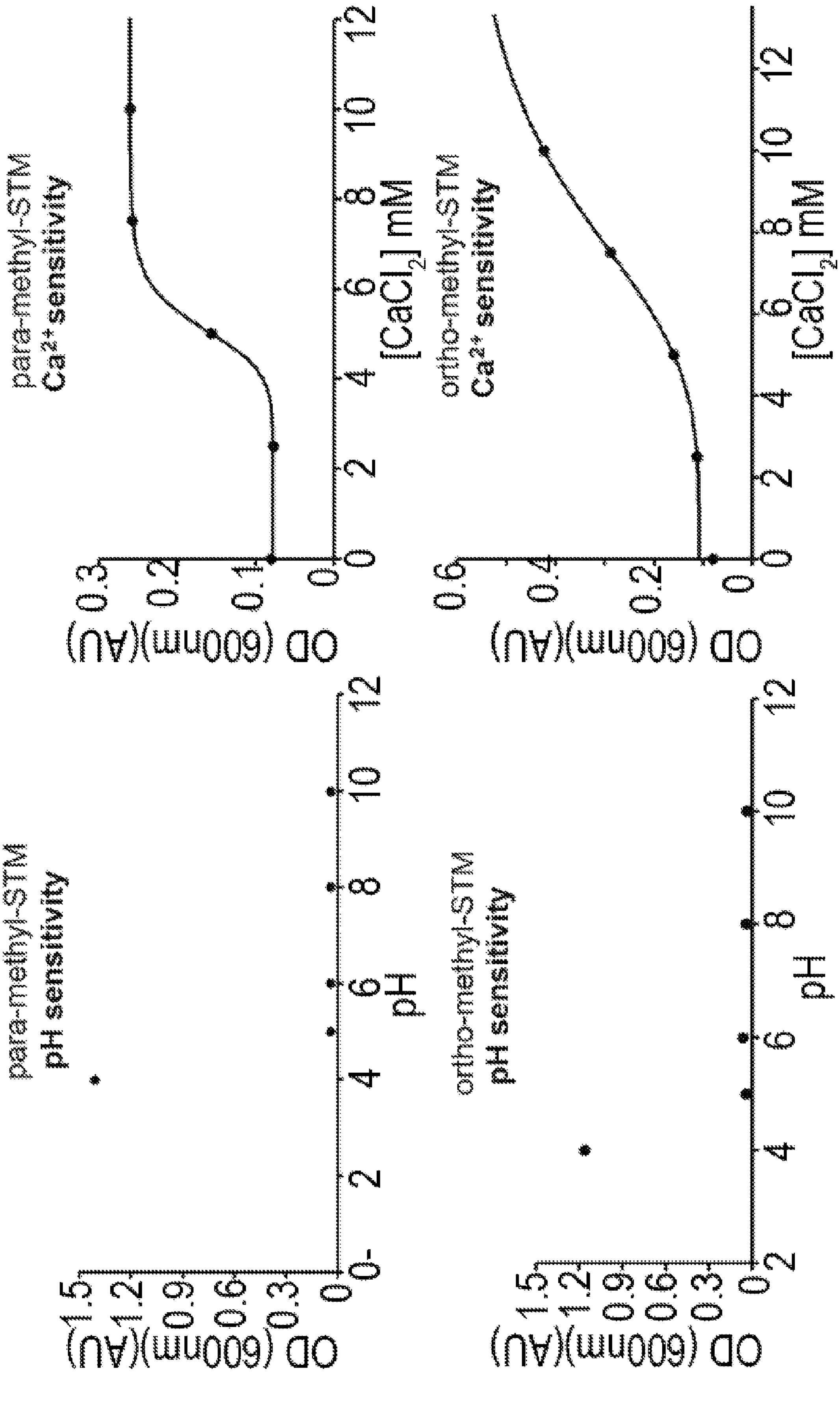

FIG. 33: The solution behaviour of copolymers ortho- and para-methyl STM compounds 15 and 17 was measured by the turbidity of samples in various calcium and pH levels. The sensitivity of the copolymers was assayed at an optical density of 600 nm and indicated the formation of precipitates at pH 5 or calcium levels at 5mM and above. Measured in Tris buffer (10mM, pH 8) which was used as a reference.

Figure 34:
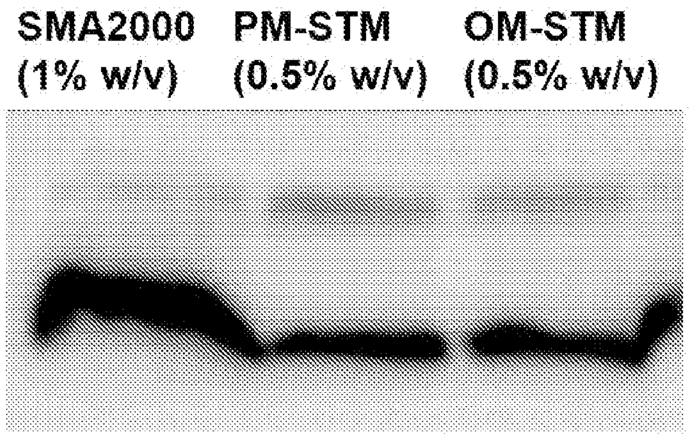

FIG. 34: Derivatized stilbene maleic acid copolymers solubilize *E.coli* membrane. The Western blot of the His-tagged PagP protein solubilized by SMA2000 (1% w/v), PM-STM (0.5% w/v) and OM-STM (0.5% w/v) is shown.

Figure 35:
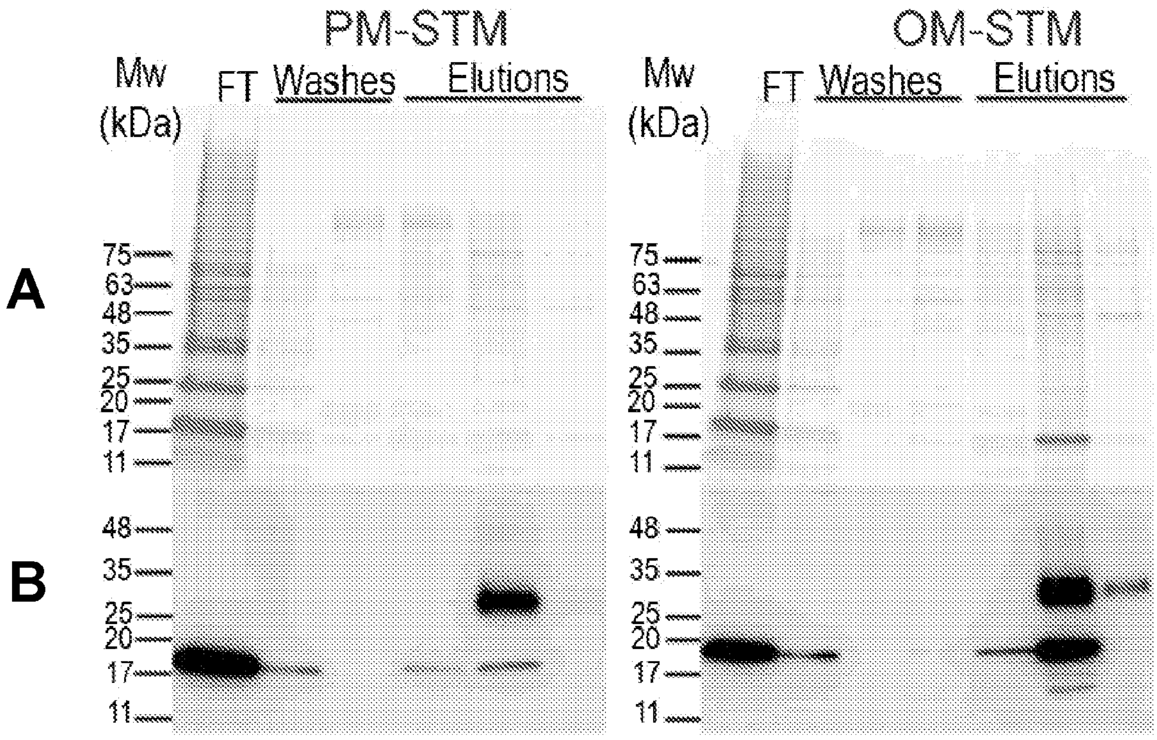

FIG. 35: Solubilization of PagP protein from *E. col* membrane using stilbene maleic acid copolymers. (a) The stain-free SDS-PAGE gel shows PagP protein extracted and partially purified from the outer *E. coli* membrane with PM-STM and OM-STM. The lanes of each gel show flow through (FT), Ni-NTA bound, washes with 10 and 30 mM imidazole and elutions with 250 mM imidazole from left to right. (b) The western blots on the bottom show the protein purified PM-STM (left) and OM-STM (right) stained with HisProbe™-HRP conjugate (1:6000, Pierce) probe (HisProbe) as well as the molecular weight markers.

Figure 36:
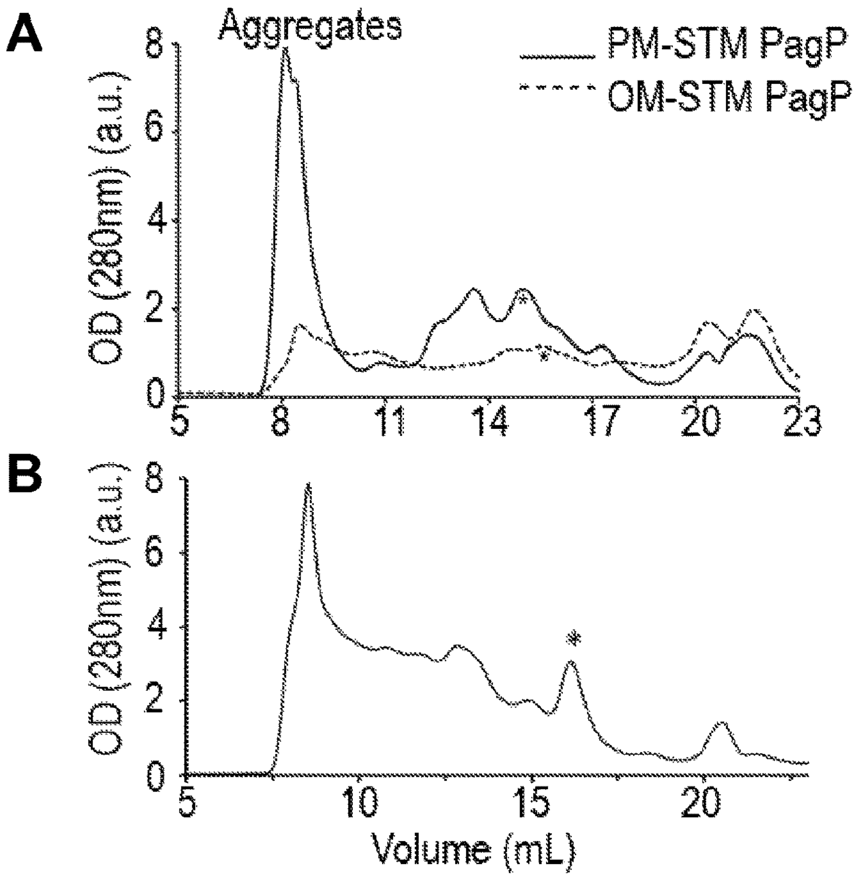

FIG. 36: SEC profiles of PagP nanodiscs formed using PM-STM and OM-STM (a) and PagP-SMA2000 nanodiscs (b) purified by nickel affinity column. The optical density at 600 nm is shown on the y-axis and the elution volume is shown on the x-axis with asterisks marking the fractions that contain major amount of nanodiscs and that were used for TEM imaging.

Figure 37:
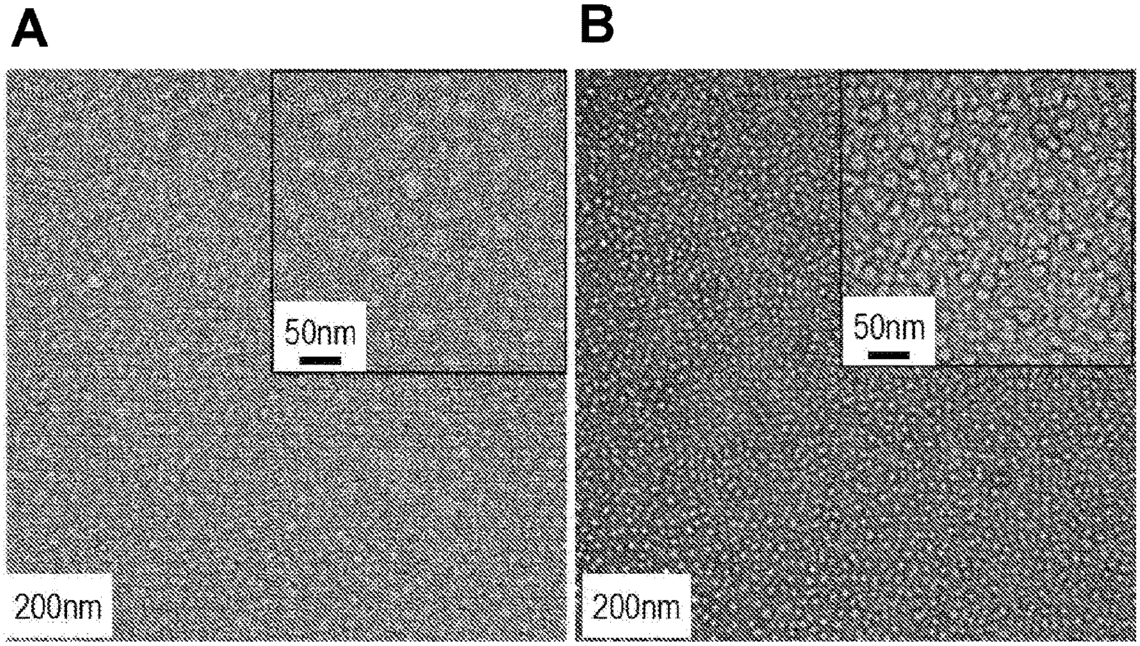

FIG. 37: Native nanodiscs containing *E. coli* outer membrane sections including PagP protein after being solubilized by stilbene maleic acid copolymers and resolved by transmission electron microscopy. The 200 nm and 50 nm bars below each image show the respective image scales. The nanodiscs had been partially purified by Ni-NTA and size exclusion chromatography.

Figure 38:
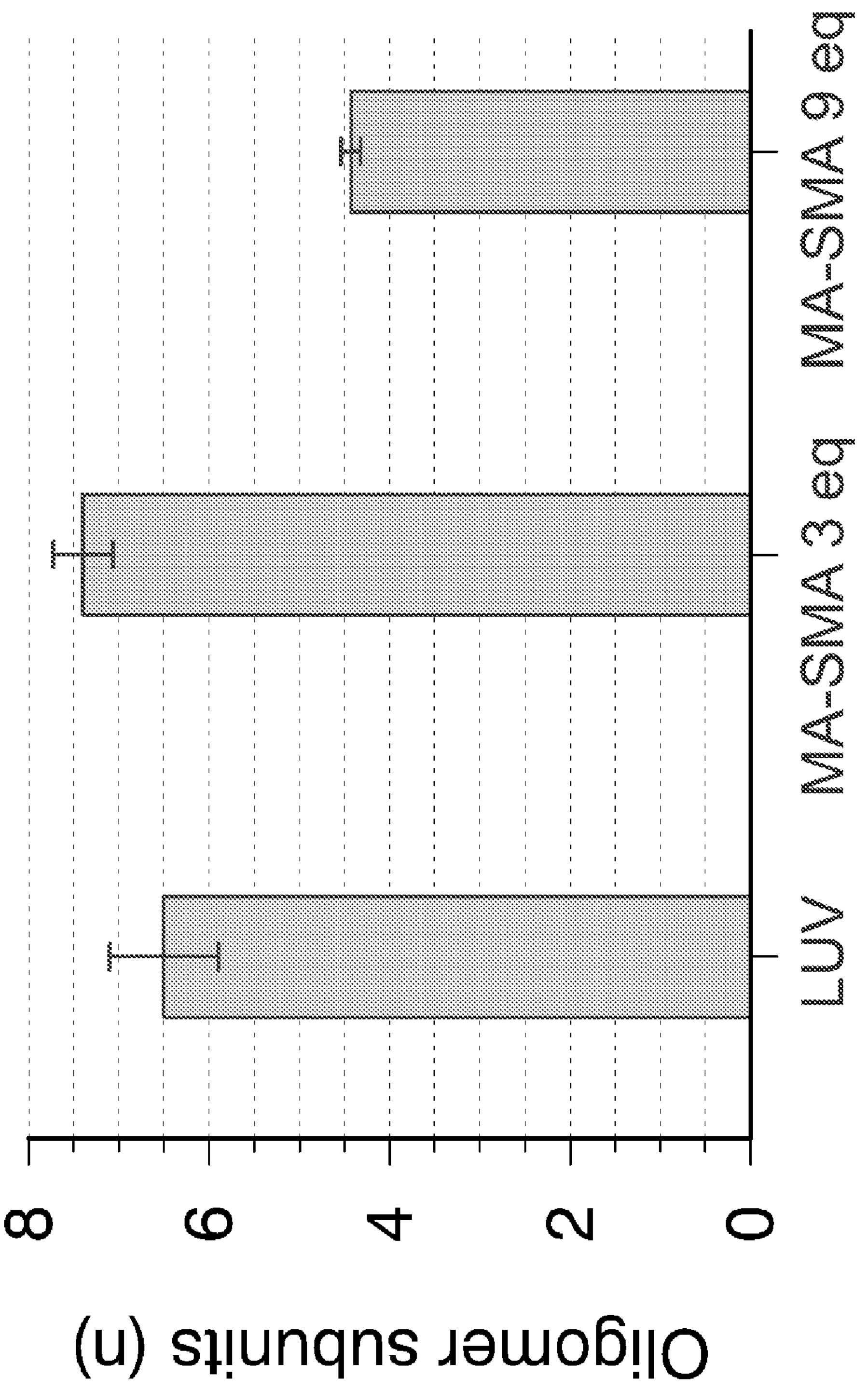

FIG. 38: FRET between native daptomycin and NBD-daptomycin in DMPC/DMPG-containing nanodiscs containing 3 or 9 equivalents of MA-SMA relative to lipid.

Nanodiscs were formed by treating 250 μM of total lipid (DMPC:DMPG at a ratio of 1:1) with native daptomycin donor and NBD-daptomycin acceptor premixed at a molar ratio of 4:1 and a combined concentration of 10 μM. Samples contained 10 mM HEPES, 25 mM NaCl buffer, pH 7.4 (HBS) with 3 mM CaCl2. The resulting mixture was incubated for 3 min and a kynurenine emission spectrum recorded at 37° C. After the measurement, an additional 4μM of native dap was added to the sample. Following incubation for another 3 min, another fluorescence emission spectrum was recorded. From these two measurements, the subunit stoichiometry was determined. The data presented are the averages with standard deviations of 8 independent experiments. The initial addition of donor and acceptor yields the uncorrected donor fluorescence, which was then calibrated by a second addition of donor only, allowing the oligomer subunit stoichiometries to be determined.

Figure 39:
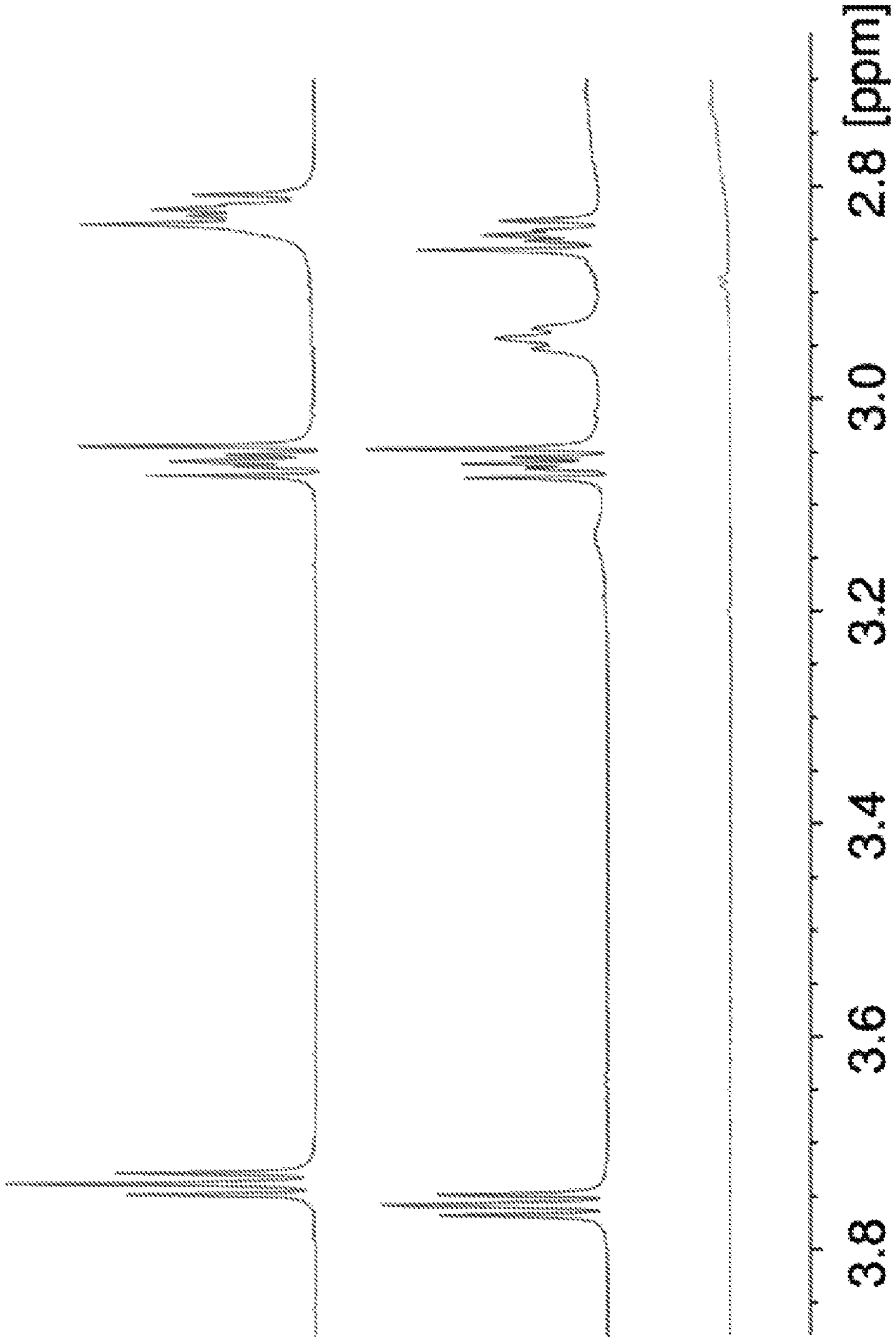

FIG. 39: NMR spectra of $^1$H resonances from 2.8 to 3.8 ppm of 85 μM daptomycin interacting with DMPC/DMPG nanodiscs stabilized by nine copolymer equivalents, as well as of control samples without daptomycin or nanodiscs. The samples contain daptomycin and $Ca^{2+}$ (top spectrum), MA-SMA, daptomycin and $Ca^{2+}$ (middle) and MA-SMA and $Ca^{2+}$ (bottom). All samples contain 10% $D_2O$ in HBS. Data were acquired at 28° C. on a 600 MHz Bruker Avance spectrometer. The chemical shifts were referenced to the water proton signal at 4.7 ppm.

Figure 40:
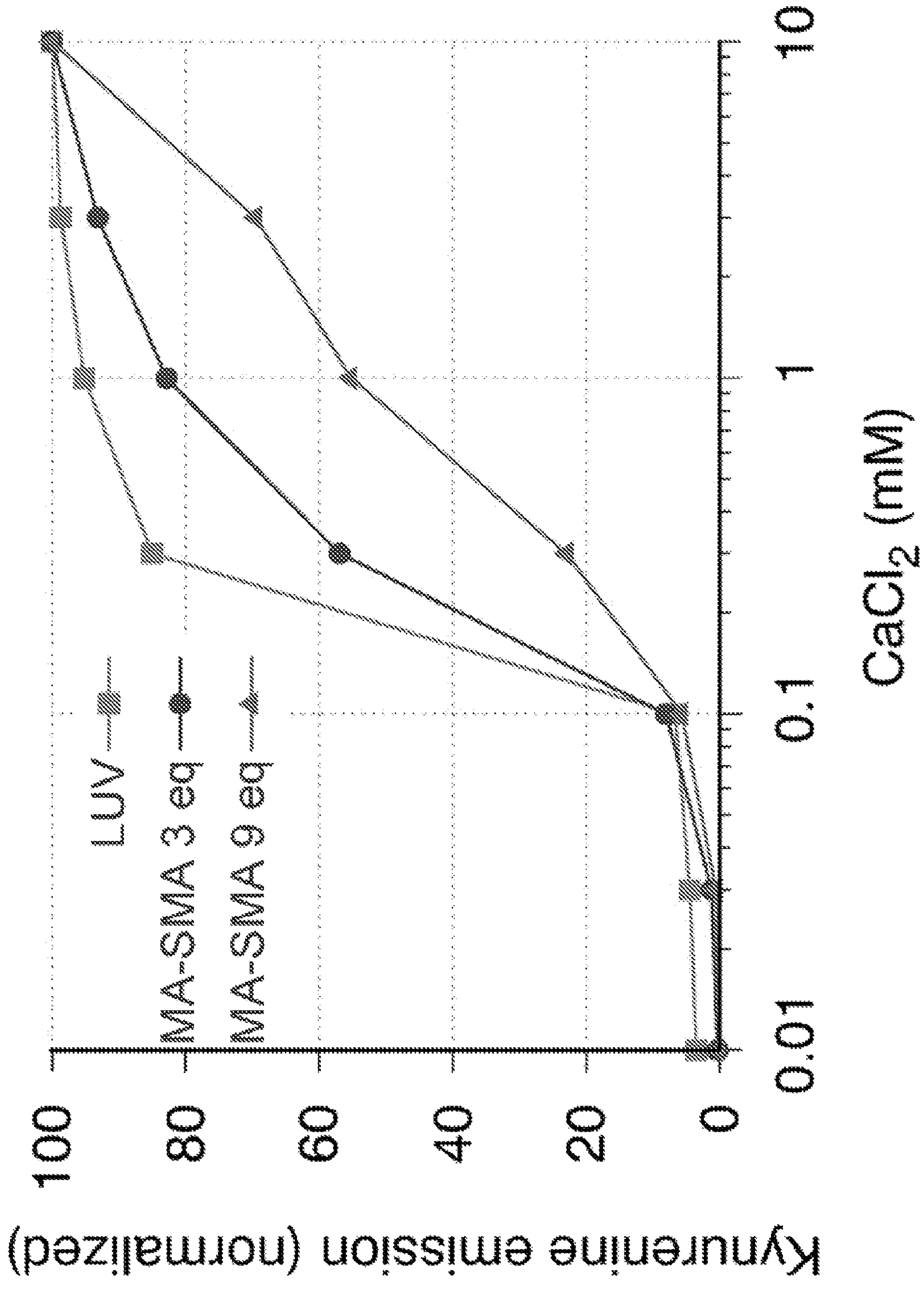

FIG. 40: Fluorescence assays for determination of daptomycin binding to MA-SMA-bounded DMPC/DMPG nanodisc or LUV membranes in a calcium-dependent fashion. Dap binding was measured by kynurenine fluorescence. Signal intensity is normalized to 10 mM calcium. Emission spectra (excitation wavelength: 365 nm; emission wavelength: 400-600 nm) were acquired on a PTI QuantaMaster 4 instrument at 37° C.

TABLE 1

List of FDM copolymers that demonstrate the utility of various embodiments.

| Chemical Name | Short Name | Scheme | Compound |
|---|---|---|---|
| poly(styrene-maleamic acid-histamine) | His-SMA | 2 | 1 |
| poly(styrene-maleimide-histamine) | His-SMAi | 2 | 2 |
| poly(styrene-maleamic acid-ethyl-dimethylamine-oxide) | AO2-SMA | 3 | 3 |
| poly(styrene-maleimide-ethyl-dimethylamine-oxide) | AO2-SMAi | 3 | 4 |
| poly(styrene-maleamic acid-ethyl-dimethylamine-oxide) | AO3-SMA | 4 | 5 |
| poly(styrene-maleimide-propyl-dimethylamine-oxide) | AO3-SMAi | 4 | 6 |
| poly(styrene-maleamic acid-1,3-propanediol) | PDO-SMA | 6 | 7 |
| poly(styrene-maleimide-1,3-propanediol) | PDO-SMAi | 6 | 8 |
| poly(styrene-alt-maleamic acid-methylamine) | MA-SMA | 8 | 9 |
| poly(styrene-alt-maleamic acid-ethylamine) | EA-SMA | 8 | 10 |
| poly(styrene-alt-maleamic acid-propylamine) | PA-SMA | 8 | 11 |
| poly(styrene-maleamic acid-glycine-methyl-ester) | Gly-SMA | 11 | 12 |
| poly(styrene-maleimide-glycine-methyl-ester) | Gly-SMAi | 11 | 13 |
| poly(styrene-maleamic acid-glycine,valine-methyl-ester) | GV-SMA | 12 | 14 |
| poly(ortho-methyl-stilbene-maleic acid) | OM-STM | 14 | 15 |
| poly(ortho-methyl-stilbene-maleamic acid) | OM-STMA | 14 | 16 |
| poly(para-methyl-stilbene-maleic acid) | PM-STM | 16 | 17 |
| poly(para-methyl-stilbene-maleamic acid) | PM-STMA | 16 | 18 |
| poly(styrene-alt-maleamic acid-propyl-trimethylammonium) | PTMA-SMA | 18 | 19 |
| poly(styrene-alt-maleimide-propyl-trimethylammonium) | PTMA-SMI | 18 | 20 |
| poly(styrene-alt-maleamic acid-ethyl-dimethylamine) | EDMA-SMA | 18 | 21 |
| poly(styrene-alt-maleimide-ethyl-dimethylamine) | EDMA-SMI | 18 | 22 |
| poly(styrene-alt-maleamic acid-propanolamine) | POA-SMA | 18 | 23 |
| poly(styrene-alt-maleimide-propanolamine) | POA-SMI | 18 | 24 |
| poly(diisobutylene-alt-maleamic acid) | DIB-MA | 18 | 25 |
| poly(diisobutylene-alt-maleimide) | DIB-MI | 18 | 26 |
| poly(diisopropylene-alt-maleamic acid) | DIP-MA | 18 | 27 |
| poly(diisopropylene-alt-maleimide) | DIP-MI | 18 | 28 |
| poly(methyl-styrene-alt-maleamic acid) | Me-SMA | 18 | 29 |
| poly(methyl-styrene-alt-maleimide) | Me-SMI | 18 | 30 |
| poly(hydroxy-styrene-alt-maleamic acid | OH-SMA | 18 | 31 |
| poly(bromo-styrene-alt-maleamic acid | Br-SMA | 18 | 32 |
| poly(styrene-alt-maleamic acid-trifluoroethylamine) | FEA-SMA | 18 | 33 |
| poly(styrene-alt-maleamic acid-trifluoropropylamine) | FPA-SMA | 18 | 34 |
| poly(styrene-alt-maleamic acid-bromoethylamine) | BEA-SMA | 18 | 35 |
| poly(styrene-alt-maleamic acid-bromopropylamine) | BPA-SMA | 18 | 36 |

DETAILED DESCRIPTION

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* $14^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that reference to a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about" or the term "approximately".

These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" can refer to a variation of ±1%, ±2%, ±3%, ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, composition, or embodiment. The term about can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The terms "combining" and "contacting" refer to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The term "substantially" is typically well understood by those of skill in the art and can refer to an exact ratio or configuration, or a ratio or configuration that is in the proximity of an exact value such that the properties of any variation are inconsequentially different than those ratios and configurations having the exact value. The term "substantially" may include variation as defined for the terms "about" and "approximately", as defined herein above. The term "substantially" may also refer to a numerical value that may not be 100% the full numerical value. The full numerical value may be less by about 1%, about 2%, about 3%, about 4%, about 5%, about 6%, about 7%, about 8%, about 9%, about 10%, about 15%, about 20%, about 25%, about 30%, about 35%, or about 40%.

Embodiments of the Invention

This disclosure provides an amphiphilic copolymer comprising Formula $I^A$, Formula $I^B$, or a combination thereof, wherein: i) Formula $I^A$ is represented as, ($I^A$)

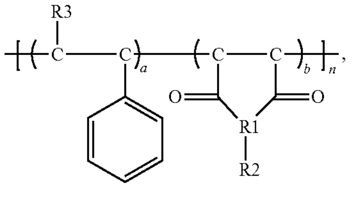

wherein

R1 is N;

R2 is —($C_1$-$C_{12}$)alkyl, alkanol, alkylamine, alkylamine oxide, or quaternary amine, wherein —($C_1$-$C_{12}$)alkyl is substituted optionally with halo; or R1 and R2 taken together form a histamine, amino alkanediol, or alkyl ester of an amino acid residue; and R3 is a hydrogen, unsubstituted phenyl, or phenyl substituted by one or more non-polar substituents;

ii) Formula $I^B$ is represented as, ($I^B$)

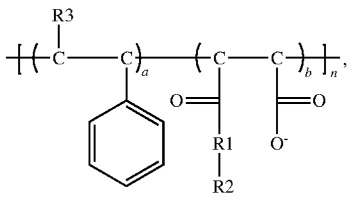

wherein

R1 is 0 or NH;

when R1 is O, R2 is H;

when R1 is NH:

R2 is —($C_1$-$C_{12}$)alkyl, alkanol, alkylamine, alkylamine oxide, quaternary amine, wherein —($C_1$-$C_{12}$)alkyl is substituted optionally with halo; or R1 and R2 taken together form a histamine, amino alkanediol, or alkyl ester of an amino acid residue; and R3 is a hydrogen, unsubstituted phenyl, or phenyl substituted by one or more non-polar substituents;

wherein the oxygen anion of Formula $I^B$ has a positively charged monovalent counter ion; and iii) independently for Formula $I^A$ and $I^B$, n is about 7 to about 200, and the monomer moieties labeled a and b are in an alternating, substantially alternating, largely alternating, or semialternating copolymer arrangement in the length of the copolymer backbone;

wherein a=b=1 for the alternating copolymer arrangement; 1<a 1.2 and b=1 for the substantially alternating copolymer arrangement; 1.2<a≤1.4 and b=1 for the largely alternating copolymer arrangement; or 1.7≤a≤2.3 and b=1 for the semialternating copolymer arrangement; and provided that for Formula $I^A$ and $I^B$, when R3 is a hydrogen, R1 is not O and R2 is not alkylamine oxide, ($C_1$-$C_3$)alkyl, quaternary amine, or alkanol.

In another embodiment, the amphiphilic copolymer comprises Formula $I^A$ or $1^B$, or a combination thereof: wherein R1 is a nitrogen in Formula $I^A$ and R1 in Formula $I^B$ is either a —NH— when R3 is a hydrogen or when R3 is an unsubstituted phenyl, or phenyl substituted by one or more non-polar substituents at the ortho, meta or para positions, then R1 is an —O and R2 is a hydrogen;

R2 is a polar group, or ($C_1$-$C_{12}$)alkyl;

wherein when R2 is a polar group, R1 and R2 taken together form a histamine, an alkylamine oxide, amino alkanediol, alkyl amine, alkanolamine, quaternary amine, or an alkyl ester of an amino acid residue;

R3 is a hydrogen, unsubstituted phenyl, or phenyl substituted by one or more non-polar substituents at the ortho, meta or para positions;

provided that when R3 is a hydrogen, R2 is not an alkylamine oxide, ($C_1$-$C_3$)alkyl, a quaternary amine, or an alkanolamine;

the monovalent counterion for the $O^-$ moiety of Formula $I^B$ is optionally $Na^+$, $K^+$, or $NH_4^+$;

the monomer moieties labeled a and b are in an alternating (wherein a=b=1), substantially alternating (wherein 1<a≤1.2, b=1), largely alternating (wherein 1.2<a1.4, b=1), or semialternating (wherein 1.7≤a≤2.3, b=1) copolymer arrangement in the length of the copolymer backbone, wherein the phenyl ring shown in subunits a optionally have one or more alkyl, halo, —OH, or —$NH_2$ substituents in place of one or more hydrogen atoms of the phenyl ring; and n is equal to optimally between 10 and 45, preferably between 9 and 90 and generally between 7 and 200.

In various embodiments, the copolymer is represented by Formula $I^A$. In various embodiments, copolymer is represented by Formula $I^B$. In various embodiments, the copolymer is cyclized by a crosslink between the two termini of the copolymer chain. In various embodiments, the counterion can be any suitable positively charged counterion, such as a metal, non-metal or small molecule. In various embodiments, the —($C_1$-$C^{12}$)alkyl moiety has substituents such as, but not limited to, halo, hydroxy, amino, or trifluoromethyl. In various embodiments, the phenyl moiety in subunit-a of Formula $I^A$ or Formula $I^B$ optionally has one or more alkyl, halo, —OH, or —$NH_2$ substituents that replace one or more hydrogen on the phenyl ring.

In various embodiments, R2 is —($C_1$-$C_{12}$)alkyl substituted with halo or alkyl. In various embodiments, —($C_1$-$C_{12}$)alkyl is unbranched or branched. In various embodiments, R3 is an unsubstituted phenyl, or phenyl substituted by one or more non-polar substituents when R1 is —NH. In various embodiments, the —CH(Ph) — moiety in subunit-a of Formula IA or IB is replaced with the moiety —$C(CH_3)(CH_2C(CH_3)_3)$— or another alkylene moiety.

In various embodiments, R1 and R2 taken together form ethyl-dimethylamine-oxide, propyl-dimethylamine-oxide, serinol, glycine-methyl-ester, or valine methyl ester. In various embodiments, R1 is N and R2 is —($C_2$-$C_3$)alkyl-$N(O)(CH_3)_2$, —$(CH_2)_3$—$N(CH_3)_3$, —($C_1$-$C_3$)alkyl-$(halo)_{1-3}$, —$(CH_2)_3$—OH, or —$(CH_2)_2$—$N(CH_3)_2$. In various embodiments, R3 is phenyl substituted by one or more methyl or —($C_2$-$C_{12}$)alkyl groups. In various embodiments, —($C_1$-$C_3$)alkyl-$(halo)_{1-3}$ is —($C_1$-$C_3$)alkyl-Br or —($C_1$-$C_3$)alkyl-$F_3$ such as —$CH_2CH_2CF_3$.

In various embodiments, the monomer moiety labeled b is a hydrophilic subunit and the monomer moiety labeled a is a hydrophobic subunit, and wherein a and b are present in a substantially equimolar ratio wherein a and b are approximately both 1 and a and b are in a substantially alternating configuration in the linear sequence of the copolymer.

In various embodiments, the copolymer is: poly(styrene-alt-maleamic acid-histamine) (1), poly(styrene-alt-maleimide-histamine) (2), poly(styrene-alt-maleamic acid-ethyl-dimethylamine-oxide) (3), poly(styrene-alt- maleimide-propyl-dimethylamine-oxide) (4), poly(styrene-alt-maleamic acid-propyl-dimethylamine-oxide) (5), poly(styrene-alt-maleimide-propyl-dimethylamine-oxide) (6), poly(styrene-alt-maleamic acid-1,3-propanediol) (7), poly(styrene-alt-maleimide-1,3-propanediol) (8), poly(styrenealt-maleamic acid-methylamine) (9), poly(styrene-alt-maleamic acid-ethylamine) (10), poly(styrene-alt-maleamic acid-propylamine) (11), poly(styrene-alt-maleamic acid-glycine-methyl-ester) (12), poly(styrene-alt-maleamic acid-glycine-methyl-ester) (13), poly(styrene-alt-maleamic acid-glycine,valine-methyl-ester) (14), poly(ortho-methyl-stilbene-maleic acid) (15), poly(ortho-methyl-stilbene-maleamic acid) (16), poly(para-methyl-stilbene-maleic acid) (17), poly(para-methyl-stilbene-maleamic acid) (18), poly (styrene-alt-maleamic acid-propyl-trimethylammonium) (19), poly(styrene-alt-maleimide-propyl-trimethylammonium) (20), poly(styrene-alt-maleamic acid-ethyl-dimethylamine) (21), poly(styrene-alt-maleimide-ethyl-dimethylamine) (22), poly(styrene-alt-maleamic acid-propanolamine) (23), or poly(styrene-alt-maleimide-propanolamine) (24), poly(diisobutylene-alt-maleamic acid) (25), poly(diisobutylene-alt-maleimide) (26), poly(diisopropylene-alt-maleamic acid) (27), poly(diisopropylene-alt-maleimide) (28), poly (methyl-styrene-alt-maleamic acid) (29), poly(methyl-styrene-alt-maleimide) (30), poly(hydroxy-styrene-alt-maleamic acid (31), poly(bromo-styrene-alt-maleamic acid (32), poly(styrene-alt-maleamic acid-trifluoroethylamine) (33), poly(styrene-alt-maleamic acid-trifluoropropylamine) (34), poly(styrene-alt-maleamic acid-bromoethylamine) (35), poly(styrene-alt-maleamic acid-bromopropylamine) (36).

Also, this disclosure provides a disc-shaped nanoparticle comprising an amphiphilic copolymer and biological material comprising complexes of hydrophobic molecules;

wherein a plurality of the amphiphilic copolymers forms a nanodisc having a hydrophilic outer surface, a regularized annulus, and a hydrophobic inner core;

wherein the biological material is held in an annulus of the nanodisc; wherein the amphiphilic copolymer comprising Formula $I^A$ or $I^B$, or a combination thereof:

($I^A$)

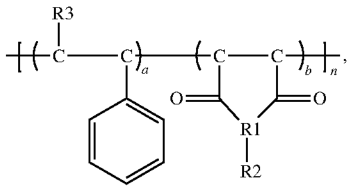

($I^B$)

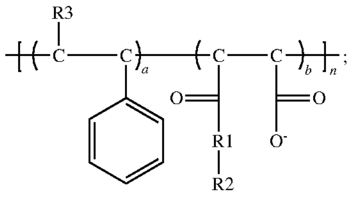

wherein

R1is a nitrogen in Formula $I^A$ and R1 in Formula $I^B$ is either a —NH— when R3 is a hydrogen or when R3 is an unsubstituted phenyl, or phenyl substituted by one or more non-polar substituents at the ortho, meta or para positions, then R1 is an —O and R2 is a hydrogen;

R2 is a polar group in Formula $I^A$ or R2 is a polar group or H in Formula $I^B$;

wherein when R1 is nitrogen or —NH— and R2 is a polar group, R1 and R2 taken together form a histamine, alkylamine oxide, amino alkanediol, alkyl amine, alkanolamine, quaternary amine, or an alkyl ester of an amino acid residue;

R3 is a hydrogen, or an unsubstituted phenyl, or phenyl substituted by one or more alkyl substituents at the ortho, meta or para positions;

provided that when R1 is O and R2 is hydrogen, R3 is an optionally substituted phenyl;

and provided that when R1 and R2 taken together form an alkanolamine or quaternary amine, R3 is an optionally substituted phenyl;

wherein the phenyl ring shown in subunits a optionally have one or more alkyl substituents in place of one or more hydrogen atoms of the phenyl ring;

the monovalent counterion for the $O^-$moiety of Formula $I^B$ is optionally $Na^+$, $K^+$, or $NH_4^+$;

the monomer moieties labeled a and b are in an alternating (wherein a=b=1), substantially alternating (wherein 1<a≤1.2, b=1), largely alternating (wherein 1.2<a≤1.4, b =1), or semialternating (wherein 1.7≤a≤2.3, b=1) copolymer arrangement in the length of the copolymer backbone of the copolymer;

n is equal to optimally between 10 and 45, preferably between 9 and 90 and generally between 7 and 200; and wherein the biological material comprises lipids and/or proteins derived from bacterial, mammalian, animal, fungal or plant cells or tissues.

In various embodiments, one or more amphiphilic copolymers are cyclized by a crosslink between the two termini of the copolymer chain. In various embodiments, R1 and R2 taken together form ethyl-dimethylamine-oxide, propyl-dimethylamine-oxide, methylamine, ethylamine, propylamine, ethanolamine, glycine-methyl-ester, or valine methyl ester. In various embodiments, R3 is phenyl substituted by one to five methyl or ($C_2$-$C_{12}$) alkyl groups. Any alkyl group having three or more carbon atoms can be straight chain or branched. In various embodiments, the hydrophilic subunit b of the copolymer and hydrophobic subunit a of the copolymer are present in an equimolar ratio and in a substantially alternating pattern along the linear sequence of the copolymer.

In various embodiments, the copolymer has a number averaged molecular weight of at least 3 kilodaltons. In various embodiments, hydrophilic subunit b contains alkyl groups in place of hydrogen atoms on the hydrocarbon groups. In various embodiments, the nanoparticle has a diameter of 5 nm to about 100 nm, preferably a diameter of about 7 nm to about 50 nm, and more preferably a diameter of about 10 nm to about 30 nm. In various embodiments, R2 is —($C_1$-$C_{12}$)alkyl substituted with halo.

In various embodiments, the biological material is solubilized from brain homogenate, brain matter, biological organ, biological tissue, animal matter, plant matter, eukaryotic cells, prokaryotic cells, or a complex between lipids and membrane protein. In various embodiments, the biological material is bound to a biologically active agent, a drug, a co-factor, a diagnostic probe molecule, an active ingredient of a plant protective product, an active ingredient of a cosmetic product, a contrast agent, a dietary supplement, a nutritional supplement, a molecular label, or an indicator.

Additionally, this disclosure provides a solubilization process comprising:

i) preparing any copolymer disclosed herein by copolymer activation, precipitation, resuspension, centrifugation, fractionation, affinity chromatography, size exclusion chromatography, filtration, or dialysis, ii) diluting such copolymer (in water or deionized water) to a concentration of between 0.1 to 10% w/v, preferably between 0.5 to 3% w/v, iii) combining such copolymer with an aqueous solution containing biological material, thereby solubilizing the hydrophobic material within the biological material into water soluble nanoparticles.

This disclosure also provides a synthetic process comprising:

i) preparing a copolymer described herein by activation of the copolymer by hydrolysis of the original maleic anhydride-based copolymer in the presence of hydrophilic compounds which include the R1-R2 groups, ii) lyophilization or precipitation of the copolymer, resuspension and washing of the precipitated copolymer by centrifugation, and in the case of maleamide copolymers, followed by a subsequent ring closure reaction at a temperature of between 80-150° C.

Furthermore, this disclosure provides a purification process comprising:

i) purification of the copolymer described herein by precipitation, fractionation, affinity chromatography, size exclusion chromatography, filtration, or dialysis, ii) diluting the copolymer to a concentration of between 0.1 to 10% w/v, preferably between 0.5 to 3% w/v, iii) combining such copolymer with an aqueous solution containing biological material and incubating the mixture at a temperature of between 15-50° C. and a pH 5 and 10, thereby solubilizing the biological material into water soluble nanoparticles.

Functional Derivatives of Maleimide (FDM)

Figure 1:
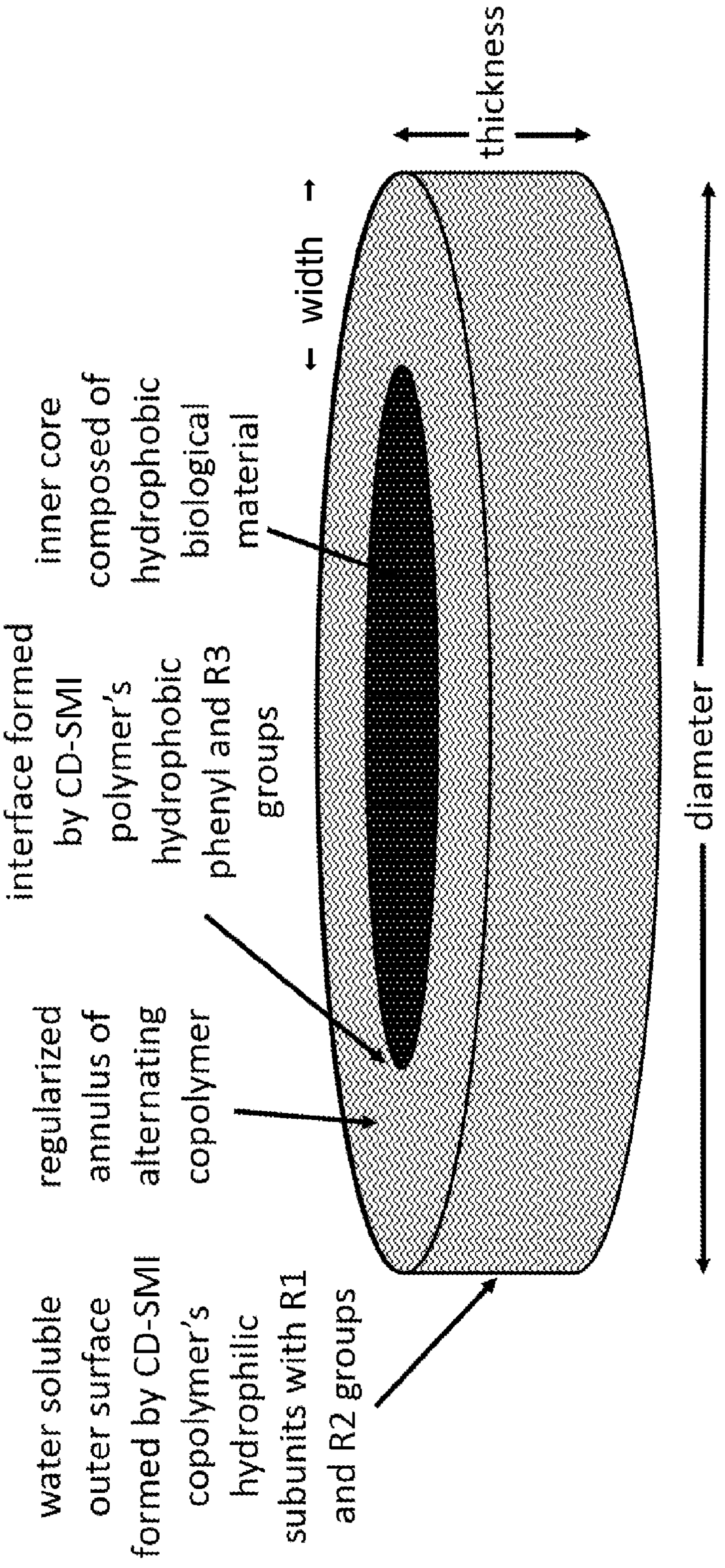
FIG. 1: Depiction of a nanodisc and its components including FDM copolymer. An annulus of FDM copolymer provides an exposed perimeter surface formed by polar subunits which include R1 and R2 groups, which provide functionality, along with a hydrophobic inner interface that contacts the biological material. The regular periodicity of the copolymer backbone provides greater homogeneity and structural resolution. The dimensions of the nanodisc are adaptable to the contents such as encapsulated protein-lipid complexes but include a diameter in the range of 5-100 nm and a thickness in the range of 3-5 nm.
Figure 2:
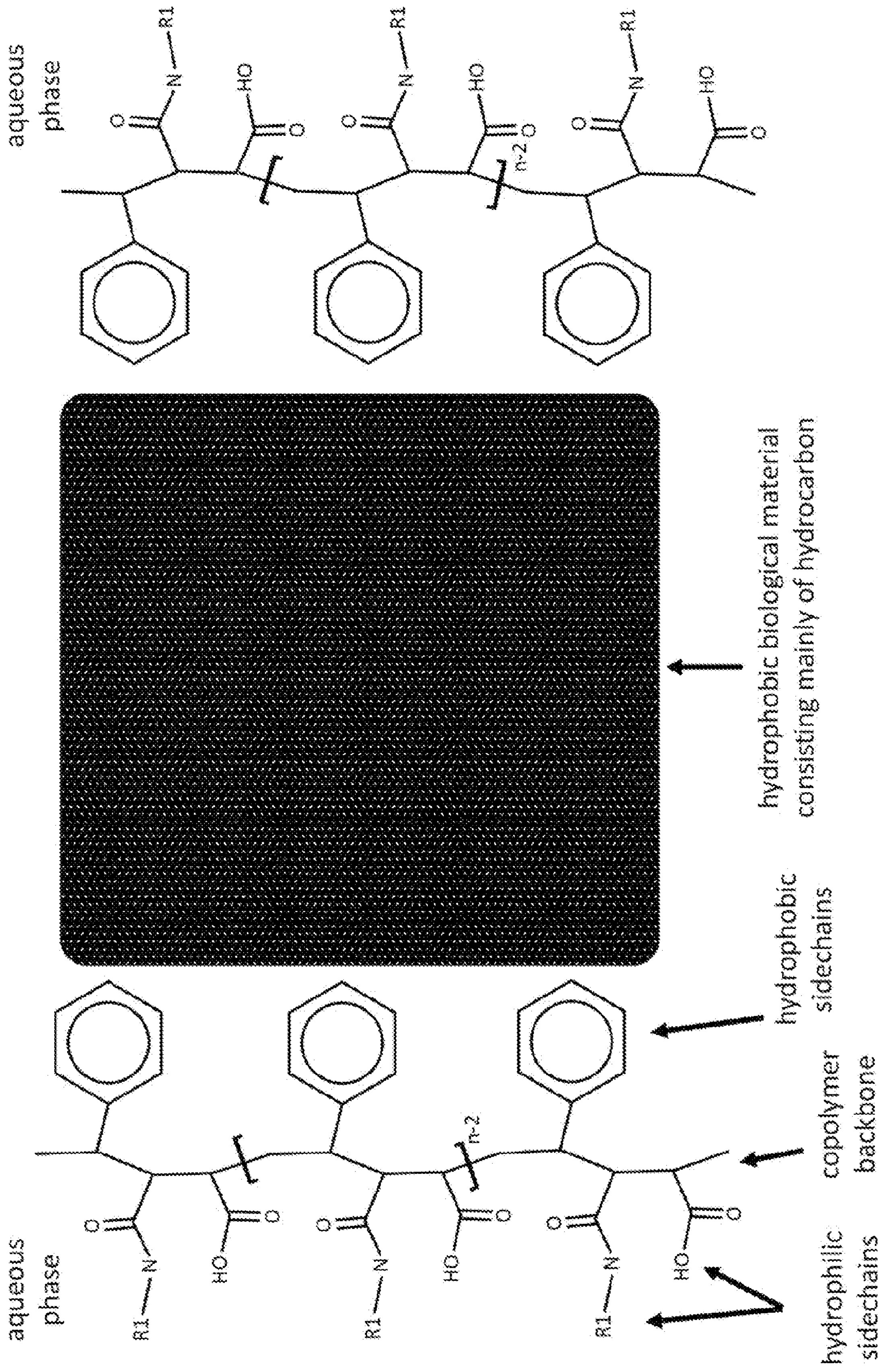
FIG. 2: Cross section of a nanodisc with a boundary of FDM copolymer. The cross-section through the central region of a nanodisc shows the contained biological material, which is composed of largely hydrophobic material, and surrounding copolymer forming an buried interface composed of phenyl groups that provide hydrophobic stabilization and an outer perimeter of maleimide derivative groups with short polar pendant sidechains that interact with water-soluble molecules in solution.

Here we report the invention of a family of custom derivatives of styrene/stilbene maleimide copolymers (FDM) for which a general formula is shown in Scheme 1 and which offer specific utilities and performance advantages for nanodisc formation, purification, detection and analysis. These copolymers have useful properties including reduced compositional heterogeneity due to the presence of hydrophobic and hydrophilic subunits in a ratio that is either 1:1 or 2:1, an alternating pattern of multifunctional side-chain groups that eliminates clusters of excessive charge or hydrophobicity, polar groups that offer excellent aqueous solubility, low reactivity, inclusivity of affinity groups, intrinsic fluorescence, and effective membrane binding and lipid bilayer disrupting activity to stably enclose a segment of lipid bilayer in native nanodiscs with reduced undesirable properties such as nonspecific binding to polycations and proteins. When added to biological material, these copolymers gently bind and release the hydrophobic complexes and release them into a styrene maleimide lipid particle (SMALP), as shown in FIG. 1, with a nanoparticle cross section as depicted in FIG. 2. The nanodiscs are formed in an intact manner such that the arrangement of the lipid and/or protein molecules are preserved and can more readily be isolated and resolved by a variety of assays.

Scheme 1. Structural formual of FDM copolymers (Formula $I^A$ and $I^B$).

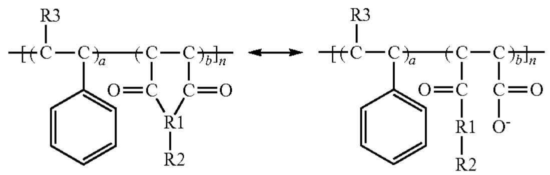

The key elements of FDM copolymers are a carbon backbone unit which is repeated n times, where n is equal to optimally between 10 and 45, preferably between 9 and 90 and generally between 7 ad 200, an R1 group that is typically a nitrogen atom, but in stilbene-based FDM copolymers is optionally an oxygen atom, an R2 group that provides a balance of polarity and hydrophobicity to induce spontaneous, detergent-free formation of stable nanodiscs from membranes with functional features including polyvalent affinity, fluorescence and solubility properties and having the capacity to exit in maleimide and maleamic acid forms by opening and closing of the ring with commensurate effects on backbone flexibility. The R3 group is either. a hydrogen atom or some cases a phenyl group that optionally has alkyl substituents that increase the copolymer's net hydrophobicity and provide greater steric hindrance to the copolymer backbone. In fluorescent forms the hydrophobic and hydrophilic subunits typically alternate wherein optimally "a" = "b" = 1, preferably 1 ≤ a ≤ 1.2, b = 1, and generally 1 ≤ a ≤ 1.4, b = 1 with a heptad copolymer microstructure of hydrophobic (A) and hydrophilic (B) subunits arranged as multiple repeats of AB, thus providing greater homogeneity and visibility. The base copolymers with relevant alternating hydrophobic and hydrophilic subunits are available as commercial products SMA1000 (Cray Valley), SMALP 40005 (Orbiscope), and Xiran SZ40005 (polyscope), along with counterions including $Na^+$, $K^+$ or $NH_4^+$, and they can be synthesized by RAFT polymerization. Alternatively, fluorescence is reduced in forms that have a higher ration of a:b such as 2:1, but these can also contain the various R2 groups grafted onto SMA copolymers, thus reducing net charge and incorporating functional groups such as affinity tags or amino acid moieties. Such copolymers having a subunit ratio wherein 1.7 ≤ a ≤2.3, b = 1 may form semialternating copolymer microstructures of hydrophobic (A) and hydrohilic (B) subunits optimally arranged as multiple repeats of AAB with AA dyads along the copolymer backbone, and could be derived from commercial products SMA2000 (Cray Valley), SMALP 30010 (Orbiscope) or Xiran SZ40005 (Polyscope). The copolymer termini are not specified as they are derived from the initiator and terminator of the copolymer synthesis reaction, respectively, as is ell known to those versed in the art of copolymer synthesis.

Figure 3:
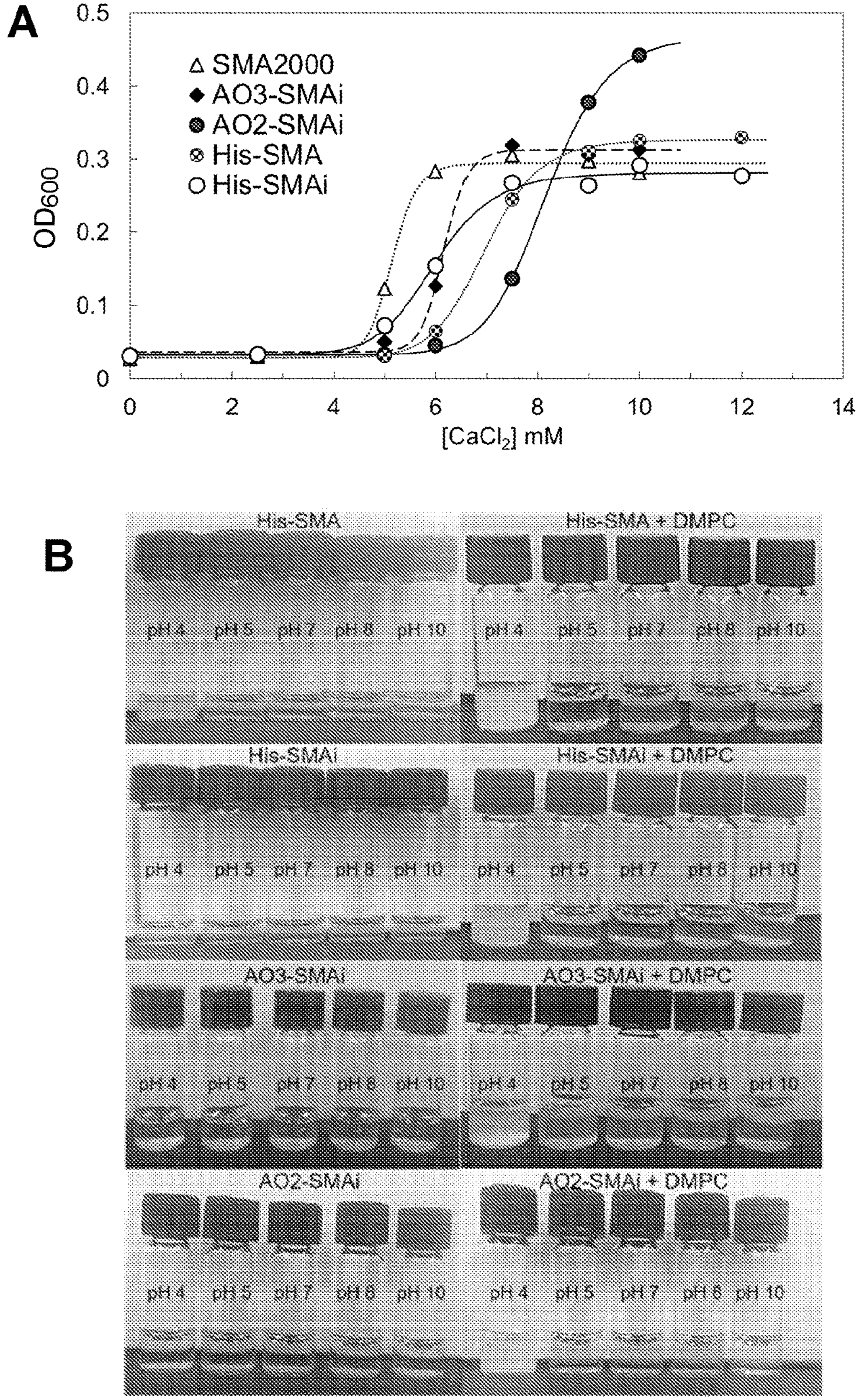
FIG. 3: Solubility of His and AO-derivative SMI copolymers and nanodiscs. (A) Calcium tolerances of AO2-SMAi, AO3-SMAi, His-SMA and His-SMAi and SMA2000 copolymers were quantified. Solutions of each copolymer at 1% w/v were used to collect optical densities at 600 nm and compared with SMA2000 which has a 2:1 styrene to maleic acid ratio, showing the higher divalent cation tolerance of the FDM copolymers. Titrations of stock solutions of NaOH/HCl (1 M), $CaCl_2$ (20 mM) and DMPC (10 mM) were followed by 1 min incubation at room temperature. All spectra were corrected for dilution. (B) Buffers at different pH levels were prepared and polymer (2% w/v stock solution in water) was added to each sample (final concentration of polymer 0.5% w/v) and the optical density (OD) of solutions was monitored at 600 nm with three replicates. The solubility of each indicated copolymer at pH levels from 4 to 10 are shown, as are their abilities to clarify suspensions of vesicles formed by 1,2-dimyristoyl-sn-glycero-3-phosphocholine (DMPC). Each copolymer shows a wide pH tolerance of 5-10 either alone or in the presence of DMPC liposomes, as demonstrated by the clear solutions at these pH levels. His-SMAi, AO3-SMAi, and AO2-SMAi solutions in the absence of DMPC are clear at all pH levels indicated. Hence these FDM copolymers are soluble across a wide pH range but can be removed from nanodiscs by introduction polyvalent counterions such as $Ca^{2+}$ (or $Mg^{2+}$ or $Mn^{2+}$).

The arrangement of molecules within the nanoparticles formed from membranes by FDM copolymers includes a layer of phenyl groups which are packed against the hydrophobic complexes from the biological source material, and an externally facing set of R1 and R2 groups that can interface with the surrounding aqueous solution (FIGS. 2 and 3). The R2 groups provide handles on the FDM copolymer that can be used to balance the hydrophobicity and polarity needed for forming and using readily soluble and resolvable nanodiscs and also for engaging release triggers such as affinity matrices, counter-ions or pH switches to dissociate the copolymer and liberate membrane:lipid complexes from the nanoparticles.

The pendant R2 groups of a FDM copolymer (Scheme 1) can be varied to allow for the presence of functional groups such as amino acid residues, polypeptide sequences or affinity tags such as a Hiss-tag, Flag-tag, Strep-tag, Myc-tag or HA-tag, and the copolymers can exhibit fluorescence which originates from on the alternating phenyl groups (Scheme 2). The hydrophobicity and flexibility in the FDM copolymer can be adjusted by modifying the R3 group, with the presence of a methylated phenyl group here providing greater steric hindrance to backbone for limited rotation, stiffer structure and more regular nanodisc structures.

The claimed FDM derivative copolymers (Scheme 1) are defined as containing the following properties which provide optimized interactions with complex biological materials such as membranes as well as functionalization for improved solution behaviour, purification, detection and resolution:

1) a repeated backbone subunit consisting of alternating groups where the first two carbon atoms are attached to hydrophobic groups and the second two carbon atoms are attached to hydrophilic sidechains and their 1:1 alternating pattern is repeated n times, where n is at least 7 on average such that the copolymer can span for example a membrane, which is typically approximately 35 Angstroms thick, at least once, and hence has a number averaged molecular weight of at least 3 kilodaltons, but could be up to 200 kilodaltons in length and optionally could be cyclized by crosslinks between the two termini of the copolymer chain in order to stably wrap around the circumference of nanodiscs, AND
2) the R2 group contains a polar group, or a $C_1$-$C_{12}$ alkyl group such a methyl, ethyl or propyl group, and when combined with the R1 group and maleimide group, this hydrophilic subunit includes sufficient polarity for water solubility while also providing functionality such as an affinity tag, and could also include halogens such as fluorine, chlorine or bromine which provide enhanced visibility by NMR, electron microscopy or X-ray diffraction (XRD) analysis, AND
3) the hydrophobic subunit contains either one or two phenyl groups where the R3 group is either a hydrogen atom or a phenyl group, which is directly attached to the backbone to form a stilbene group and would increase the hydrophobic contribution to copolymer-membrane interactions while providing steric and rotational restraints, and where the R3 phenyl group could also contain alkyl groups in order to adjust the hydrophobicity or conformational freedom while retaining potential for membrane binding interactions.

The end-groups are optionally not defined chemically as they are well known to those skilled in the art and are part of the moieties used to initiate and terminate the copolymerization reaction. Alternatively, the end-groups could be cyclized by crosslinks between the two termini of the copolymer chain, for example, in order to stably wrap around the circumference of lipids or other biological material (in a helical arrangement or otherwise) to form the nanodiscs described herein. The crosslinks can comprise, but is not limited to, covalent bonds, ionic bonds, hydrogen bonds, Van der Waals forces, or a combination thereof. Crosslinking examples include carbon-carbon or disulfide bonds between the two termini of the copolymer chain, as derived from the initiator and terminator groups used in the copolymerization reaction to synthesize the copolymer chain. Crosslinking is the general term for the process of forming bonds or short sequences of chemical bonds to join two polymer chains together or two ends of a polymer chain together.

The claimed FDM copolymers can either be represented as an open ring maleamic acid form with two polar chains including one with a single carboxylate, or it can be condensed through a dehydration reaction which could be performed at a high temperature in the range of 95-130° C. in dimethylformamide (DMF) to form a closed 5 membered maleimide ring form, or in the case of stilbenes, which contain a more hydrophobic R3 group, the maleimide or maleic anhydride form can be hydrolyzed to form a maleic acid form.

The synthesis of the claimed FDM copolymers can be achieved by methods including reversible addition—fragmentation transfer polymerization (RAFT), atom transfer radical polymerization (ATRP), or nitroxide-mediated polymerization (NMP), iodide degenerative transfer polymerization (IDTP) and conventional radical copolymerization, as conducted in a continuous stirred tank reactor (CSTR), which are known to those who are skilled in the art. The FDM copolymers can also be produced by hydrolysis of an anhydride version of existing SMA(1:1) copolymers, SMA1000 (Sartomer), Xiran SZ4005 (Polyscope) or SMALP XZ40005 (Orbiscope) in the presence of a reactant that contains the desired R1 and R2 groups.

For clarity, not all the hydrogen atoms are explicitly depicted, and these could be replaced by deuterons in some incarnations such as for NMR or small angle neutron scattering (SANS) studies.

The length of the copolymer used depends on the number of subunit repeats (i.e. "n"), and would preferably result in a number averaged copolymer molecular weight of typically between 4 and 10 kDa to form stable nanodiscs, or possibly as small as 3 kDa to increase copolymer exchange rates or larger copolymers of up to 200 kDa which could serve to encompass the hydrophobic material to which it is complexed. The method of producing nanodiscs involves addition of a stock solution of FDM copolymer to a concentration that is typically in the range of 0.5%-3% w/v of the sample of biological material followed by an equilibration period of approximately 30 minutes to several hours typically at a temperature of 20 to 37° C. The purification methods used for nanoparticles formed by FDM copolymers would include the use commercially available affinity resins and size exclusion chromatography resins. The length of the copolymer would result in different nanoparticle dimensions, with the most typically being diameters of 10-30 nm, or potentially 5-100 nm. The thickness of the nanodiscs would typically be 3-5 nm, which is in the range of the thickness of natural membranes. This combination of properties has been found to be most suitable and advantageous for solubilizing a variety of membrane types and lipid: protein assemblies.

Features and Advantages.

Enhanced resolution: The precursor copolymers used to make the claimed FDM copolymers preferably consist of polar and hydrophobic subunits in a 1:1 ratio (i.e. a=b=1) as found in SMA(1:1) copolymer. Consequently, there is a regular alternation of hydrophobic and hydrophilic sidechains in the derivative FDM copolymers (Scheme 1). This is unlike nonalternating SMA copolymers which also form native nanodiscs but instead offer a wider range of statistically defined distributions of styrene and maleic acid subunits that broaden spectral lines and limit resolution. Hence when activated into alkylamide and carboxylic acid groups, the claimed FDM copolymers offer significantly greater homogeneity and structural regularity and hence improved spectral and structural resolution. Consequently, there is a greater likelihood that lipid and/or protein within the resulting nanodisc can be visualized at high resolution and accurately quantitatively assessed for binding activity. This is important as currently available copolymers exhibit so much compositional heterogeneity that they cannot generally be visualized in high resolution structural assays. Alternating copolymers lack the longer clusters of adjacent hydrophobic subunits that mediate undesirable nonspecific interactions.

Moreover, as the claimed FDM copolymers are synthesized in an alternating manner they can be produced with more control and in longer forms than starting from nonalternating SMA copolymers, allowing a more diverse range of products of defined sizes to be generated.

Reduced non-specific electrostatic associations: The replacement of a carboxylic acid within the maleic acid group of SMA copolymers by the formation of a maleimide or maleamic acid group removes a potential charge and point of chelation of polycations thus reducing the non-specific undesirable interactions of the copolymers with divalent cations including $Ca^{2+}$ and $Mg^{2+}$ and some proteins and surfaces. Hence the claimed FDM copolymers are designed to bind productively with membranes to cause nanodisc formation with less nonspecific binding activities associated with more negatively charged SMA copolymers. This is important as the native activity of inserted proteins such as those that rely on divalent cations are more likely to be retained in FDM copolymer nanodiscs which have less polycation binding propensity.

Reduced non-specific hydrophobic associations: The presence of an alternating 1:1 ratio of hydrophobic and hydrophilic subunits means that the relative hydrophobicity of the copolymer is reduced. Sufficient hydrophobicity to allow productive insertion into the membrane is ensured in FDM copolymers by the presence of alkyl chains in the polar group. Together with the avoidance of hydrophobic group clusters such as the AAA triads that are found when starting from nonalternating SMA copolymers this reduces the propensity of FDM copolymers for undesirable non-specific hydrophobic interactions with some proteins and surfaces, and increases the ability of the FDM copolymer to solubilize native structures intact.

Adjustable backbone flexibility: The presence of either a hydrogen atom or alkyl-substituted phenyl group at the R3 position allows the backbone flexibility to be controlled through steric effects, allowing conformationally restrained and more regularized nanodisc structures to be formed.

Tunable hydrophobicity: The presence in R2 of a net charge of between −1 to +1, between 0 to about 12 carbon atoms, between 0 to 2 nitrogen atoms, 0 or 1 sulfur atoms, and 0 or 1 phosphate atoms and phenyl group substituents including alkyl groups, —OH, —NH2 or halogens allows the specific membrane interactivity of the copolymer to be fine-tuned. This is important for protein states that are especially labile and require a gentle solubilization process, and also provides elements that can be visualized in some assays such as NMR, electron microscopy (EM) and XRD.

Multifunctionality: The presence of functional groups at the R2 groups of the copolymer allows purification of nanodiscs using affinity groups that bind resins such as nickel-NTA, while presence of a fluorophore allows detection of the copolymer and alterations of its environment due to membrane interactions and associated conformational changes.

Biocompatibility: The presence of single or multiple amino acid residues that can be extended into polypeptides or protein sequences at the R2 group allows biological properties to be integrated.

Fluorescence: The intrinsic fluorescence of classes of FDM copolymers with alternating styrene and maleimide-derived subunits means that bulky fluorophores do not need to be added, precluding any ancillary effects on solubility, membrane insertion. The FDM sidechains, when of a small size, reduce opportunities for nonspecific interactions or other liabilities. Such FDM copolymers provide a signal that can be readily seen by fluorescence spectroscopy under a diversity of solution conditions and when complexed with nanodiscs. This allows a convenient way to measure copolymer concentrations or could also be used to monitor molecular interactions.

Resolvable halogens: The presence of halogens in R2 or phenyl groups allows the copolymer to be detected, e.g. by fluorine-19 NMR spectroscopy, by XRD studies of brominated copolymer, or by cryo-electron microscopy of memtein complexes. This allows the structures of the copolymer to be detected in nanodiscs by a wider array of structural methods, providing increased accuracy and resolution.

Increased homogeneity: The presence of alternating polar R2 chains with 12 or fewer carbon atoms allows accessible hydrogen bonding and water solubility to be retained while providing sufficient hydrophobicity to bind the membrane through the adjacent phenyl groups. Longer R2 chains could introduce excessive flexibility and liability for efficient aqueous solubilization of membranes into homogeneous and resolvable nanodiscs in biological samples. Reduction of the net charge on the R2 groups allows larger nanodisc formation due to reduced charge repulsion and also leads to reduced polycation binding and more effective membrane insertion. The balance of size, polarity and hydrophobicity of this R2 group are needed for the production of broadly useful copolymers in physiological solutions and for production of more readily resolvable native nanodiscs.

Controllable membrane fragmentation: The presence of an optimal balance of hydrophobicity and polarity in FDM copolymers promotes efficient fragmentation of the membrane into nanodiscs at concentration of around 0.5 to 3% w/v in an aqueous medium. In each repeat the presence of no more than an absolute net charge of 1 under physiological solution conditions such as pH 5-9 provides a wide of breadth aqueous solubility. Greater charge density would increase undesirable binding to polyvalent cations such as $Ca^{2+}$, $Mg^{2+}$ or $Mn^{2+}$ and charged patches on some surfaces and proteins. The length of the copolymer also influences the solubilizing and stabilization properties, as well as size of the nanodiscs, as is understood by those familiar with the production of nanodiscs from copolymers including SMA.

Scalable production methods for synthesis of FDM copolymers include RAFT methods and scalable purification methods of nanoparticles produced with FDM copolymers including use of commercially available affinity resins and size exclusion chromatography systems.

Here we show that FDM copolymers offer improved utility for functional nanodisc production and analysis, features not present in other copolymers shown previously to form nanodiscs. The following Tables and Figures are included to illustrate certain embodiments or aspects of the invention in more detail. However, those who are skilled in the art will understand that these illustrations represent specific examples or aspects that may be extended to other examples or aspects of the invention.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1.

Fluorescent Custom Derivatives of FDM Copolymers

A series of fluorescent FDM copolymers were designed that provide convenient detection, higher sequence homogeneity, affinity groups, and broad utility under a range of solution conditions such as pH and divalent cation levels. Compounds 1 and 2 incorporated histamine as a functional group within their polar sidechains (Scheme 2), while compounds 3, 4, 5 and 6 include an amine oxide group in their polar sidechains (Schemes 3, 4).

Scheme 2 Structures of His derivatives of alternating styrene maleimide.

1

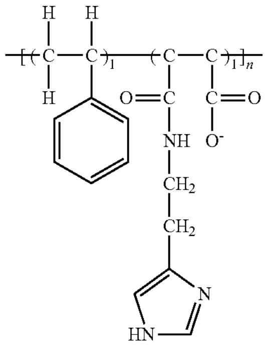

2

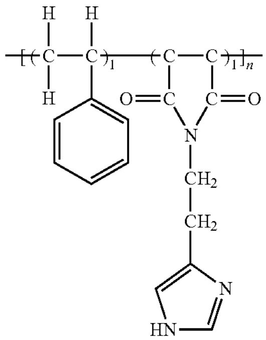

Poly(styrene-alt-maleamic acid-histamine) (His-SMA, compound 1. left) and poly(styrene-alt-maleimide-histamine) (His-SMAi, compound 2, right) are shown, where the relative orientation of the imidazole ring and maleimide group yields fluorescence and the histamine ring is positioned accessibly in order to bond to metal affinity resins such as nitrilotracetic acid (NTA) for convenient purification. The molecules 1 and 2 can be interconverted by maleimide ring opening and closing reactions to adjust the charge density of the copolymer and nanodisc annulus.

Scheme 3 Structures of amine oxide derivatives of alternating sytrene maleimide.

3

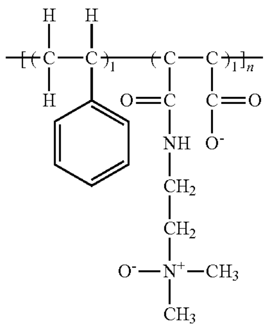

4

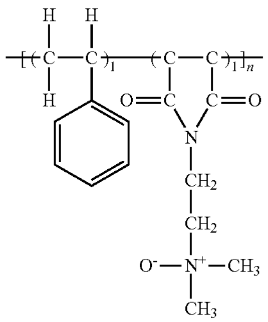

Poly(styrene-alt-maleamic acid-ethyl-dimethylamine-oxide) (AO2-SMA, 3, left) and poly(styrene-alt-maleimide-propyl-dimethylamine-oxide) (AO2-SMAi, 4, right) contain proximal amine oxide and malemide groups that act as electron acceptor and donor groups and fluoresce in a manner like compounds 1 and 2.

Scheme 4 Chemical structures of propyl-dimethylamine-oxide derivatives of alternating styrene maleimide.

5

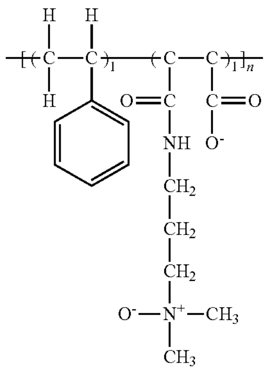

-continued

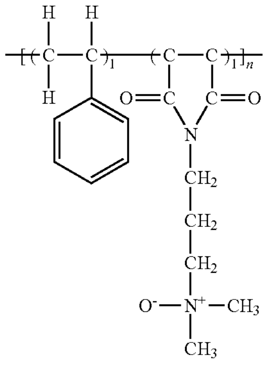

6

Poly(styrene-alt-maleamic acd-propyl-dimethylamine-oxide) (AO3-SMA, 5, left) and poly(styrene-alt-maleimide-propyl-dimethylamine-oxide) (AO3-SMAi, 6, right) are shown, wherein the relative orientation of the amine oxide and maleimide group form a fluorophore like compounds 3 and 4.

-continued

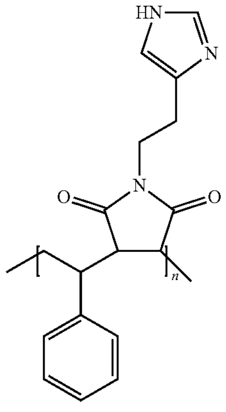

His-SMAi (2)

Scheme 5 Schematic of the His and AO derivative copolymer synthesis.

A

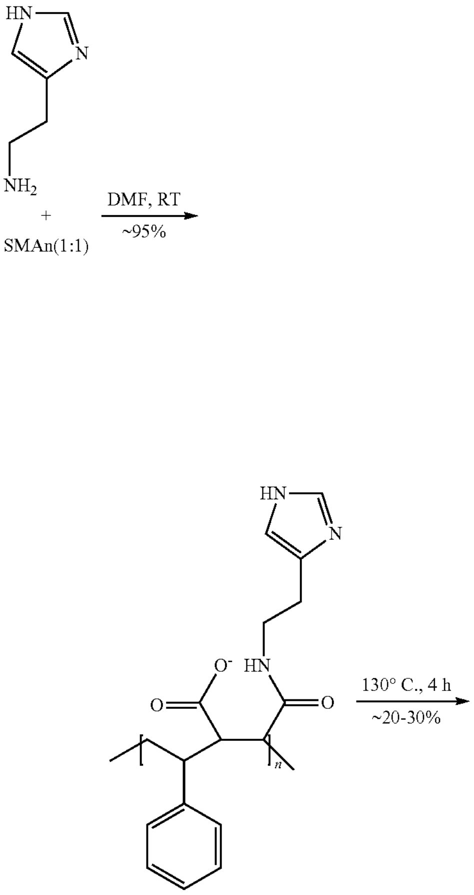

His-SMA (1)

B

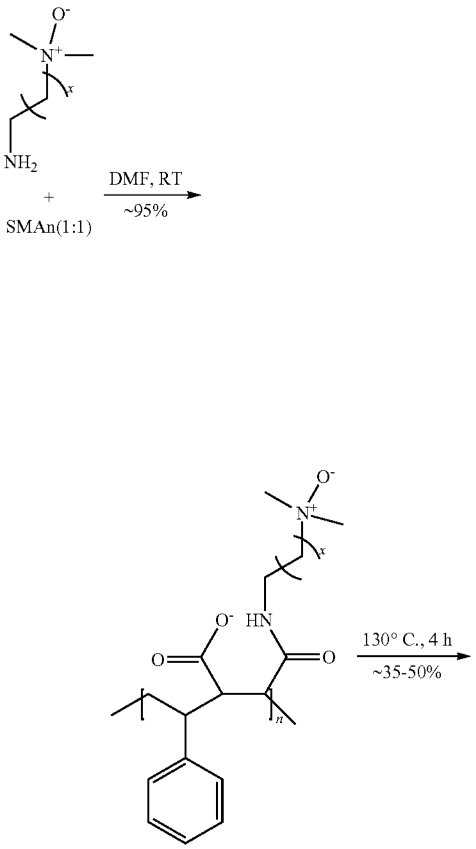

x = 1 AO2-SMA (3)
x = 2 AO3-SMA (5)

-continued

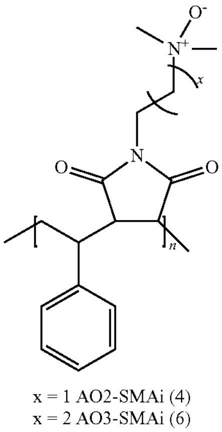

x = 1 AO2-SMAi (4)
x = 2 AO3-SMAi (6)

(A) Grafting of histamine onto SMA(1:1) leads to His-SMA copolymer (1) with and open ring configuration that can be converted to the closed ring form (His-SMAi), 2) by a dehydration reaction. His-SMA copolymer product 1 was synthesized by slowly adding 9 mmol of histamine (dissolved in methanol) to SMAn(1:1) in DMF for 10 hours at room temperature (RT). The product was precipitated with diethyl ether/water, dissolved in 1M NaOH, pH adjusted to 8 and lyophilized. (B) The AO reagents, 1,3-propanediamine, N,N-dimethyl, N-oxide and N,N-dimethyl ethyl, were synthesized by oxidation of their corresponding tertiary amines N,N-dimethyl, 1,3-propanediamine and N,N-dimethylethylenediamine (Sigma). Partial oxidation of the tertiary amine containing ethyl (x = 2) or propyl (x = 3) alkyl groups in $H_2O_2$ yields the AO products. Addition of the alkyl diamine, N,N dimethyl n -oxide sidechain onto SMAn(1:1) followed by dehydration by high temperature (i.e., 95° C., 12 hr or 130° C., 4 hours in the presence of phosphorus pentoxide) was used to close the maleamic ring and to synthesize products 4 and 6, as shown by FT-IR and NMR spectra to be partially complete.

Imidazole-containing tags are widely used to purify recombinant proteins, but not to purify unmodified membrane protein complexes or memteins, providing a basis for the presence of multiple histamine groups on the polar sidechain to enable polyvalent affinity purification. Histamine (His) groups were grafted onto the maleic anhydride group (Scheme 5) and allow the resulting His-SMA copolymer to bind to metal ion affinity resins, thus allowing enable purification of endogenous proteins. The product 1 includes a negatively charged monomer that can bind metals and polycations. Furthermore, product 1 can undergo a dehydration reaction at high temperatures to generate 2 which is zwitterionic and has closed maleimide rings, thus reducing nonspecific interactions of the copolymer product, as confirmed by FTIR and NMR spectra.

Due to their zwitterionic properties, lack of negative effects on protein functions and low ecotoxicity, amine oxide moieties are useful features of widely used surfactants such as lauryldimethylamine N-oxide (LDAO). Hence dimethyl amine oxide groups were attached to alternating SMA(1:1) copolymer with ethyl and propyl linkages to form A02-SMAi and A03-SMAi derivatives, respectively (Scheme 5). Both the open ring maleamic acid and closed ring maleimide forms were generated as they contain either acidic or zwitterionic polar groups, respectively, in order to test the concomitant effects on solubility in the presence of divalent cations (FIG. 3) and pH profiles. The amine oxide can be formed from an alkyl diamine, N,N dimethyl n-oxide sidechains containing ethyl (x=1) or propyl (x=2) alkyl groups after partial oxidation of the related tertiary amine in $H_2O_2$. Grafting the amine oxide reactants onto the alternating SMA(1:1) copolymer followed by dehydration yields the products 3 and 5 that could be converted to the closed ring form 4 and 6 by a dehydration reaction. The latter products showed bands at 968 $cm^{-1}$, which corresponds to stretching vibrations of the N—O group, indicating the conjugation of alkyl-dimethylamine-oxides in FT-IR spectra, 1100 $sm^{-1}$ bands which are consistent with the stretching vibration of the C—NO bond, and bands at 1703 cm $^{+1}$ indicates formation of the maleimide ring. NMR spectra of the AO2-SMAi and AO3-SMAi products 4 and 6 exhibited resolvable $^{13}C$ and $^{1}H$ resonances for the sidechain groups.

Figure 4:
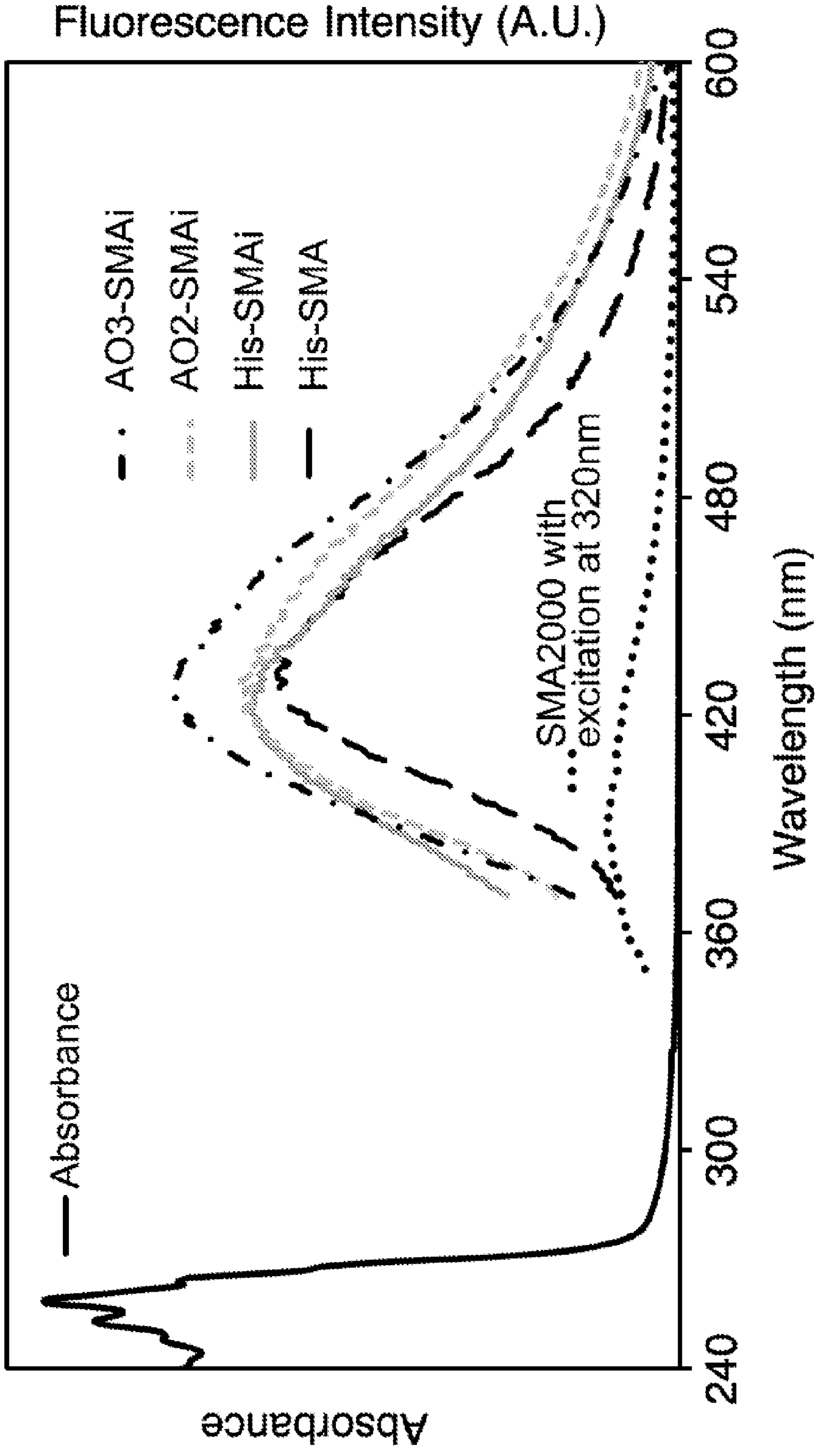
FIG. 4: UV-Vis absorption (right axis) and fluorescence emission spectra (left axis) of modified SMA copolymers (1% w/v) in Tris buffer, pH 8 upon irradiation of AO-SMA and His-SMA copolymers with 320 and 350 nm UV light, respectively, exhibiting an average Stoke's shift of ~140nm. The spectrum of SMA2000 is shown upon excitation at 320 nm. Given the maximum absorbance of these copolymers (between 260-280 nm), the Stokes shifts of the modified copolymers were estimated to be about 146 nm.
Figure 5:
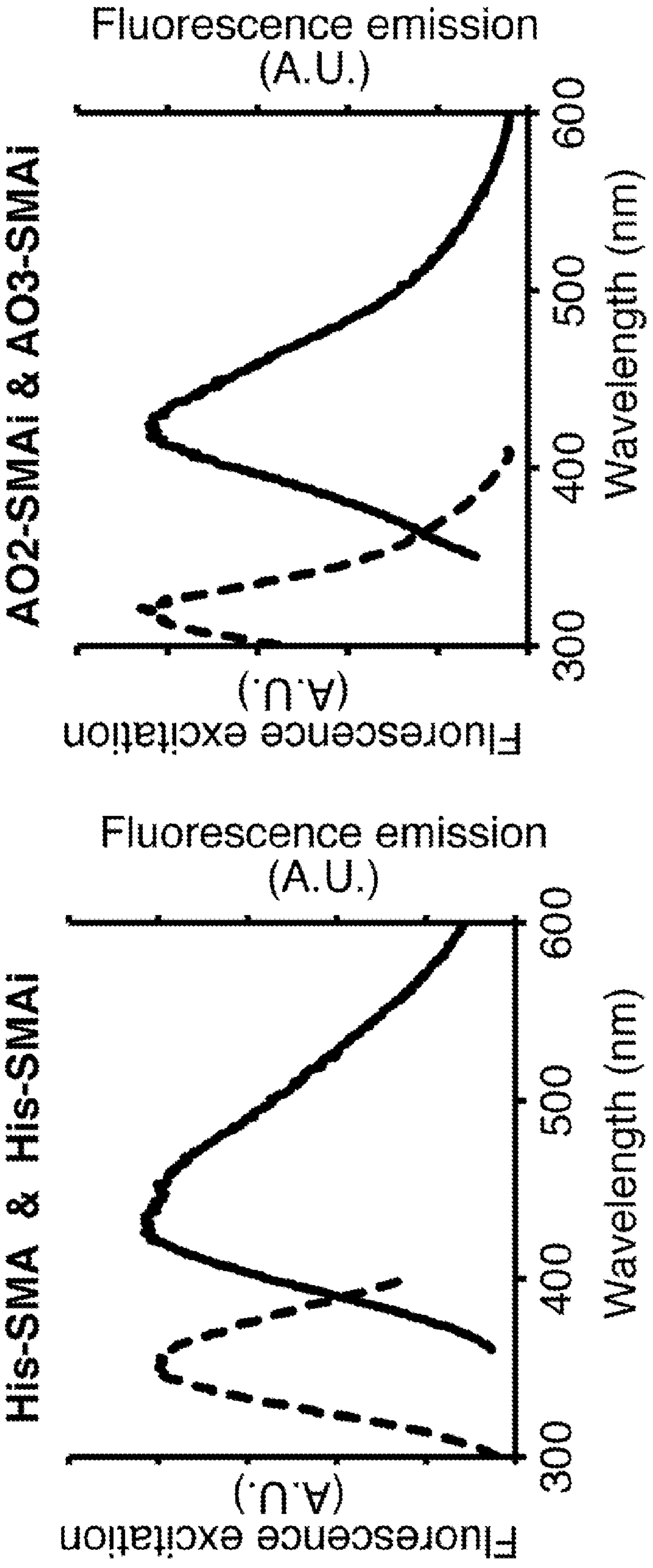
FIG. 5: Excitation and emission spectra of AO-SMA and His-SMA copolymers collected as in FIG. 4. Stock solutions of co polymers were prepared in deionized water and diluted to desired concentrations. Their emission fluorescence spectra (bandwidth 10 nm) were monitored at excitation wavelengths 350 nm and 320 nm (bandwidth 5 nm) on a Varian Cary Eclipse spectrophotometer

Fluorescence of FDM copolymers. Being able to track and monitor copolymers and resultant nanodiscs is desirable and not readily feasible with existing SMA copolymers due to overlap of their optical density signals with those of proteins. Both AO-SMAi products with ethyl and propyl sidechains share similar excitation and emission profiles with a maximum emission ~423 nm upon excitation at 350 nm (FIG. 4). The maximum excitation wavelength of His-SMA shifts towards 320 nm with little change in their maximum emission wavelength. Given the maximum absorbance of these copolymers (between 260-280 nm), the Stokes shifts of copolymers are approximately 146 nm (FIG. 5).

Figure 6:
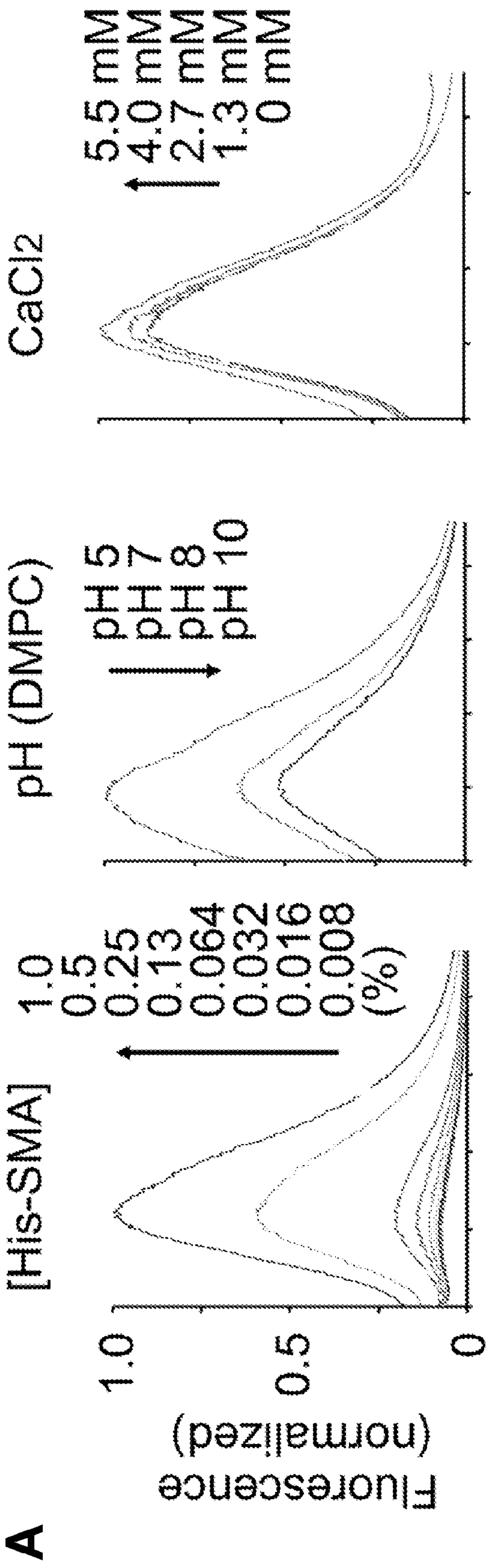
FIG. 6: Fluorescence spectra of His-SMAi(A), His-SMA (B) AO2-SMAi(C) and AO3-SMAi (D) form under different copolymer concentrations, pH ranges (5-10), in the presence of DMPC vesicles, $CaCl_2$. (E) The fluorescence intensities of different variants of His-SMA and AO-SMA copolymers show linear relationships with their concentrations. Stock solutions of copolymers were prepared in deionized water and diluted to desired concentrations. Emission fluorescence spectra (bandwidth 10 nm) were monitored at excitation wavelengths 350 nm and 320 nm (bandwidth 5 nm) on a Varian Cary Eclipse and ATR-FTIR (Nicolet 8700) spectrophotometers. The effects of titrating in stock solutions of NaOH/HCl (1 M), $CaCl_2$ (20 mM) and DMPC (10 mM) followed by 1 min incubation at room temperature on the emission spectra of each sample were examined after correction for dilution.
Figure 6:
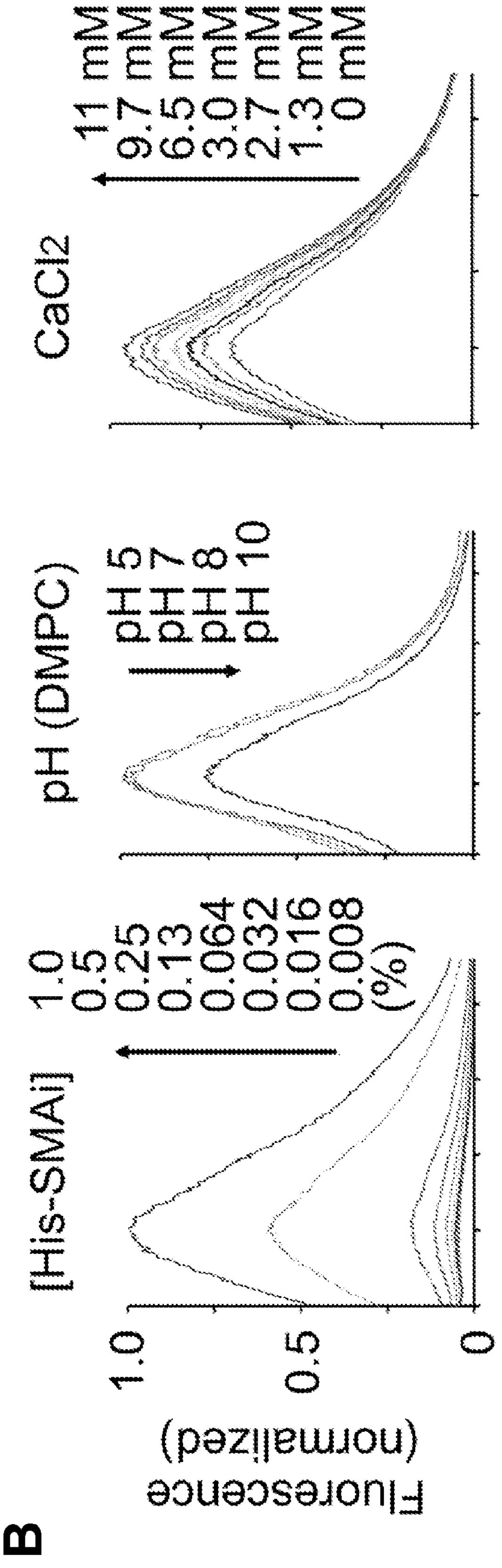
Figure 6:
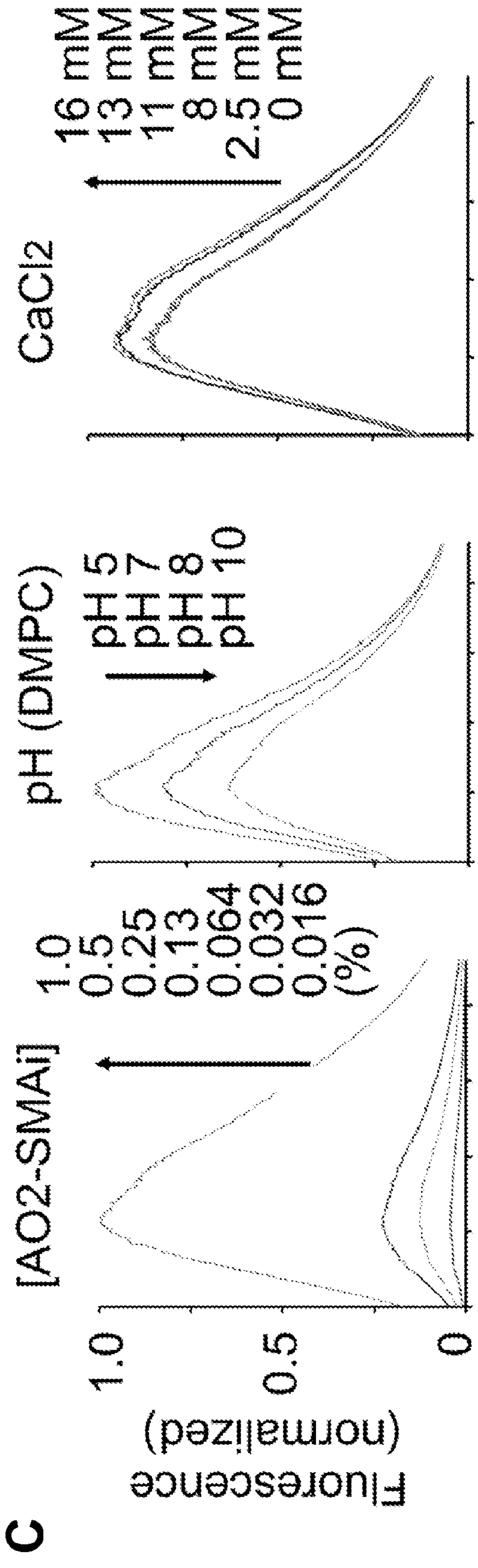
Figure 6:
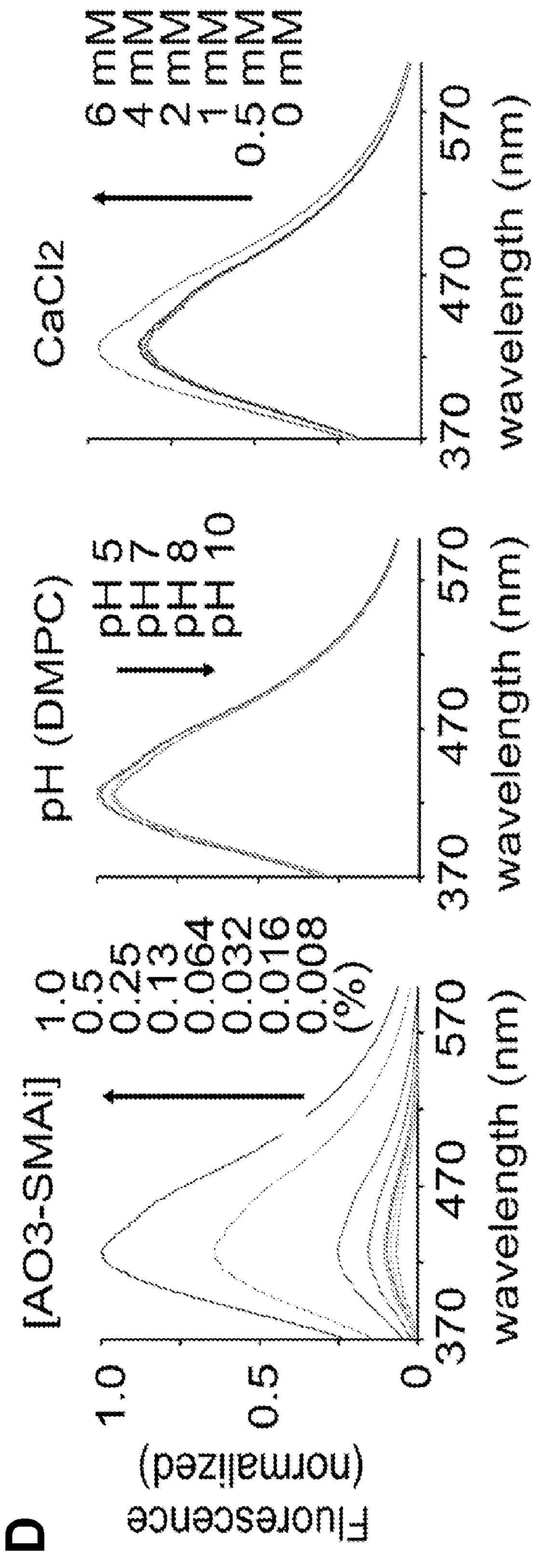
Figure 6:
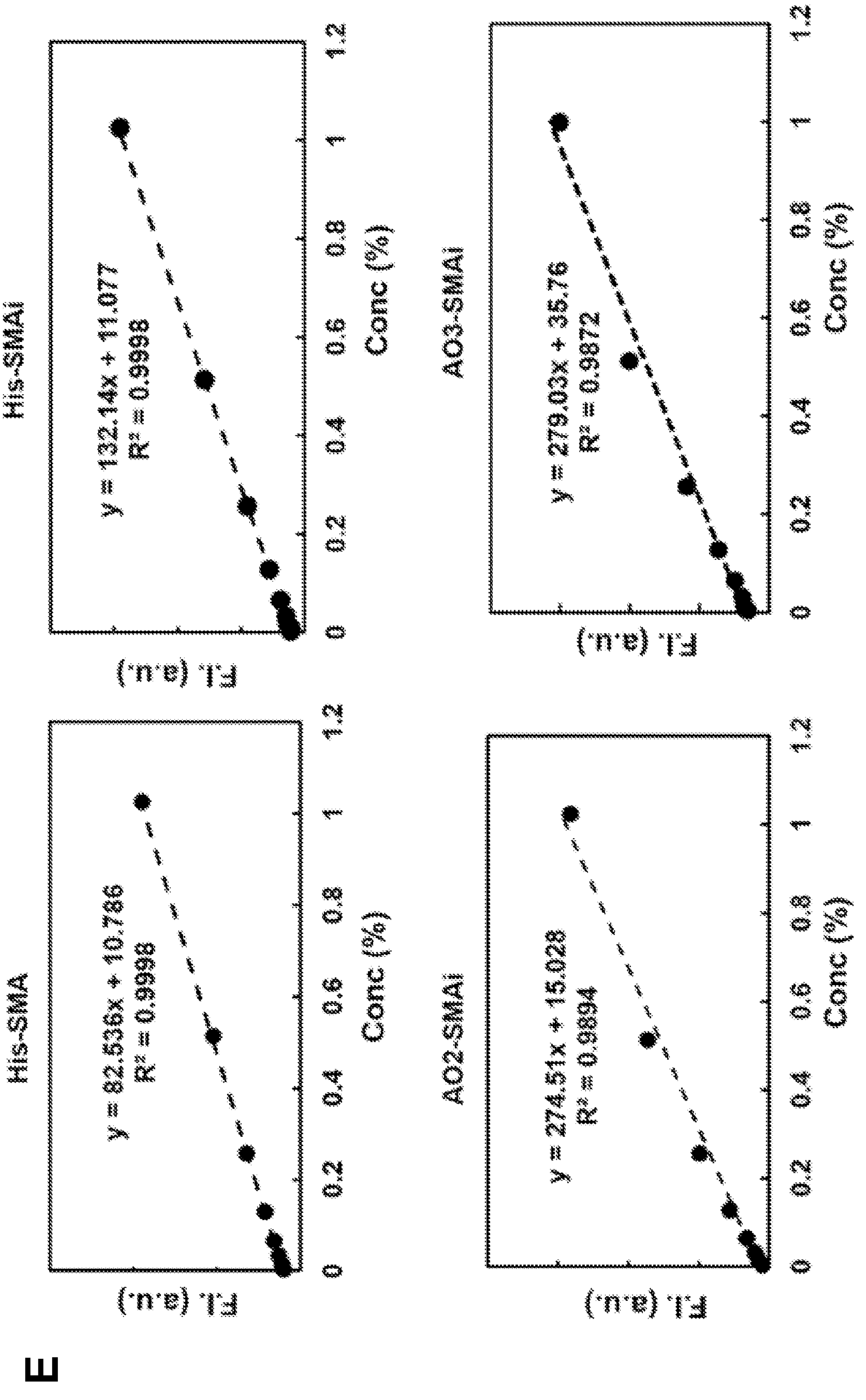

The robustness of the fluorescence signals of each copolymers was explored under conditions that are typically used to form or assay native nanodiscs. The fluorescent emissions are linearly related to the copolymer concentration (FIG. 6). In addition, the signals are maintained in the presence of DMPC vesicles over a range of pH values. The maximum fluorescence wavelength is consistent, although the intensities increase as the pH is reduced from 10.0 to 5.0, while titration with $CaCl_2$ has little effect on the fluorescence signal of the soluble copolymer (FIG. 6). Hence, fluorescence signals of these FDM copolymers allow their concentrations to be readily quantified in free and membrane-bound states under a variety of solution conditions.

Figure 7:
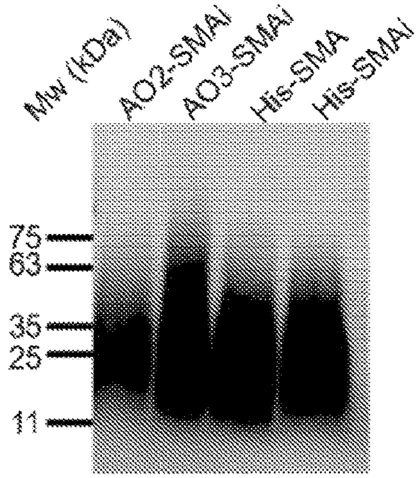
FIG. 7: Reactivity of AO2-, AO3- and His-SMA copolymers with anti-histamine antibody. Polyclonal rabbit anti histamine antibody (Sigma) is shown to recognize the indicated copolymers as evident by gel elctrophoresis and immunoblotting. Polyclonal rabbit anti histamine antibody (Sigma) was (diluted 1:13,000) in fish gelatin (2% w/v) in TBS and incubated for one hour at room temperature. After three washes with TBS and Tween20 (0.1% v/v), the membrane was incubated with HRP conjugated goat anti-rabbit secondary antibody for an hour.

Antibody recognition: The His derivatized SMA(1:1) can also be recognized using an anti-histamine antibody (FIG. 7), which was used to demonstrate that these copolymers interact with Ni-NTA resins and can be eluted with imidazole buffer (50 mM and AO-substituted SMA copolymers display almost no interaction. Hence, these multifunctional substituents can be used as both affinity tags, fluorescent signals and antibody epitopes.

Figure 8:
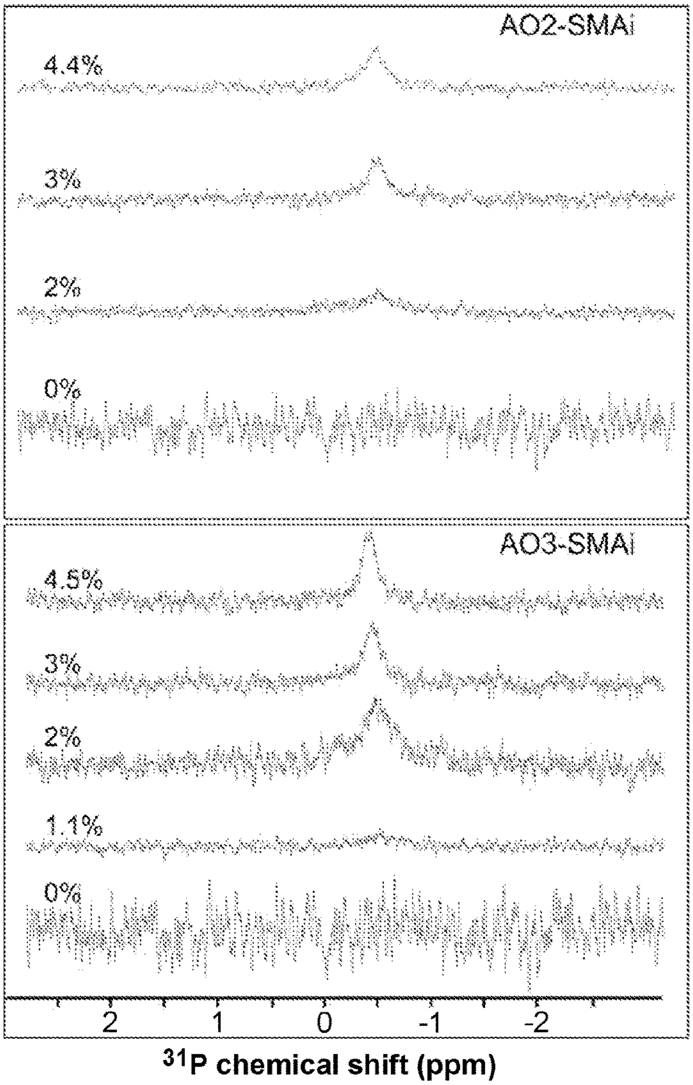
FIG. 8: Vesicle solubilization into nanodiscs by FDM copolymers based on $^{31}P$ NMR spectra. The spectra show the interaction between copolymers AO2-SMAi, AO3-SMAi, His-SMA, and His-SMA with DMPC lipid vesicles in 90% $H_2O$, 10% $D_2O$. The $^{31}P$ NMR signals of the lipid molecules sharpen upon increasing the concentration of SMA copolymers as vesicles are turned into nanoparticles. The $^{31}P$ NMR spectra of lipids were acquired using a Varian VNMRS 600 MHz NMR spectrometer and 5 mm indirect detection broadband z-PFG probe. Experiments were performed with a 20 ms 90° pulse, broadband $^1H$ WALTZ decoupling, 1024 scans, and 1 s repetition delay. NMR spectra were referenced by setting the $H_3PO_4$ (100%) signal to 0 ppm.
Figure 8:
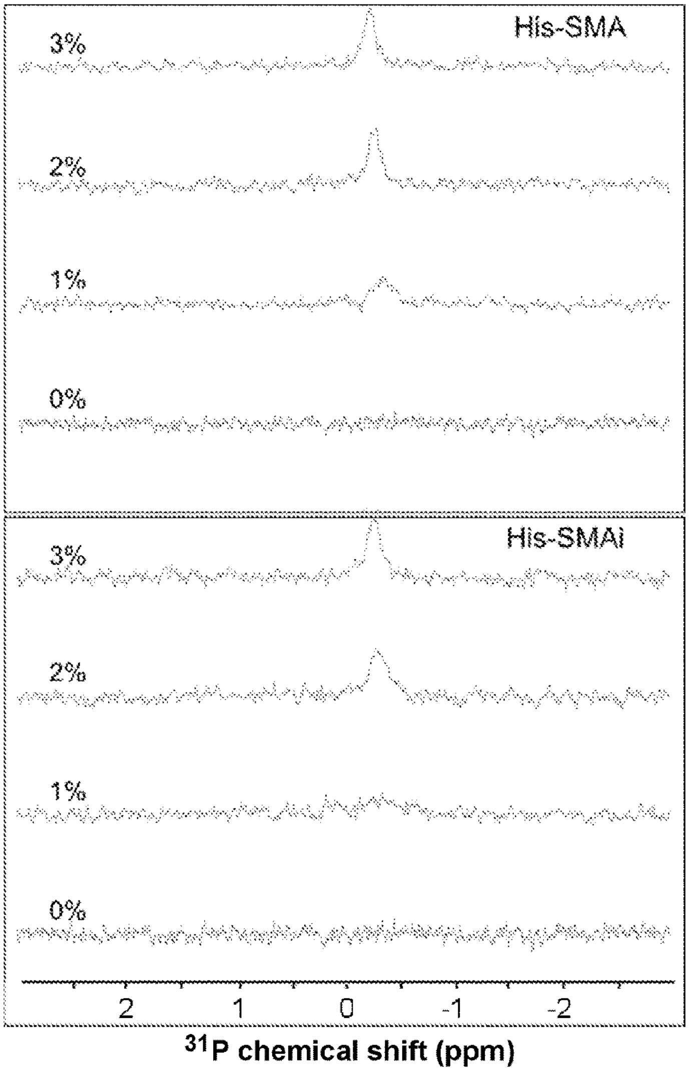

Membrane solubilization activity: The dispersal of vesicles into rapidly tumbling nanodiscs can be seen by $^{31}P$ NMR. The transition of imperceptibly broad $^{31}P$ resonances of DMPC into sharper signals indicates critical copolymer concentrations for the AO— and His-derivatized SMA(1:1) copolymers (FIG. 8). This is also the level at which the copolymers clarify otherwise turbid solutions of lipids or membrane fractions (FIG. 6), thus cross-validating the concentration range needed for membrane solubilization.

Figure 9:
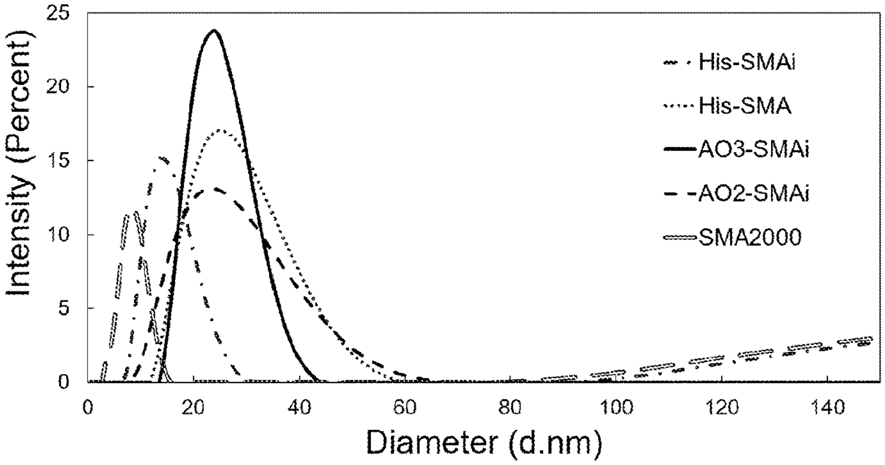
FIG. 9: Dynamic light scattering (DLS) measurements showing the sizes of nanodiscs formed by AO2-SMAi, AO3-SMAi, His-SMA and His-SMAi treatment of DMPC vesicles. SMA2000 was used a control. The diameters of the populations of nanodiscs in 1%, Tris 10mM, pH 8, 100mM NaC1 are shown in nanometers. The average size (in nanometer) of nanodiscs formed of DMPC lipid vesicles containing different amount (% w/v) of AO- and His-SMAs was measured at 25 ° C. using a Zetasizer Nano ZSP (Malvern Panalytical, UK) with 3 mm cuvettes. All experiments were repeated three independent times, each with a 12 scan average. Data was analyzed using a Zetasizer software version 7.12.

Nanodisc sizes: Although conventional SMALPs are ~10 nm in diameter, many membrane assemblies exceed this size. The nanodiscs made with the AO and His-modified copolymers were expected to be larger due to the reduction of net charge. The dimensions of discs solubilized from DMPC vesicles by 1, 4, 5 (1% w/v) were found to be about 24, 16, 21 nm, respectively, by dynamic light scattering (DLS) experiments (FIG. 9A). As such, they are approximately twice the size of discs typically reported for SMA (2:1) and SMA(3:1) series, and could more readily accommodate larger membrane:protein assemblies. The average particle size can be adjusted by altering the ratio of copolymer to lipid (FIG. 9B), with broader size distributions are evident at low and high copolymer concentrations (Table 2).

TABLE 2

Size distribution of nanodiscs formed by AO2-SMAi, AO3-SMAi, His-SMA and His-SMAi copolymers at different copolymer ratios concentrations. The nanodiscs are generally 15-30 nanometers in diameter at the general working copolymer concentration of 1%, with larger membrane nanoparticles appearing at lower concentrations of copolymer.

| | SMA concentration (w/v) | | | |
|---|---|---|---|---|
| Polymer | 0.2% | 0.4% | 0.6% | 1% |
| His-SMA | 28.9 ± 0.3 | 25.6 ± 0.35 | 24.4 ± 0.52 | 24.5 ± 0.17 |
| His-SMAi | 27.04 ± 0.8 | 24.3 ± 0.2 | 24.8 ± 0.3 | 16.5 ± 0.2 |
| AO2-SMAi | 28.7 ± 0.5 | 25.5 ± 0.06 | 25.9 ± 0.4 | 21.3 ± 0.2 |
| AO3-SMAi | 72 ± 0.3 | 55 ± 0.3 | 32.8 ± 0.15 | 28.2 ± 0.1 |

Figure 10:
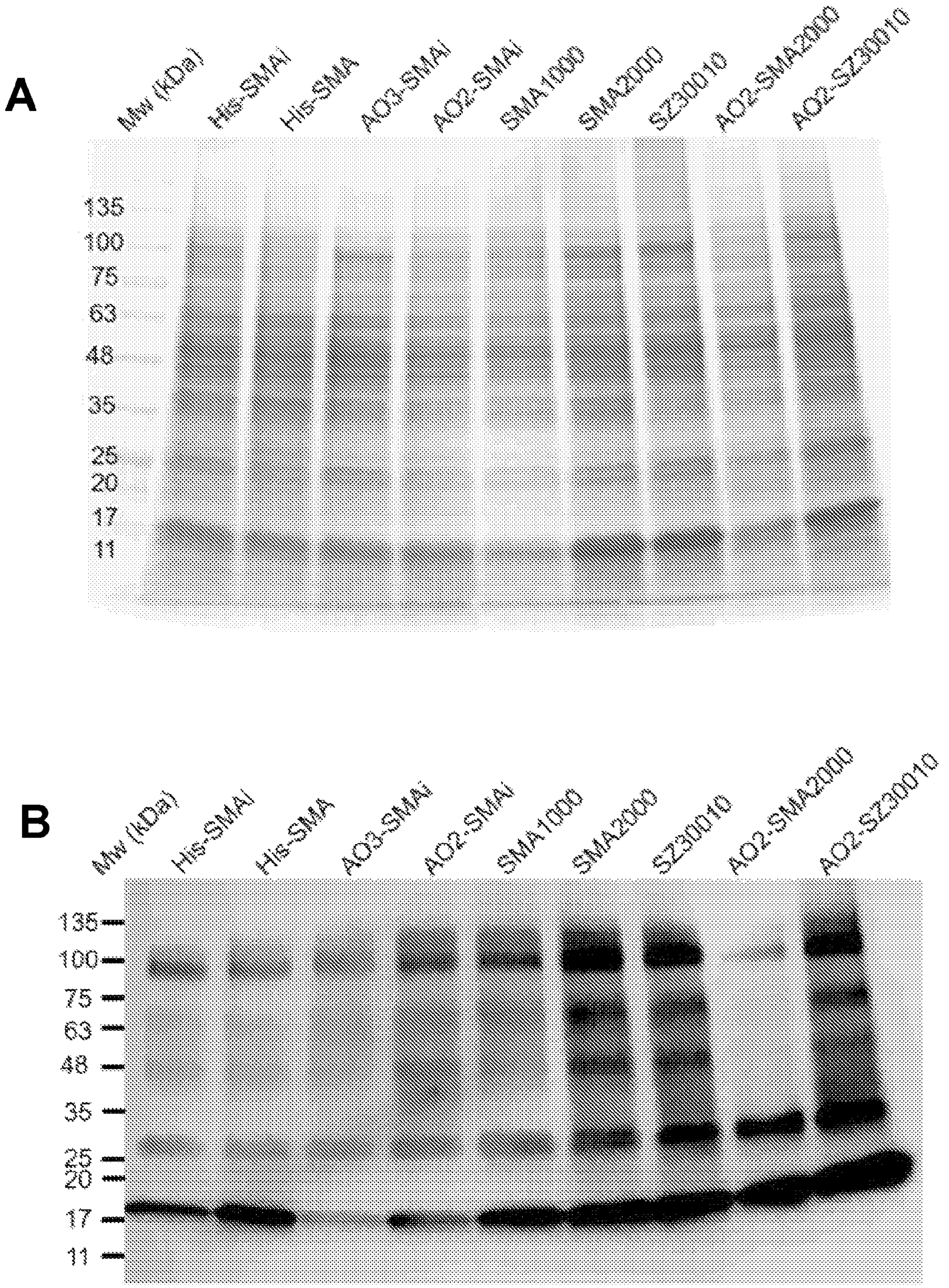
FIG. 10: The efficiency of different FDM copolymers (2% w/v) in solubilizing biological membranes were compared. The SMA2000 and SZ30010 copolymers have SMA ratios of 2:1 and 2.3:1, respectively, and are also present in modified forms with an AO2 group on the R2 position. (A). The SDS-PAGE gel shows total crude proteins extracted from *E. coli* outer membrane by different copolymers before purification. (B).

Native nanodisc formation. Biological membranes present ordered bilayers packed with a variety of lipids and proteins, and hence are more challenging for SMA to penetrate. Nonetheless, the AO— and His-modified SMA copolymers (2% w/v) efficiently solubilize *E. col* membranes at levels comparable to SMA2000 and SZ30010 (FIG. 10). The Ao2 derivatives of SMA2000 (AO2-SMA2000) and SZ30010 (AO2-SZ300010) were also effective solubilizers, with the latter releasing the most total membrane proteins from outer membranes into the soluble fraction while unmodified SMA(1:1) delivered the least. Thus, the FDM copolymer sidechains can be grafted onto different maleic acid-containing copolymers in order to solubilize biological membranes into detectable, purifiable nanodiscs.

Membrane protein purification: The purification of an *E. col* outer membrane protein from its native environment was tested using FDM copolymers. The PagP protein was over-expressed in *E. coli* with an N-terminal signal sequence for delivery into the outer membrane, and a C-terminal His6 tag was incorporated to aid in purification. The outer membrane was isolated by sucrose density gradients and solubilized using the various copolymers followed by purification by Ni-NTA resin and gel filtration based chromatography (FIG. 11). The PagP protein appeared to be mainly monomeric after purification with 1. The AO2 and AO3 derivatives yielded distinctive ladders of multimeric states, consistent with earlier PagP studies (FIG. 12).

Nanodisc dimensions. The structures of affinity-purified PagP nanodiscs made using AO—0 and His-SMA copolymers were examined by transmittance electron microscopy (TEM) imaging. This revealed a population of round discs with diameters of around 20 nm (FIG. 13), which is consistent with the sizes measured by DLS (FIG. 9) and double the diameter of conventional SMALPs.

Example 2

Serinol-containing copolymers 7 and 8 (Scheme 6) were prepared (Scheme 7) and their solubilization activities and functionalities were demonstrated using liposomes (FIG. 14), fluorescence assays (FIG. 15) and bacterial protein PagP (FIG. 16).

Scheme 6 Chemical structures of serinol derivatives of alternating styrene maleimide.

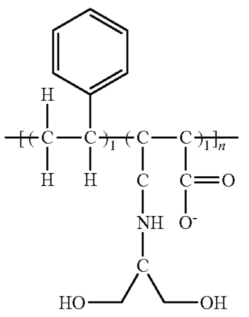

7

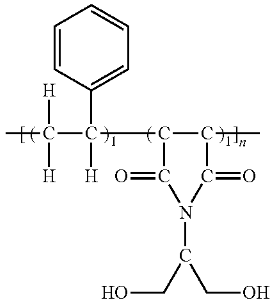

8

Poly(styrene-alt-meleamic acid-1,3-propanediol) (PDO-SMA, 7, left) and poly(styrene-alt-maleimide-1,3-propanediol) (PDO-SMAi, 8, right). Both contain fluorescent polar subunits and sulubilize membranes.

Scheme 7 Synthesis of serinol derivatives of FDM copolymers.

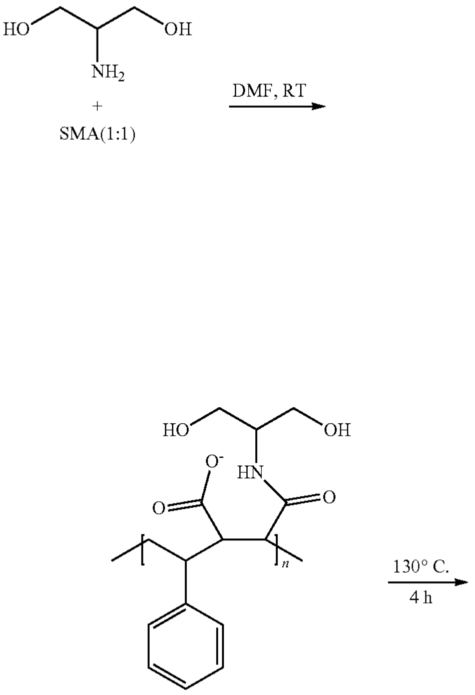

PDO-SMA (7)

-continued

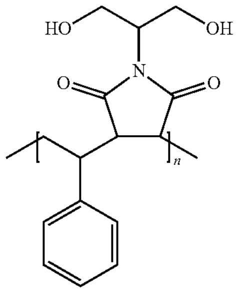

PDO-SMAi (8)

The grafting of 2-amino-1,3-propanediol (Sigma) onto SMA(1:1) (Polyscope) in DMF to form propanediol groups on compound 7 is followed by partial ring closure at high temperature in DMF to form the maleimide product 8.

Example 3

Alkyl amide containing alternating SMA copolymers 9, 10 and 11 (Scheme 8) were prepared (Scheme 9) and tested by solubilization of liposomes (FIG. 17), the bacterial protein PagP (FIGS. 18-21) and prions (FIGS. 22-26) in order to demonstrate their activities.

Scheme 8 Chemical structures of alkylamine derivatives of alternating styrene maleimide: poly(styrene-alt-maleamic acid-methylamine) (MA-SMA, 9 left), poly(styrene-alt-maleamic acid-ethylamine) (EA-SMA, 10, middle) and poly(styrene-alt-maleamic acid-propylamine) (PA-SMA, 11, right).

9

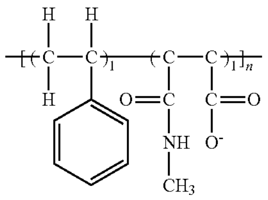

10

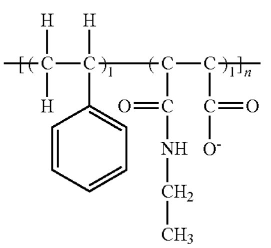

11

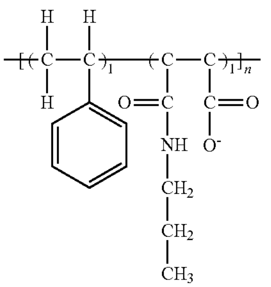

Scheme 9 Synthesis of alkyl amide derivatives copolymers.

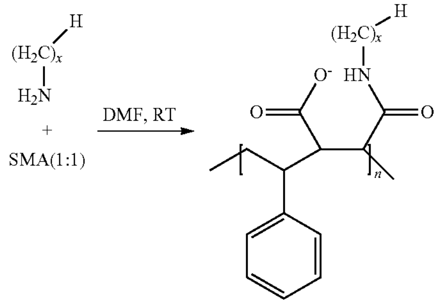

x = 1 MA-SMA [9]
x = 2 EA-SMA [10]
x = 3 PA-SMA [11]

The grafting of methylamine, ethylamine and propylamine (Sigma) onto SMA(1:1) (Polyscope) to form the corresponding alkyl amide groups on compounds 9, 10 and 11 is shown. The sytrene maleic anhydride reactant (5 gm) was dissolved in 40 mM DMF in a round bottom flask, and methylamine, ethylamine or propylamine was added to the solution while stirring at room temperature for 3-5 hr. The products were precipitated in diethyl ether, and dried. The dry powder was dissolved in NaOH and precipitated by addition of HCl until the pH <5. The pellet was collected and washed again twice. The copolymer product was collected by centrifugation and dissolved in 20 mL NAOH 0.5M and the pH was adjusted to 7-8. The products were evaluated by FT-IR and NMR.

The solubilization of prion complexes with MA-SMA (9) and related copolymers was investigated. Prion diseases are fatal and incurable neurodegenerative diseases that are driven by propagation of pathological forms of prion proteins. Although it is well-established that prions are membrane associated, the lipid binding profiles and effects on infectivity and structure are not yet well understood, particularly for the forms found in vivo. Native prion complexes have been isolated in nanodiscs for structural and functional studies that could enable development of specific diagnostics and therapeutics for the pathological lipid-bound multimeric states. The properties of brain-derived prion: lipid complexes SMALPs were compared, allowing the in vivo activities of a copolymer series to be defined.

In order to synthesize improved prion-compatible copolymers, a SMA(1:1) derivative which exhibits lower sequence heterogeneity and reduced polyvalent cation affinity. In particular methyl amides were grafted on to the maleamic groups to replace of the maleic acid groups that would otherwise bind more tightly to metal cations. Clusters of lipid-inserting styrenes can also mediate undesirable nonspecific interactions with fibrils, and hence the styrene ratio was reduced with a compensatory methyl added onto the maleimide. Crystallization and structural analysis would benefit from more regularized belts of copolymer around nanodiscs that encapsulate protein-phospholipid complexes. Incorporation of thiol groups in a SMA(2:1) copolymer may offer hydrogen bonding and crosslinking potential. Here, we investigated the strengths and weaknesses of using different formulations of SMA copolymers in vivo and in vitro as alternatives for small molecule detergents in the study of the infectious prions, with potential applicability to virtually any membrane-associated target.

Scheme 10 Chemical structures and synthesis of SMA copolymers used for prion analysis.

A

Maleic anhydride

Maleic acid

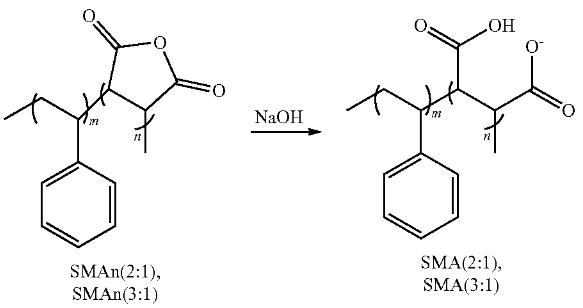

SMAn(2:1), SMAn(3:1)

SMA(2:1), SMA(3:1)

B

SMAn(2:1)

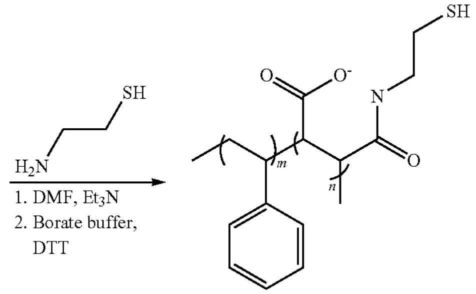

SMA-SH

C

SMAn(1:1)

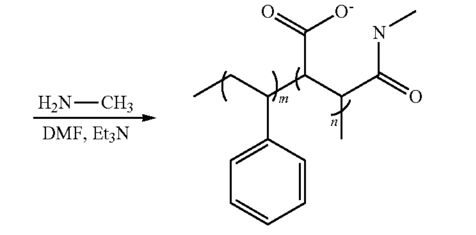

SMA(1:1)ma

The copolymers in (A) SMA(2:1), SMA(3:1) (B) SMA-SH and (C) SMA(1:1)ma have average m:n ratios of styrene to maleic acid groups of 2:1, 3:1, 2:1 and 1:1, respectively. The SMA(1:1)ma copolymer shown in this example is the same compounds as MA-SMA, as defined in Table 1.

A series of four copolymers was synthesized to contrast the effects of copolymer charge, hydrophobicity and reactivity on native prion solubilization and activity. A methylamine derivative of SMA(1:1) copolymer was synthesized as, unlike the nonalternating copolymers, it offers regular 1:1 alteration of its sidechains. The activity of this FDM copolymer was contrasted with SMA(2:1) and SMA(3:1) copolymers which contain statistically defined sequences with 2:1 and 3:1 ratios of hydrophobic to polar monomers, respectively (Scheme 10) for subsequent analysis of prion solubilization and activity. A form with free thiol groups was synthesized from SMA copolymer by grafting cysteamine to SMA(2:1) copolymer for comparative purposes.

Activity of the copolymer-based nanodiscs was tested using brain homogenates (20% w/v), which were taken from clinically ill Hyper hamsters and FVB-RML mice and prepared in DPBS+5% glycerol, mixed with 8% (w/v) SMA stock solution to a final concentration of 1% (w/v) and PronaseE (Sigma). Each mixture was then incubated at 37° C. for 30 min. when the protease was inactivated by EDTA addition. Sodium phosphotungstic acid (PTA, 200 μL of 10% w/v, pH 7.2) was added and the mixtures were incubated for one hour at 37° C. The solutions were centrifuged at 16,500×g, and the pellets were re-suspended in DPBS and 5% (v/v) glycerol and stored at −20° C. for analysis by gel electrophoresis (FIG. 22) and later assays.

For bioassays the brain tissue of each infected animal was removed post-mortem, and a brain homogenate (10% w/v) was prepared in DPBS with 5% glycerol. To assess prion protease sensitivity, 160 μL of 10% brain homogenate was incubated with varying concentrations of PK (0, 5, 50, 200 μg/mL) at 37 ° C. for 60 minutes with constant agitation. PK was inactivated by adding 0.5 mM phenylmethylsulfonyl fluoride (PMSF) and samples were mixed with 2× sample buffer, heated to 100° C., run on SDS-PAGE and immunoblotted (FIG. 23). Silver staining methods included fixing and washing gels in ethanol to remove excess SDS. After treatment with Farmer's solution, gels were incubated with $AgNiO_3$ for 20 minutes and developed in formaldehyde sodium carbonate solution.

Sucrose gradients of prion nanodiscs in DPBS buffer were prepared in 3.5 mL Beckman ultracentrifuge tubes in order to resolve prion multimers. Three independent sets of SMA-purified samples were overlaid on top of each gradient and spun at 37,000 rpm (130,000×g) in a SWTi55 swinging-bucket rotor (Beckman Coulter) for at least 17 hours at 4° C. Fractions (200 μL) were collected from the top to the bottom of tubes and 40 μL aliquots were mixed with an equal volume of sample buffer (Bio-Rad) and heated for 10 min at 100° C. as per western blotting and SDS-PAGE gels (FIG. 24).

The SMA isolates of prions contain mainly two protofilaments that have diameters of approximately 20 nm in negative stain electron microscopy images (FIG. 25), while entangled long rods were seen in sarkosyl-treated samples. Moreover, lipid vesicles are particularly enriched in SMA (1:1)ma isolates, which show protofilament: vesicle complexes. Transmission electron microscopy (EM) analysis of prions isolated with FDM copolymers was performed on carbon coated copper grids with a 400 nm-mesh were charged using a EMS 100×glow discharge unit (Electron Microscopy Sciences). filtered 2% uranyl acetate. Excess dye was removed using a filter paper and air-dried for at least 5 minutes Microliter amounts of each SMA-purified prion sample were loaded on the grids and let to adsorb for 30 seconds. The grids were washed three times (3×50 μL) with ammonium acetate (pH 6.8) and stained with before TEM imaging. Micrographs were collected using a Tecnai G20 transmission electron microscope equipped with an Eagle 4 k×4 k CCD camera (FEI) with an acceleration voltage of 200 kV.

The lipids associated with $PrP^{Sc}$ assemblies extracted from brains of infected and healthy hamsters and mice were identified and quantified, allowing relative levels of eleven types of lipid to be compared (FIG. 26, Table 3). These findings indicate that SMA(1:1)-methylamine has a higher capacity for isolation of various types of prion-associated lipids.

TABLE 3

Summary of calculated amount of lipids in Hyper hamster and FVB-RML mouse

| | Hyper-hamster | | | | |
|---|---|---|---|---|---|
| Lipid type | SMA(1:1)ma | SMA(2:1) | SMA(3:1) | SMA-SH | Sarkosyl |
| CE | 4.81 | 4.96 | 3.99 | 5.09 | 27.41 |
| TG | 17.18 | 11.13 | 9.31 | 0 | 11.09 |
| FC | 138.40 | 111.81 | 103.15 | 133.87 | 24.35 |

TABLE 3-continued

Summary of calculated amount of lipids in Hyper hamster and FVB-RML mouse

| | | | | | |
|---|---|---|---|---|---|
| DG | 11.22 | 0 | 0 | 0 | 0 |
| FA | 11.50 | 0 | 0 | 0 | 0 |
| PE | 348.21 | 128.07 | 49.66 | 139.50 | 8.57 |
| PI | 58.64 | 19.78 | 16.60 | 22.00 | 0 |
| PS | 108.67 | 47.86 | 27.39 | 67.89 | 2.23 |
| PC | 325.24 | 152.82 | 114.53 | 176.36 | 21.46 |
| SM | 14.59 | 13.35 | 15.13 | 14.81 | 3.12 |

| | FVB-RML | | | | |
|---|---|---|---|---|---|
| Lipid type | SMA(1:1)ma | SMA(2:1) | SMA(3:1) | SMA-SH | Sarkosyl |
| CE | 0 | 2.77 | 2.29 | 61.18 | 3.54 |
| TG | 0 | 0 | 0 | 0 | 4.29 |
| FC | 288.78 | 127.65 | 81.19 | 208.93 | 31.17 |
| DG | 17.92 | 0 | 0 | 0 | 0 |
| FA | 13.31 | 5.43 | 0 | 0 | 0 |
| PE | 437.60 | 148.81 | 56.82 | 215.55 | 21.83 |
| PI | 57.36 | 22.19 | 5.25 | 12.40 | 1.92 |
| PS | 166.50 | 66.76 | 27.70 | 90.77 | 8.05 |
| PC | 430.09 | 133.19 | 78.17 | 190.89 | 16.80 |
| SM | 28.07 | 8.13 | 6.18 | 13.40 | 1.58 |

Lipid species include cholesterol esters (CE), triglycerides (TG), free cholesterol (FC), dipalmitoyl phosphatidylglycerol (dii6PG), phosphatidylethanolamine (PE), phosphatidylinositol (PI), phosphatidylserine (PS), phosphatidylcholine (PC) and sphingomyelin (SM). This shows the diversity of biological lipids that can be solubilized by various SMA copolymers, with SMA(1:1)ma (identical to MA-SMA, 9) providing the largest yield of prion protein-bound lipid.

The symptoms of mice and hamsters inoculated with PrPSc extracted from brain with different SMA copolymers or sarkosyl were compared to those inoculated with brain homogenate from infected animals (Table 4). Prion disease presents as ataxia, scruffy coats, loss of gait, weight loss and head bobbing at the time of euthanasia. The average incubation times from SMALP-PrPSc particle inoculation until terminal disease was consistently around 85-90 days in Hyper hamsters, with SMA(1:1)ma, SMA(2:1) and SMA-SH-purified PrPSc showing similar periods (Table 4a) as sarkosyl purified PrPSc. In contrast, inoculation with SMA (3:1)-purified PrPSc yielded the longest incubation times. As expected, inoculation with 1% prion 263K brain homogenate from infected animals was most efficient. Given the 153 days for average incubation time of RML prions in FVB mice, mice incubated with SMA-SH and SMA(3:1) purified PrPSc showed the shortest and longest incubation times, i.e. 163 and 187 days, respectively (Table 4b). Despite the variability of incubation period for different SMA-purified samples, animals in SMA(3:1), SMA(2:1), SMA(1:1)-methylamine and SMA-SH groups show the same clinical symptoms, suggesting that the isolation method did not alter prion strain characteristics. Brain homogenates of animals infected with isolated SMALP-PrPSc particles were used for a second passage into healthy hamsters (Table 4c). The incubation periods display, to a great extent, the same trend in both incubation period and symptoms at terminal stage as first passage, with SMA(3:1) having the longest incubation periods. Protease digestion of postmortem brain tissues reveals that all animals, regardless of the incubation period and clinical symptoms, display the characteristic profile of PK-resistant PrP, again supporting our conclusion that each purification protocol did not alter the strain characteristics.

TABLE 4

A summary of bioinfectivity of SMA-treated PrPSc samples in Hyper hamster (a) and RML mice (b). In both Hyper-infected hamsters and RML-infected mice, 10% brain homogenates and Sarkosyl-purified PrPSc were used as controls, (c) Second passage of brain homogenates of animals infected with SMA-isolated Hyper PrPSc into healthy Syrian hamsters.

| Sample | Incubation period (days) ± SEM ($N/N_0$) |
|---|---|
| a) | |
| 1% 263K brain homogenate (control) | 71 ± 0.5 (4/4) |
| treated with 1% Sarkosyl-PrP$^{sc}$ (control) | 76 ± 5 (12/12) |
| treated with 1% SMA(2:1)-PrP$^{sc}$ | 87 ± 3 (12/12) |
| treated with 1% SMA-SH-PrP$^{sc}$ | 88 ± 4 (12/12)* |
| treated with 1% SMA(3:1)-PrP$^{sc}$ | 94 ± 3 (12/12)* |
| treated with 1% SMA(1:1)ma-PrP$^{sc}$ | 84 ± 8 (12/12) |
| b) | |
| treated with 1% Sarkosyl-PrP$^{sc}$ (control) | 158 ± 19 (19/19) |
| treated with 1% SMA(2:1)-PrP$^{sc}$ | 172 ± 21 (15/15) |
| treated with 1% SMA-SH-PrP$^{sc}$ | 163 ± 15 (14/14) |
| treated with 1% SMA(3:1)-PrP$^{sc}$ | 187 ± 33.5 (17/17)* |
| treated with 1% SMA(1:1)ma-PrP$^{sc}$ | 174 ± 27 (9/9) |
| c) | |
| 1% 263K brain homogenate (control) | 71 ± 0.5 (4/4) |
| treated with 1% SMA(2:1)-PrP$^{sc}$ | 74 ± 3 (6/6) |
| treated with 1% SMA-SH-PrP$^{sc}$ | 97 ± 2 (6/6)* |
| treated with 1% SMA(3:1)-PrP$^{sc}$ | 115 ± 0.5 (6/6) |
| treated with 1% SMA(1:1)ma-PrP$^{sc}$ | 87 ± 3 (10/10)* |

*Significant difference (p value < 0.001) between the incubation periods of SMA treated samples and sarkosyl-purified PrPSc.

Note:

SMA(1:1)ma is identical to MA-SMA, 9

Example 4

Amino acid residue containing copolymers 12, 13 and 14 (Schemes 11,12) were prepared (Scheme 13) and tested by using liposomes (FIG. 27) and using the bacterial protein PagP (FIGS. 28 & 29) in order to demonstrate their solubilization activities.

Scheme 11 Chemical structures of mono-amino acid derivatives of alternating styrene maleamic acid

12

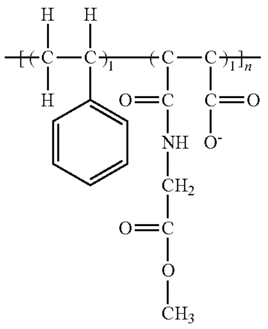

-continued

13

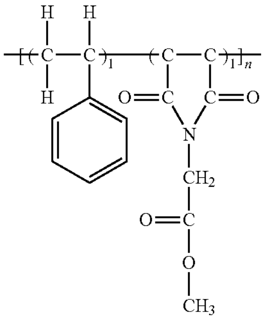

Poly(styrene-alt-maleamic acid-glycine-methyl-ester) (Gly-SMA, 12) and poly(styrene-alt-maleamic acid-glycine-methyl-ester) (Gly-SMAi, 13) are shown.

Scheme 12 Chemical structure of di-amino acid derivatives of alternating styrene maleamic acid.

14

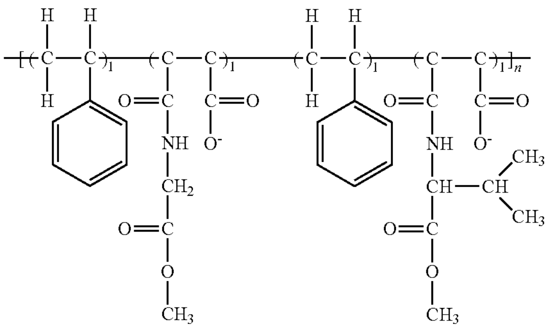

Poly(styrene-alt-maleamic acid-glycine, valine-methyl-ester) (GV-SMA, 14) is shown.

Scheme 13 Synthesis of glycine and valine-containing FDM copolymers.

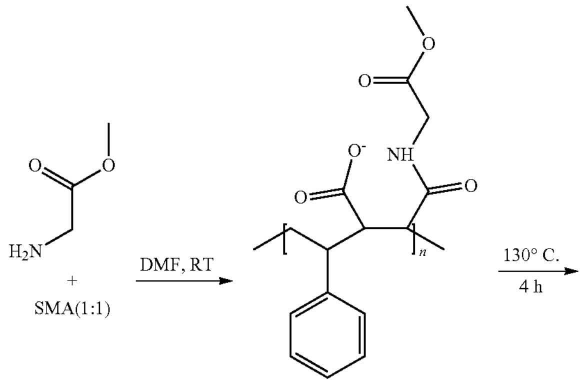

Gly-SMA (12)

-continued

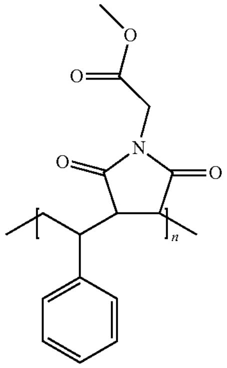

Gly-SMAi (13)

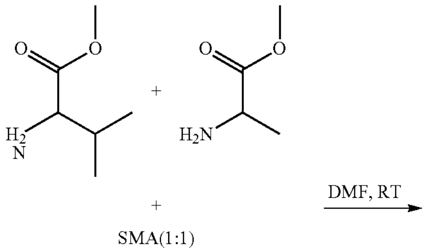

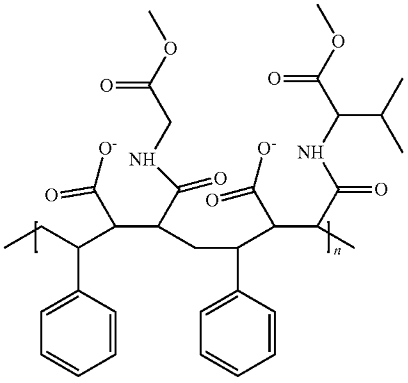

GV-SMA (14)

The grafting of glycine methyl ester chloride (Sigma) and a mixture of glycine methyl ester chloride and L-valine methyl ester chloride (Sigma) onto SMA(1:1) (Sartomer) in DMF yields Gly-SMA (12), Gly-SMA (13) and GV-SMA (14).

Example 5

The utility of CD-SMA type copolymers incorporating a stilbene group with methyl-substituted phenyl groups rather than a styrene with a single phenyl group as the hydrophobic subunit was demonstrated using a series of stilbene maleimides, as provided by Richard Turner's group at Virgina Tech (USA). The structures of the activated, water soluble maleic acid derivatives 15 and 17 are shown in Schemes 14 and 16, respectively, and the reactions used for their activation are shown in Schemes 15 and 17, respectively.

Scheme 14 Chemical structures fo ortho-methyl derivatives of stilbene maleimide.

15

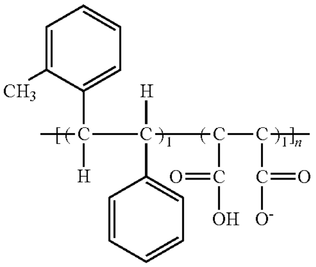

16

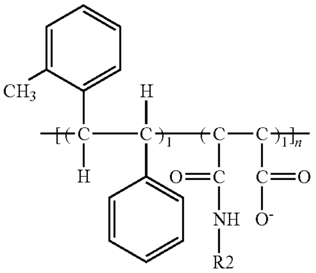

Poly(ortho-methyl-stilbene-maleic acid) (OM-STM, 15, left) and poly(ortho-methyl-stilbene-maleamic acid) (OM-STMA, 16, right) are shown. The R2 group may comprise any of the substituents described in the present application.

Scheme 15 Synthesis of ortho-methyl-phenyl derivatives of FDM copolymers.

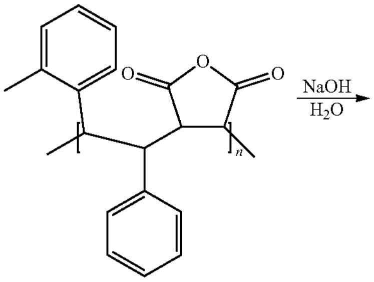

OM-STMAH

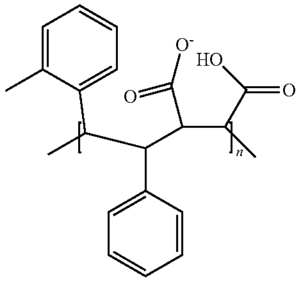

OM-STM (15)

-continued

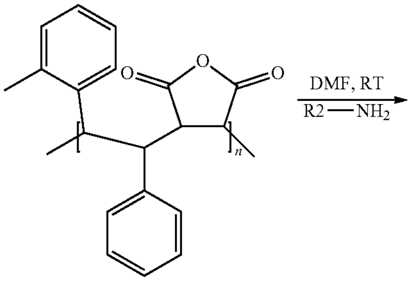

OM-STMAH

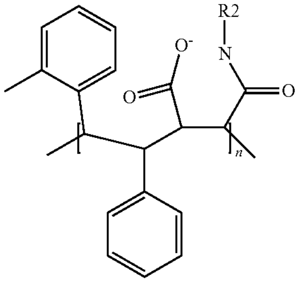

OM-STMA (16)

The activation of stilbene maleic anhydride (STMAH) by addition of NaOH in water produced stilbene maleic acid product 15. Addition of R2 groups in DMF yield stilbene maleamic acid product 16. Prior to lyophilization, each sample was adjusted to pH 8. The source stilbene maleimide was provided by Richard Turner (Virginia Tech), and was synthesized as published previously. [21] The R2 group may be any of the substituents described in the present application.

Scheme 16 Chemical structures fo methylated derivatives of stilbene maleimide.

17

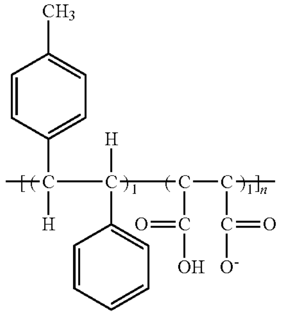

18

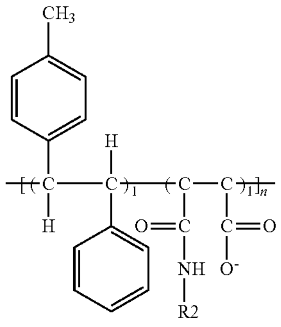

Poly(para-methyl-stilbene-maleic acid) (PM-STM, 17, left) and poly(para-methyl-stilbene-maleamic acid) (PM-STMA, 18, right) are shown. The R2 group may be any of the substituents described in the present application.

Scheme 17 Synthesis of para-methyl-phenyl derivatives of FDM copolymers.

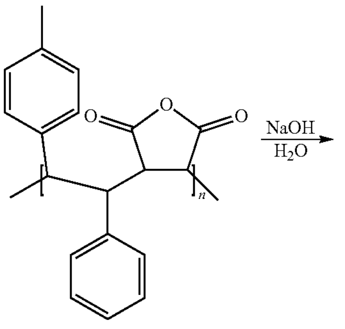

PM-STMAH

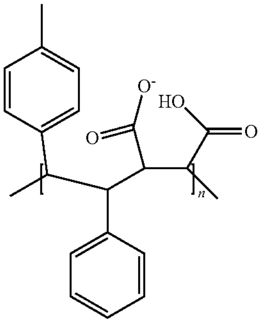

PM-STM (17)

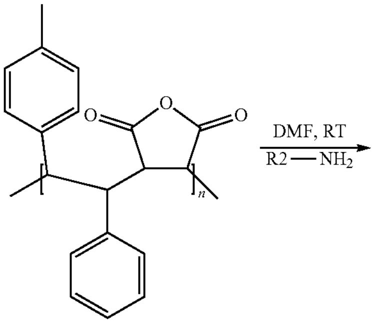

PM-STMAH

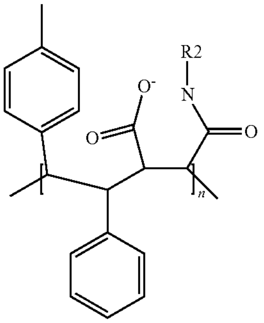

PM-STMA (18)

The activation of para-methyl stilbene maleic anhydride (PM-STMAH) by addition of NaOH in water produced stilbene maleic acid product 17. Prior to lyophilization, each sample was adjusted to pH 8. The complete conversion of the anhydride into diacid was confirmed by FT-IR. The source copolymer was provided by Richard Turner and was synthesized as described.
[21] Addition of R2 groups performed in DMF yields stilbene maleamic acid product 18. The R2 group may comprise any of the substituents described in the present application.

The data showing solubilization and analysis of membranes is shown in FIGS. 30, 32-35. The copolymers 15 and 17 were found to be soluble from pH 4 to 10. (FIG. 30), providing a broad utility across the biological range of pH values of interest. Given the sensitivity of hydrolyzed SMA to divalent cations because of the maleic acid subunits, we expected both 15 and 17, the NMR spectra of which are shown in FIG. 31, to solubilize membranes (FIG. 32) and show similar sensitivities to levels of $Ca^{2+}$ that exceed 5 mM, as was confirmed (FIG. 33). We investigated 15 and 17 for their abilities to solubilize *E. col* outer membranes, which are tightly packed with proteins and glycolipids. The protein, PagP β-barrel, was expressed into the outer membrane and 15 and 17 were added individually to raw outer membrane samples at a copolymer concentration of 0.5% w/v (FIG. 34). The PagP monomers and dimers are solubilized directly from the outer membrane into the supernatant by treatment with 15 and 17 (FIG. 35), purified by SEC (FIG. 36) and visualized by EM (FIG. 37).

Example 6

The antibiotic daptomycin is a membrane-binding lipopeptide for which no membrane-bound structure is available due in part due to the technical difficulties presented by detergent-based preparation. Daptomycin is used to treat infections caused by Gram-positive pathogens such as methicillin-resistant *Staphylococcus aureus* (MRSA). This lipopeptide is produced by the soil bacterium *Streptomyces roseosporus* and is composed of 13 amino acid residues which form a macro-cycle as well as a decanoyl fatty acid tail. Daptomycin's bacterial lethality is due to binding to bacterial membranes. This mechanism occurs via a calcium-mediated process that involves phosphatidylglycerol lipid and dap multimerization into octamers or pairs of tetramers that yield cation-selective pores and membrane-depolarization. Conventional SMA copolymers such as SMA2000 bind calcium ions via pairs of carboxylic acid moieties, and then precipitate, complicating analysis of dap in SMALPs. MA-SMA (9) was used due to the calcium tolerance and gentle solubilization of complex multimers by this copolymer. The octameric and tetrameric states of membrane-associated daptomycin were measured by fluorescence resonance energy transfer (FRET) experiments in collaboration with Michael Palmer at the University of Waterloo. The daptomycin molecules were labelled with 7-nitro2,1,3-benzoxadiazol (NBD) and used as the FRET acceptor in fluorescence experiments, while native daptomycin was used as the FRET donor. Nanodiscs were made by mixing MA-SMA to vesicles composed of a 1:1 ratio of 1,2-dimyristoyl-sn-glycero-3-phosphocholine (DMPC; from Avanti Polar Lipids), 1,2 dimyristoyl sn glycero 3 phospho(1' rac glycerol) (sodium salt; DMPG; from Larodan, Slona, Sweden). The NBD-daptomycin and native daptomycin were added by either premixing or sequentially adding these to the nanodiscs. Emission spectra were then acquired on a PTI QuantaMaster 4 instrument at 37 ° C. The stoichiometries of daptomycin in MA-SMA-based nanodiscs were determined from the sensitivity of the FRET signal to the timecourse of oligomer assembly. In the case of nanodiscs that were formed with 3 equivalents of MA-SMA the estimated subunit number was 7.4±0.33, which is similar to the expected octameric state (FIG. 38). Using nanodiscs formed with 9 equivalents of MA-SMA yielded an apparent tetramer based on an estimated subunit number of 4.4±0.11. The data shown is the average of 3 independent experiments. Changes in $^1H$ NMR chemical shifts of aliphatic groups of daptomycin upon addition of MA-SMA nanodiscs support the presence of a direct interaction (FIG. 39). The calcium-dependent nature of the membrane interaction was investigated by fluorescence measurements. Daptomycin contains an intrinsically fluorescent kynurenine residue which is sensitive to membrane interactions. Hence its fluorescence emission signal was used to detect the calcium-dependent interactions of daptomycin with MA-SMA copolymer-stabilized nanodiscs revealing that increasing the calcium concentration from 0.1 to 10 mM progressively stabilized the membrane interaction (FIG. 40), consistent with its role in stabilizing daptomycin-phosphatidylglycerol interactions.

Example 7

The structures of additional FDM-type copolymers are depicted in Scheme 18 to illustrate a variety of R2 sidechains and methyl, halogen (such as fluorine, chlorine, and bromine), and hydroxy groups that can be present as well as the placement of R1 and R2 groups on a FDM-type copolymer comprising of alternating maleamic acid derivatives as the polar "b" subunit and diisobutyl or diisopropyl groups in the hydrophobic "a" subunit.

Scheme 18 Chemical structures of FDM derivatives poly(styrene-alt-maleamic acid-propyl-trimethylammonium) (19), poly(styrene-alt-maleimide-propyl-trimethylammonium) (20), poly(styrene-alt-maleamic acid-ethyl-dimethylamine) (21), poly(styrene-alt-maleimide-ethyl-dimethylamine) (22), poly(styrene-alt-maleamic acid-propanolamine) (23), poly(styrene-alt-maleimide-propanolamine) (24), poly(diisobutylene-alt-maleamic acid) (25), poly(diisobutylene-alt-maleimide) (26), poly(diisopropylene-alt-maleamic acid) (27), poly(diisopropylene-alt-maleimide) (28), poly(methyl-styrene-alt-maleamic acid) (29), poly(methyl-styrene-alt-maleamide) (30), poly(hydroxystyrene-maleamic acid) (31), poly(bromostyrene-maleamic acid) (32), poly(styrene-alt-maleamic acid-trifluoroethylamine) (33), poly(styrene-alt-maleamic acid-trifluoropropylamine) (34), poly(styrene-alt-maleamic acid-bromoethylamine) (35) or poly(styrene-alt-maleamic acid-bromopropylamine) (36). The synthesis of these copolymers involves adding a compound with the general structure NH2—R2 to the maleic anhydride containing copolymer to perform the hydrolysis reaction.

19

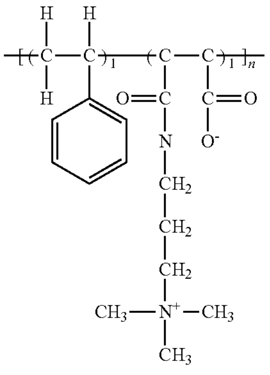

20

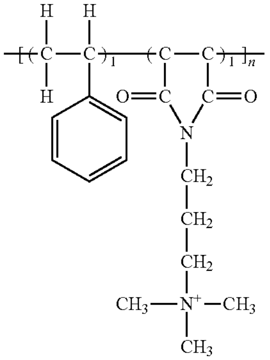

-continued

21

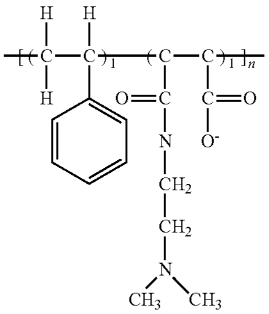

22

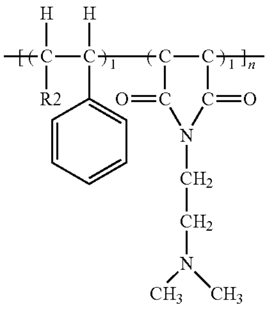

23

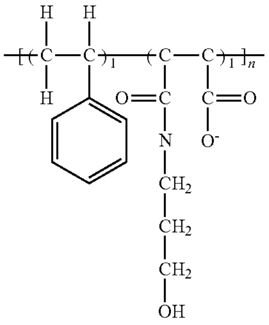

24

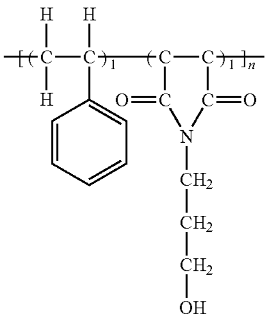

25

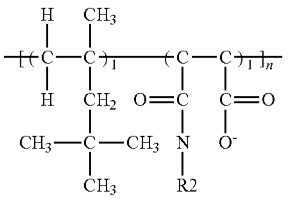

-continued

26

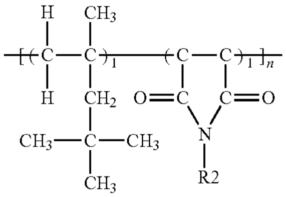

27

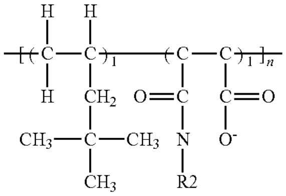

28

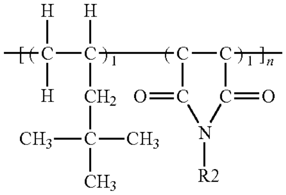

29

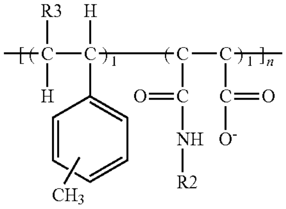

30

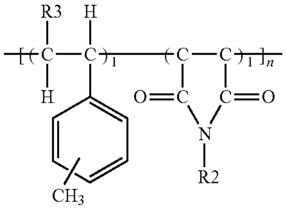

31

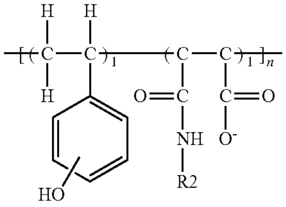

32

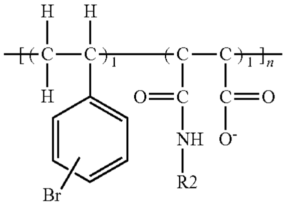

-continued

33

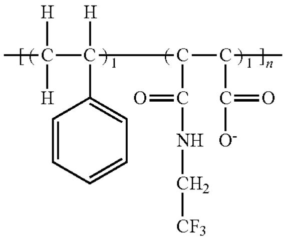

34

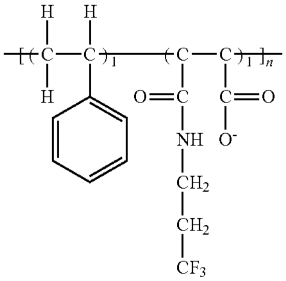

35

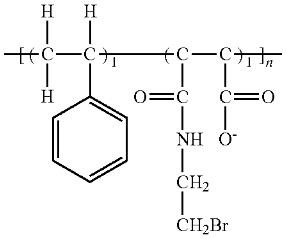

36

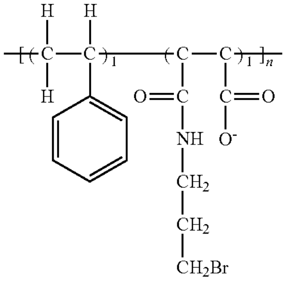

Statements of the Invention.

Based on the disclosure above, various embodiments can be briefly summarized by the following Statements of the Invention. Herein we report the discovery of functional derivatives of maleimide and styrene or stilbene subunit-containing (FDM) copolymers of the formula shown in Scheme 1. The number of monomer units, represented by the value "n" in any one of the formulas described herein, can be 5-10, 10-20, 20-30, 30-40, 40-50, 50-75, 75-100, 100-125, 125-150, 150-200, or 200-250. These can be added to biological material to form 10-30 nanometer diameter discs which are held by an annulus of the copolymer, as shown in FIG. 1 with a cross section as illustrated in FIG. 2. The average width of the two concentric circles forming the annulus (i.e., the region between the inner and outer boundaries of the annulus) is about 0.2 nm to about 15 nm, about 1 nm to about 10 nm, about 2 nm to about 8 nm, or about 1 nm to about 5 nm. The disc-shaped particles are soluble in water and allow stable detection of the copolymer across a broad range of pH values and salt concentrations. The biological material can include brain homogenate, brain matter, biological organ, biological tissue, animal matter, plant matter, eukaryotic cells, prokaryotic cells, or complex between lipids and membrane protein such as a membrane enzyme, membrane receptor, membrane ion channel, transmembrane protein, membrane antigen, membrane-bound antibody, an integral monotopic membrane protein, a peripheral membrane protein, an amphitropic protein or a lipid-modified protein. For solubilization the FDM copolymer is added at a concentration of between 0.1 to 10% w/v or preferably between 0.5 to 3% w/v in the presence of the aqueous solution containing the biological material. The biological material can be bound to or used to screen for a ligand such as a lipid, a biologically active agent, a drug, a co-factor, a diagnostic probe molecule, an active ingredient of a plant protective product, an active ingredient of a cosmetic product, a contrast agent, a dietary supplement, a nutritional supplement, a molecular label and an indicator. The process of purifying the nanodisc solubilized by the FDM copolymer could include the use of affinity resins, magnetic beads, chromatography columns, centrifugation, dialysis, concentrators in order to at least partially remove unbound or unincorporated lipids polypeptides, proteins, cofactors or metabolites and obtain higher purity of a specific membrane protein. A liberation process is envisaged wherein the FDM copolymer is removed from any of the nanoparticles by treatment with another interacting copolymer or molecule containing opposite charge or complementary hydrophobic interfaces, with a chromatography matrix such as NTA, pH change or addition of polycations, in order to at least partially remove the FDM copolymer from the nanoparticle and allow the contained biological material such as protein:lipid complexes to be moved into another media such as a liposome or into the gas phase for analysis by methods such as mass spectrometry. It is also envisaged that the FDM copolymers and resultant nanodiscs could be useful in manufacturing a hydrophobic agent such as a delivery nanoparticle, drug molecule, drug formulation, drug development agent, drug screening candidate, membrane protein ligand or vaccine composition. It is further envisaged that the FDM copolymers and resultant nanodiscs could be especially useful for structural characterization or spectroscopic detection of membrane proteins using fluorescence, X-ray diffraction, electron microscopy or nuclear magnetic resonance signals. The FDM copolymers are also designed to be useful for concentrating and releasing a hydrophobic molecule, lipid or metabolite lipid onto a surface and for screening and detection of molecular interactions of ligands of membrane proteins using methods such as but not limited to isothermal titration bio-layer interferometry, isothermal titration calorimetry, microscale thermophoresis, surface plasmon resonance detection.

CITATIONS

[1] M. Overduin and M. Esmaili, "Memtein: The fundamental unit of membrane-protein structure and function," *Chemistry and Physics of Lipids.* 2019.

[2] I. G. Denisov and S. G. Sligar, "Nanodiscs in Membrane Biochemistry and Biophysics," *Chemical* Reviews. 2017.

[3] C. Le Bon, A. Marconnet, S. Masscheleyn, J. L. Popot, and M. Zoonens, "Folding and stabilizing membrane proteins in amphipol A8-35," *Methods.* 2018.

[4] T. J. Knowles, R. Finka, C. Smith, Y.-P. Lin, T. Dafforn, and M. Overduin, "Membrane proteins solubilized intact in lipid containing nanoparticles bounded by styrene maleic acid copolymer," *J. Am. Chem. Soc., vol.* 131, no. 22, pp. 7484-5,2009.

[5] T. Ravula, S. K. Ramadugu, G. Di Mauro, and A. Ramamoorthy, "Bioinspired, Size-Tunable Self-Assembly of Polymer—Lipid Bilayer Nanodiscs," *Angew Chem Int Ed Engl,* vol. 56, no. 38, pp. 11466-11470, 2017.

[6] V. S. K. Ramadugu, G. M. Di Mauro, T. Ravula, and A. Ramamoorthy, "Polymer nanodiscs and macro-nanodiscs of a varying lipid composition," *Chem. Commun.,* vol. 53, no. 78, pp. 10824-10826, 2017.

[7] T. Ravula, N. Z. Hardin, S. K. Ramadugu, and A. Ramamoorthy, "PH Tunable and Divalent Metal Ion Tolerant Polymer Lipid Nanodiscs," *Langmuir*, vol. 33, no. 40, pp. 10655-10662,2017.

[8] T. Ravula, N. Z. Hardin, S. K. Ramadugu, S. J. Cox, and A. Ramamoorthy, "Formation of pH-Resistant Monodispersed Polymer—Lipid Nanodiscs," *Angew. Chemie-Int. Ed.*, vol. 57, no. 5, pp. 1342-1345,2018.

[9] T. Ravula, N. Z. Hardin, J. Bai, S. C. Im, L. Waskell, and A. Ramamoorthy, "Effect of polymer charge on functional reconstitution of membrane proteins in polymer nanodiscs," *Chem. Commun.,* 2018.

[10] S. Hall et al., "An acid-compatible co-polymer for the solubilization of membranes and proteins into lipid bilayer-containing nanoparticles.," *Nanoscale*, vol. 10, no. 22, pp. 10609-10619,2018.

[11] A. Grethen, A. 0. Oluwole, B. Danielczak, C. Vargas, and S. Keller, "Thermodynamics of nanodisc formation mediated by styrene/maleic acid (2:1) copolymer," *Sci. Rep.,* 2017.

[12] O. Korotych, J. Mondal, K. M. Gatts-Asfura, J. Hendricks, and B. D. Bruce, "Evaluation of commercially available styrene-co-maleic acid polymers for the extraction of membrane proteins from spinach chloroplast thylakoids," *Eur Polym. J.*, vol. in press, 2019.

[13] K. A. Morrison et al., "Membrane protein extraction and purification using styrene-maleic acid (SMA) copolymer: effect of variations in polymer structure," *Biochem. J.*, vol. 473, no. 23, pp. 4349-4360, 2016.

[14] S. M. Henry, M. E. H. El-Sayed, C. M. Pirie, A. S. Hoffman, and P. S. Stayton, "pH-responsive poly(styrene-alt-maleic anhydride) alkylamide copolymers for intracellular drug delivery," *Biomacromolecules,* 2006.

[15] H. Maeda, "SMANCS and polymer-conjugated macromolecular drugs: Advantages in cancer chemotherapy," *Adv. Drug Deliv. Rev.,* 2001.

[16] M. C. Fiori, Y. Jiang, G. A. Altenberg, and H. Liang, "Polymer-encased nanodiscs with improved buffer compatibility," *Sci. Rep.*, vol. 7, no. 1, p. 7432,2017.

[17] A. O. Oluwole, B. Danielczak, A. Meister, J. O. Babalola, C. Vargas, and S. Keller, "Solubilization of Membrane Proteins into Functional Lipid-Bilayer Nanodiscs Using a Diisobutylene/Maleic Acid Copolymer," *Angew. Chemie-Int. Ed.*, vol. 56, no. 7, pp. 1919-1924, 2017.

[18] A. O. Oluwole et al., "Formation of Lipid-Bilayer Nanodiscs by Diisobutylene/Maleic Acid (DIBMA) Copolymer," *Langmuir, vol.* 33, no. 50, pp. 14378-14388, 2017.

[19] K. Yasuhara et al., "Spontaneous Lipid Nanodisc Fomation by Amphiphilic Polymethacrylate Copolymers," *J. Am. Chem. Soc.*, vol. 139, no. 51, pp. 18657-18663, 2017.

[20] N. Z. Hardin, T. Ravula, G. Di Mauro, and A. Ramamoorthy, "Hydrophobic Functionalization of Polyacrylic Acid as a Versatile Platform for the Development of Polymer Lipid Nanodisks," *Small,* 2019.

[21] Y. Li and S. R. Turner Free radical copolymerization of methyl substituted stilbenes with maleic anhydride, Eur. Polymer J., 46(4), 821-828

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An amphiphilic copolymer comprising Formula $I^A$, Formula $I^B$, or a combination thereof, wherein:

i) Formula $I^A$ is represented as, ($I^A$)

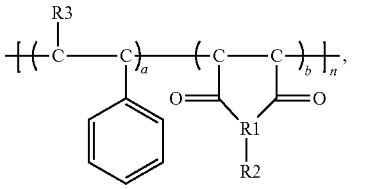

wherein

R1 is N;

R2 is —($C_1$-$C_3$)alkyl, (alkanol, or alkylamine oxide, wherein —($C_1$-$C_3$)alkyl is substituted optionally with halo; or R1 and R2 taken together form a histamine, amino alkanediol, or alkyl ester of an amino acid residue; and R3 is a hydrogen, unsubstituted phenyl, or phenyl substituted by one or more non-polar substituents;

ii) Formula $I^B$ is represented as, ($I^B$)

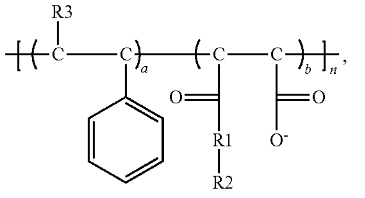

wherein

R1 is O or NH;

when R1 is O, R2 is H;

when R1 is NH:

R2 is —($C_1$-$C_{12}$)alkyl, alkanol, or alkylamine oxide, wherein —($C_1$-$C_{12}$)alkyl is substituted optionally with halo; or R1 and R2 taken together form a histamine, amino alkanediol, or alkyl ester of an amino acid residue; and R3 is a hydrogen, unsubstituted phenyl, or phenyl substituted by one or more non-polar substituents;

wherein the oxygen anion of Formula $I^B$ has a positively charged monovalent counter ion; and iii) independently for Formula $I^A$ and $I^B$, n is about 9 to about 90, and the monomer moieties labeled a and b are in an alternating, substantially alternating, largely alternating, or semialternating copolymer arrangement in the length of the copolymer backbone;

wherein a=b=1 for the alternating copolymer arrangement; $1<a\leq 1.2$ and b=1 for the substantially alternating copolymer arrangement; $1.2<a\leq 1.4$ and b=1 for the largely alternating copolymer arrangement; or $1.7\leq a\leq 2.3$ and b=1 for the semialternating copolymer arrangement; and provided that for Formula $I^B$, when R3 is a hydrogen, R1 is not O and R2 is not alkylamine oxide, ($C_1$-$C_3$)alkyl, or alkanol.

2. The copolymer of claim 1 wherein the copolymer is represented by Formula $I^A$.

3. The copolymer of claim 1 wherein the copolymer is represented by Formula $I^B$; optionally, R3 is H when R1 is NH; or R3 is an unsubstituted phenyl, or phenyl substituted by one or more non-polar substituents when R1 is —NH.

4. The copolymer of claim 1 wherein R1 is —N— and R2 is —($C_2$-$C_3$)alkyl —$N(O)(CH_3)_2$, —($C_1$-$C_3$)alkyl, —($C_1$-$C_3$) alkyl-$(halo)_{1-3}$, or —$(CH_2)_3$—OH.

5. The copolymer of claim 1 wherein the monomer moiety labeled b is a hydrophilic subunit and the monomer moiety labeled a is a hydrophobic subunit, and wherein a and b are present in a substantially equimolar ratio wherein a and b are approximately both 1 and a and b are in a substantially alternating configuration in the linear sequence of the copolymer.

6. The copolymer of claim 1 wherein the copolymer is cyclized by a crosslink between the two termini of the copolymer chain.

7. A disc-shaped nanoparticle comprising an amphiphilic copolymer and biological material;

wherein one or more amphiphilic copolymers form a nanodisc having a hydrophilic outer surface, an annulus, and a hydrophobic inner core;

the biological material is held in the annulus of the nanodisc;

the biological material comprising complexes of hydrophobic molecules, lipids, proteins, or a combination thereof, derived from bacterial, mammalian, animal, fungal or plant cells or tissues; and the amphiphilic copolymer comprises Formula $I^A$, Formula $I^B$, or a combination thereof, wherein:

i) Formula $I^A$ is represented as, ($I^A$)

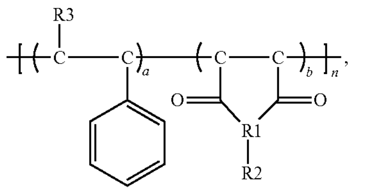

wherein

R1 is N;

R2 is —$(C_1-C_{12})$alkyl, alkanol, alkylamine, alkylamine oxide, or quaternary amine, wherein —$(C_1-C_{12})$alkyl is substituted optionally with halo; or R1 and R2 taken together form a histamine, amino alkanediol, or alkyl ester of an amino acid residue; and R3 is a hydrogen, unsubstituted phenyl, or phenyl substituted by one or more non-polar substituents;

provided that when R2 is alkanol or quaternary amine, R3 is unsubstituted phenyl, or phenyl substituted by one or more non-polar substituents;

ii) Formula $I^B$ is represented as, ($I^B$)

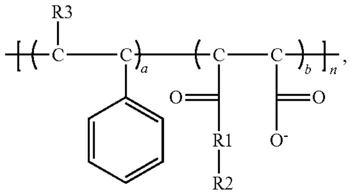

wherein

R1 is O or NH;

when R1 is O, R2 is H;

when R1 is NH:

R2 is —$(C_1-C_{12})$alkyl, alkanol, alkylamine, alkylamine oxide, quaternary amine, wherein —$(C_1-C_{12})$alkyl is substituted optionally with halo; or R1 and R2 taken together form a histamine, amino alkanediol, or alkyl ester of an amino acid residue; and R3 is a hydrogen, unsubstituted phenyl, or phenyl substituted by one or more non-polar substituents;

provided that when R1 is O and R2 is hydrogen, R3 is unsubstituted phenyl, or phenyl substituted by one or more non-polar substituents;

wherein the oxygen anion of Formula $I^B$ has a positively charged monovalent counter ion; and iii) independently for Formula $I^A$ and $I^B$, n is about 7 to about 200, and the monomer moieties labeled a and b are in an alternating, substantially alternating, largely alternating, or semialternating copolymer arrangement in the length of the copolymer backbone;

wherein a=b=1 for the alternating copolymer arrangement; $1<a\leq 1.2$ and b =1 for the substantially alternating copolymer arrangement; $1.2<a\leq 1.4$ and b=1 for the largely alternating copolymer arrangement; or $1.7\leq a\leq 2.3$ and b=1 for the semialternating copolymer arrangement.

8. The disc-shaped nanoparticle of claim 7 wherein R1 and R2 taken together form glycine-methyl-ester or valine methyl ester; or when R1 is N or NH, R2 is ethyl-dimethylamine-oxide, propyl-dimethylamine-oxide, methyl, ethyl, propyl, or ethanol.

9. The disc-shaped nanoparticle of claim 7 wherein R3 is phenyl substituted by one to five methyl or —$(C_2-C_{12})$alkyl groups.

10. The disc-shaped nanoparticle of claim 7 wherein the hydrophilic subunit b of the copolymer and hydrophobic subunit a of the copolymer are present in an equimolar ratio and in a substantially alternating pattern along the linear sequence of the copolymer.

11. The disc-shaped nanoparticle of claim 7, wherein the copolymer has a number averaged molecular weight of at least 3 kilodaltons.

12. The disc-shaped nanoparticle of claim 7, wherein the copolymer is:

poly(styrene-alt-maleamic acid-histamine) (1), poly(styrene-alt-maleimide-histamine) (2), poly(styrene-alt-maleamic acid-ethyl-dimethylamine-oxide) (3), poly (styrene-alt-maleimide-propyl-dimethylamine-oxide) (4), poly(styrene-alt-maleamic acid-propyl-dimethylamine-oxide) (5), poly(styrene-alt-maleimide-propyl-dimethylamine-oxide) (6), poly(styrene-alt-maleamic acid-1,3-propanediol) (7), poly(styrene-alt-maleimide-1,3-propanediol) (8), poly (styrene-alt-maleamic acid-methylamine) (9), poly(styrene-alt-maleamic acid-ethylamine) (10), poly (styrene-alt-maleamic acid-propylamine) (11), poly(styrene-alt-maleamic acid-glycine-methyl-ester) (12), poly (styrene-alt-maleamic acid-glycine-methyl-ester) (13), poly(styrene-alt-maleamic acid-glycine, valine-methyl-ester) (14), poly (ortho-methyl-stilbene-maleic acid) (15), poly (ortho-methyl-stilbene-maleamic acid) (16), poly(para-methyl-stilbene-maleic acid) (17), or poly para-methyl-stilbene-maleamic acid) (18).

13. The disc-shaped nanoparticle of claim 7 wherein R2 is —$(C_1-C_{12})$ alkyl substituted with halo.

14. The disc-shaped nanoparticle of claim 7 wherein the nanoparticle has a diameter of 5 nm to about 100 nm.

15. The disc-shaped nanoparticle of claim 7 wherein the biological material originates from brain homogenate, brain matter, biological organ, biological tissue, animal matter, plant matter, eukaryotic cells, prokaryotic cells, or a complex between lipids and membrane protein.

16. The disc-shaped nanoparticle of claim 7 wherein the biological material is bound to a biologically active agent, a drug, a co-factor, a diagnostic probe molecule, an active ingredient of a plant protective product, an active ingredient of a cosmetic product, a contrast agent, a dietary supplement, a nutritional supplement, a molecular label, or an indicator.

17. The disc-shaped nanoparticle of claim 7 wherein the one or more amphiphilic copolymers are cyclized by a crosslink between the two termini of the copolymer chain.

18. The disc-shaped nanoparticle of claim 7 wherein the positively charged monovalent counter ion is $Na^+$, $K^+$ or $NH_4^+$.

19. An amphiphilic copolymer comprising Formula $I^A$, Formula $I^B$, or a combination thereof, wherein:

i) Formula $I^A$ is represented as, ($I^A$)

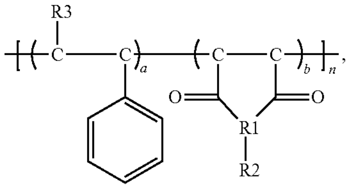

wherein

R1 is N;

R2 is ethyl-dimethylamine-oxide or propyl-dimethylamine-oxide; or

R1 and R2 taken together form serinol, ethyl-glycine-methyl-ester or valine methyl ester; and R3 is a hydrogen, unsubstituted phenyl, or phenyl substituted by one or more non-polar substituents;

ii) Formula $I^B$ is represented as, $(I^B)$

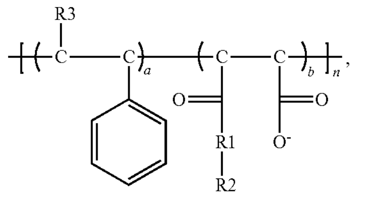

wherein

R1 is NH;

R2 is ethyl-dimethylamine-oxide or propyl-dimethylamine-oxide; or

R1 and R2 taken together form serinol, ethyl-glycine-methyl-ester or valine methyl ester; and R3 is a hydrogen, unsubstituted phenyl, or phenyl substituted by one or more non-polar substituents;

wherein the oxygen anion of Formula $I^B$ has a positively charged monovalent counter ion; and iii) independently for Formula $I^A$ and $I^B$, n is about 7 to about 200, and the monomer moieties labeled a and b are in an alternating, substantially alternating, largely alternating, or semialternating copolymer arrangement in the length of the copolymer backbone;

wherein a=b=1 for the alternating copolymer arrangement; 1<a≤1.2 and b =1 for the substantially alternating copolymer arrangement; 1.2<a≤1.4 and b=1 for the largely alternating copolymer arrangement; or 1.7≤a≤2.3 and b=1 for the semialternating copolymer arrangement.

20. An amphiphilic copolymer comprising Formula $I^A$, Formula $I^B$, or a combination thereof, wherein:

i) Formula $I^A$ is represented as, $(I^A)$

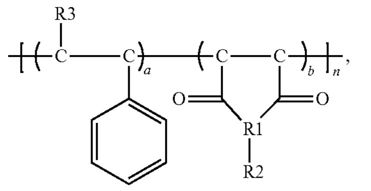

wherein

R1 is N;

R2 is —($C_1$-$C_{12}$)alkyl, alkanol, alkylamine, alkylamine oxide, or quaternary amine, wherein —($C_1$-$C_{12}$)alkyl is substituted optionally with halo; or R1 and R2 taken together form a histamine, amino alkanediol, or alkyl ester of an amino acid residue; and R3 is a phenyl substituted by one or more methyl or —($C_2$-$C_{12}$) alkyl groups;

ii) Formula $I^B$ is represented as, $(I^B)$

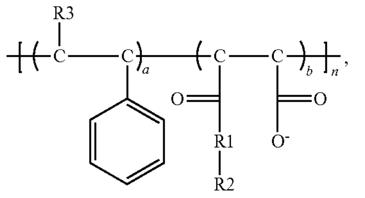

wherein

R1 is O or NH;

when R1 is O, R2 is H;

when R1 is NH:

R2 is —($C_1$-$C_{12}$)alkyl, alkanol, alkylamine, alkylamine oxide, quaternary amine, wherein —($C_1$-$C_{12}$)alkyl is substituted optionally with halo; or R1 and R2 taken together form a histamine, amino alkanediol, or alkyl ester of an amino acid residue; and R3 is a phenyl substituted by one or more methyl or —($C_2$-$C_{12}$)alkyl groups;

wherein the oxygen anion of Formula $I^B$ has a positively charged monovalent counter ion; and iii) independently for Formula $I^A$ and $I^B$, n is about 7 to about 200, and the monomer moieties labeled a and b are in an alternating, substantially alternating, largely alternating, or semialternating copolymer arrangement in the length of the copolymer backbone;

wherein a=b=1 for the alternating copolymer arrangement; 1<a≤1.2 and b =1 for the substantially alternating copolymer arrangement; 1.2<a≤1.4 and b=1 for the largely alternating copolymer arrangement; or 1.7≤a≤2.3 and b=1 for the semialternating copolymer arrangement.

21. An amphiphilic copolymer comprising Formula $I^A$, Formula $I^B$, or a combination thereof, wherein:

i) Formula $I^A$ is represented as, $(I^A)$

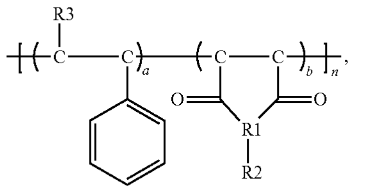

wherein

R1 is N;

R2 is —($C_1$-$C_{12}$)alkyl, alkanol, alkylamine, alkylamine oxide, or quaternary amine, wherein —($C_1$-$C_{12}$)alkyl is substituted optionally with halo; or R1 and R2 taken together form a histamine, amino alkanediol, or alkyl ester of an amino acid residue; and R3 is a hydrogen, unsubstituted phenyl, or phenyl substituted by one or more non-polar substituents;

ii) Formula $I^B$ is represented as, (I^B)

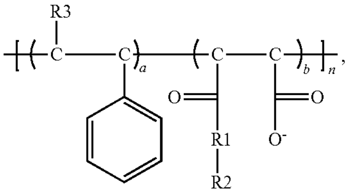

wherein

R1 is O or NH;

when R1 is O, R2 is H;

when R1 is NH:

R2 is —($C_1$-$C_{12}$)alkyl, alkanol, alkylamine, alkylamine oxide, quaternary amine, wherein —($C_1$-$C_{12}$)alkyl is substituted optionally with halo; or R1 and $R^2$ taken together form a histamine, amino alkanediol, or alkyl ester of an amino acid residue; and R3 is a hydrogen, unsubstituted phenyl, or phenyl substituted by one or more non-polar substituents;

wherein the oxygen anion of Formula $I^B$ has a positively charged monovalent counter ion; and iii) independently for Formula $I^A$ and $I^B$, n is about 7 to about 200, and the monomer moieties labeled a and b are in an alternating, substantially alternating, largely alternating, or semialternating copolymer arrangement in the length of the copolymer backbone;

wherein a=b=1 for the alternating copolymer arrangement; $1<a\leq 1.2$ and b =1 for the substantially alternating copolymer arrangement; $1.2<a\leq 1.4$ and b=1 for the largely alternating copolymer arrangement; or $1.7\leq a\leq 2.3$ and b=1 for the semialternating copolymer arrangement; and provided that for Formula $I^A$ and $I^B$, when R3 is a hydrogen, R1 is not O and R2 is not alkylamine oxide, ($C_1$-$C_3$) alkyl, quaternary amine, or alkanol;

wherein the copolymer is cyclized by a crosslink between the two termini of the copolymer chain; or wherein the copolymer is: poly(styrene-alt-maleamic acid-1,3-propanediol) (7), poly(styrene-alt-maleimide-1,3-propanediol) (8), poly(styrene-alt-maleamic acid-methylamine) (9), poly (styrene-alt-maleamic acid-ethylamine) (10), poly (styrene-alt-maleamic acid-propylamine) (11), poly(styrene-alt-maleamic acid-glycine-methyl-ester) (12), poly(styrene-alt-maleamic acid-glycine-methyl-ester) (13), poly(styrene-alt-maleamic acid-glycine, valine-methyl-ester) (14), poly (ortho-methyl-stilbene-maleamic acid) (16), or poly(para-methyl-stilbene-maleamic acid) (18).

* * * * *